US012642201B2

(12) United States Patent
    Villamar

(10) Patent No.:    US 12,642,201 B2
(45) Date of Patent:    Jun. 2, 2026

(54) GEODESIC DOME SYSTEM FOR INTEGRATED AQUAPONICS AND MUSHROOM PRODUCTION

(71) Applicant: Carlos R. Villamar, Falls Church, VA (US)

(72) Inventor: Carlos R. Villamar, Falls Church, VA (US)

( * ) Notice: Subject to any disclaimer, the term of this patent is extended or adjusted under 35 U.S.C. 154(b) by 0 days.

(21) Appl. No.: 19/199,210

(22) Filed: May 5, 2025

(65) Prior Publication Data

US 2025/0268160 A1     Aug. 28, 2025

Related U.S. Application Data

(60) Division of application No. 18/218,456, filed on Jul. 5, 2023, now Pat. No. 12,290,032, which is a
(Continued)

(51) Int. Cl.
*A01G 31/02*      (2006.01)
*A01G 9/14*      (2006.01)
(Continued)

(52) U.S. Cl.
CPC .............. *A01G 31/02* (2013.01); *A01G 9/14* (2013.01); *A01K 61/10* (2017.01); *A01K 61/80* (2017.01);
(Continued)

(58) Field of Classification Search
CPC ........ A01K 61/10; A01K 61/80; A01K 67/30; A01K 9/14; A01K 63/04; A01K 63/042;
(Continued)

(56) References Cited

U.S. PATENT DOCUMENTS 4,060,054 A   *   11/1977   Blair ................... A01K 1/0041
                                        119/447
4,136,670 A   *   1/1979   Davis ..................... F24S 23/30
                                        126/584
(Continued)

FOREIGN PATENT DOCUMENTS

CN       104221982 A     12/2014
CN       205030256 U     2/2016
(Continued)

OTHER PUBLICATIONS

"Pump for the food industry—RD-Hygienic—ViscoTec Pumpen" accessed on the worldwide web at directindustry.com on Jul. 10, 2022, 5:34 PM.
(Continued)

*Primary Examiner* — Monica L Perry
*Assistant Examiner* — Aaron M Rodziwicz
(74) *Attorney, Agent, or Firm* — Carlos R. Villamar; The Villamar Firm PLLC

(57)            ABSTRACT

A geodesic dome system for integrated aquaponics and mushroom production is disclosed. The system includes a geodesic dome enclosing an interior volume, with a plurality of panels configured such that a first region receives direct sunlight and a second region remains shaded. A fish tank is centrally located within the dome and is thermally coupled to a water tube that extends outward to regulate interior temperature. A plant growing area is disposed in the sunlit region, while a mushroom growing area is located in the shaded region. A natural air ventilation system includes a misting nozzle positioned at an upper portion of the dome, the nozzle being configured to introduce cooled misted air into the shaded region while drawing heated air upward from the sunlit region. The system creates a closed-loop,
(Continued)

zoned environment for fish, plant, and mushroom co-pro-duction using passive environmental control.

20 Claims, 44 Drawing Sheets

Related U.S. Application Data continuation-in-part of application No. 17/902,897, filed on Sep. 5, 2022, now Pat. No. 11,997,961, which is a continuation-in-part of application No. 17/157, 747, filed on Jan. 25, 2021, now Pat. No. 11,432,486, which is a continuation-in-part of application No. 16/908,488, filed on Jun. 22, 2020, now Pat. No. 10,897,861, which is a continuation-in-part of appli-cation No. 16/265,843, filed on Feb. 1, 2019, now Pat. No. 10,687,485, which is a continuation-in-part of application No. 15/917,839, filed on Mar. 11, 2018, now Pat. No. 10,194,601, which is a continuation-in-part of application No. 15/783,684, filed on Oct. 13, 2017, now Pat. No. 10,015,940, which is a division of application No. 15/446,863, filed on Mar. 1, 2017, now Pat. No. 9,788,496, which is a continuation-in-part of application No. 14/633,387, filed on Feb. 27, 2015, now Pat. No. 9,585,315.

(60) Provisional application No. 61/946,690, filed on Feb. 28, 2014.

(51) Int. Cl.
| | |
|---|---|
| *A01K 61/10* | (2017.01) |
| *A01K 61/80* | (2017.01) |
| *A01K 63/04* | (2006.01) |
| *A01K 63/06* | (2006.01) |
| *A01K 67/30* | (2025.01) |

(52) U.S. Cl.
CPC ............ *A01K 63/04* (2013.01); *A01K 63/042* (2013.01); *A01K 63/045* (2013.01); *A01K 63/047* (2013.01); *A01K 63/065* (2013.01); *A01K 67/30* (2025.01)

(58) Field of Classification Search
CPC .. A01K 63/045; A01K 63/047; A01K 63/065; A01G 31/02
See application file for complete search history.

(56) References Cited

U.S. PATENT DOCUMENTS

| | | | | |
|---|---|---|---|---|
| 5,046,451 A | * | 9/1991 | Inslee | A01K 61/10 210/167.26 |
| 5,335,447 A | * | 8/1994 | Bee | A01G 9/225 47/17 |
| 6,131,363 A | * | 10/2000 | Phillips | A01G 9/1438 52/173.3 |
| 8,915,015 B1 | * | 12/2014 | Augspurger | A01G 9/14 47/17 |
| 2003/0024874 A1 | * | 2/2003 | Wallace | C02F 3/00 210/150 |
| 2007/0062105 A1 | * | 3/2007 | Stevens | A01G 9/14 47/17 |
| 2007/0166171 A1 | * | 7/2007 | Kondo | F04F 1/18 417/118 |
| 2009/0178348 A1 | * | 7/2009 | Flaherty | F24S 10/73 126/646 |
| 2009/0250053 A1 | * | 10/2009 | Flaherty | F24S 20/25 220/592.27 |
| 2009/0301399 A1 | * | 12/2009 | Brown | A01K 63/065 47/17 |
| 2010/0031893 A1 | * | 2/2010 | Bodlovich | C02F 3/32 119/260 |
| 2010/0038440 A1 | * | 2/2010 | Ersavas | G05D 7/0617 236/51 |
| 2011/0167716 A1 | * | 7/2011 | Myntti | F24S 90/00 47/17 |
| 2011/0220099 A1 | * | 9/2011 | Flaherty | F24S 80/54 126/709 |
| 2012/0036774 A1 | | 2/2012 | PelesZezak | |
| 2012/0067339 A1 | * | 3/2012 | Hall | A01G 9/243 126/714 |
| 2012/0174478 A1 | * | 7/2012 | Chen | F24S 20/67 47/17 |
| 2013/0008386 A1 | * | 1/2013 | Jacobs | A01K 63/02 119/224 |
| 2015/0053366 A1 | * | 2/2015 | Melsheimer | E04H 14/00 165/10 |
| 2015/0196002 A1 | | 7/2015 | Friesth | |
| 2015/0196880 A1 | | 7/2015 | Stone et al. | |
| 2015/0223407 A1 | * | 8/2015 | Carroll | A01G 9/243 47/17 |
| 2018/0092337 A1 | | 4/2018 | Hori | |
| 2020/0163285 A1 | | 5/2020 | Sim | |

FOREIGN PATENT DOCUMENTS

| | | | | |
|---|---|---|---|---|
| CN | 105935026 A | | 9/2016 | |
| CN | 106973695 A | | 7/2017 | |
| CN | 107494063 A | | 12/2017 | |
| EP | 2048455 A2 | | 4/2009 | |
| JP | 2011078332 A | | 4/2011 | |
| KR | 101262244 B1 | | 6/2011 | |
| KR | 20120104486 A | | 9/2012 | |
| KR | 20180004696 A | | 9/2012 | |
| KR | 20150007905 A | | 1/2015 | |
| KR | 20170072977 A | | 6/2017 | |
| TW | 201603699 A | | 2/2016 | |
| WO | WO-8301501 A1 | * | 4/1983 | F24S 60/30 |
| WO | WO-2011008187 A1 | * | 1/2011 | F24S 10/70 |
| WO | WO-2022120506 A1 | * | 6/2022 | H02S 40/44 |

OTHER PUBLICATIONS

"Programmable Peristaltic Pumps 9000 Series" accessed on the worldwide web at SyringePump.com on Jul. 10, 2022, 5:37 PM.
"Solenoid valve—Wikipedia" accessed on the worldwide web at en.wikipedia.org/wiki/Solenoid_valve on Jul. 10, 2022, 5:18 PM.
"Massflow 500 programmable gas flow controller" accessed on the worldwide web at peristalticpump.info on Jul. 10, 2022, 5:38 PM.
"Compact Solenoid Valves" accessed on the worldwide web at emerson.com on Jul. 31, 2022, 8:17 AM.
"7 Best Automatic Fish Feeders For Aquariums" accessed on the worldwide web at fishtankbasics.com on Jul. 10, 2022, 5:40 PM.
EP Appl. No. 1976825 Search Report Oct. 18, 2021.
IN Appl. No. 202017043405 Examination Report Jun. 13, 2022.
KR Appl. No. 10-2020-7029003 Office Action of Jun. 27, 2022.
MMariola. (Jun. 29, 2012). Sustainability@Wooster. Retrieved from Sustainability.com: http://sustainability.scotblogs.wooster.edu/page/4/.
NVAC Greenhouse (Natural Ventilation Augmented Cooling), "McGill researchers develop new passive cooling and ventilation solution," Horti Daily, publication date Feb. 2, 2017, availableon World Wide Web at http://www.hortidaily.com/article/32005/McGill-researchers-develop-new-passive-cooling-and-ventilation-solution.
Mahmoud Shatel et al. "Water desalination technologies utilizing conventional and renewable energy sources," Institute of Sustain-able Energy Technology, University of Nottingham, Nottingham NG7 2rd, UK, revised Feb. 17, 2012; International Journal of Low-Carbon Technologies 2014, 9, 1-19, accepted Feb. 23, 2012, available on World Wide Web at https://academic.oup.com/ijlct/article-abstract/9/1/1/663897.
"Solar still," Wikipedia, available on World Wide Web at https://en.wikipedia.org/wiki/Solar_still, printed on Feb. 1, 2019, 1:51 PM.

(56) References Cited

OTHER PUBLICATIONS

"Fog Catchers and How to Make Your Own," available on World Wide Web at https://watersustainabilityandfogwater.wordpress.com/fog-catchers-and-how-to-make-your-own/, printed on Feb. 1, 2019, 1:48 PM.

Chris Woodford "'Smart' windows (electrochromic glass)," Explain That Stuff, Jun. 10, 2020, available on World Wide Web at https://www.explainthatstuff.com/electrochromic-windows.html.

Jessica Miley "Scientists Develop Liquid That Can Store Solar Energy For More Than a Decade," Interesting Engineering, Nov. 6, 2018, available on World Wide Web at https://interestingengineering.com/scientists-develop-liquid-that-can-store-solar-energy-for-more-than-a-decade.

Mason "Container farms in the UK can produce fish and vegetables at the same time," 3E Magazine, May 18, 2016, available on World Wide Web at http://www.3e-mag.com/View.aspx?Category=Agricultural&No=41.

* cited by examiner

FIG. 1   TOP VIEW 100

GLAZING 118

V 120

EAST SIDE

120

120 V

V 204

D

V 120

120

V

WEST SIDE

D 204

GLAZING 118

V 120

V 120

V 120

GLAZING 118

V 120

V 120

VENT/DOOR LAYOUTS 300

120 V    TOP    V 120

GLAZING 118

V 120

V 120

LID 410

OUTER RAMP 414

402

ENTRANCE

ORGANIC MATTER 408

412

INNER RAMP

416

MEDIA

404    BSF LARVAE 406

418

LEACHATE COLLECTION 420

FIG. 4    BSF AUTO FISH FEEDER (BSF) 122

HEATED AIR 506

WATER TO FISH TANK

LARGE MASS

510 ELECTRONIC VALVES

METAL COILS

WOOD/ AIR 504

WATER FROM FISH TANK

508

502

FIG. 5    ROCKET MASS HEATER (RMH) 104

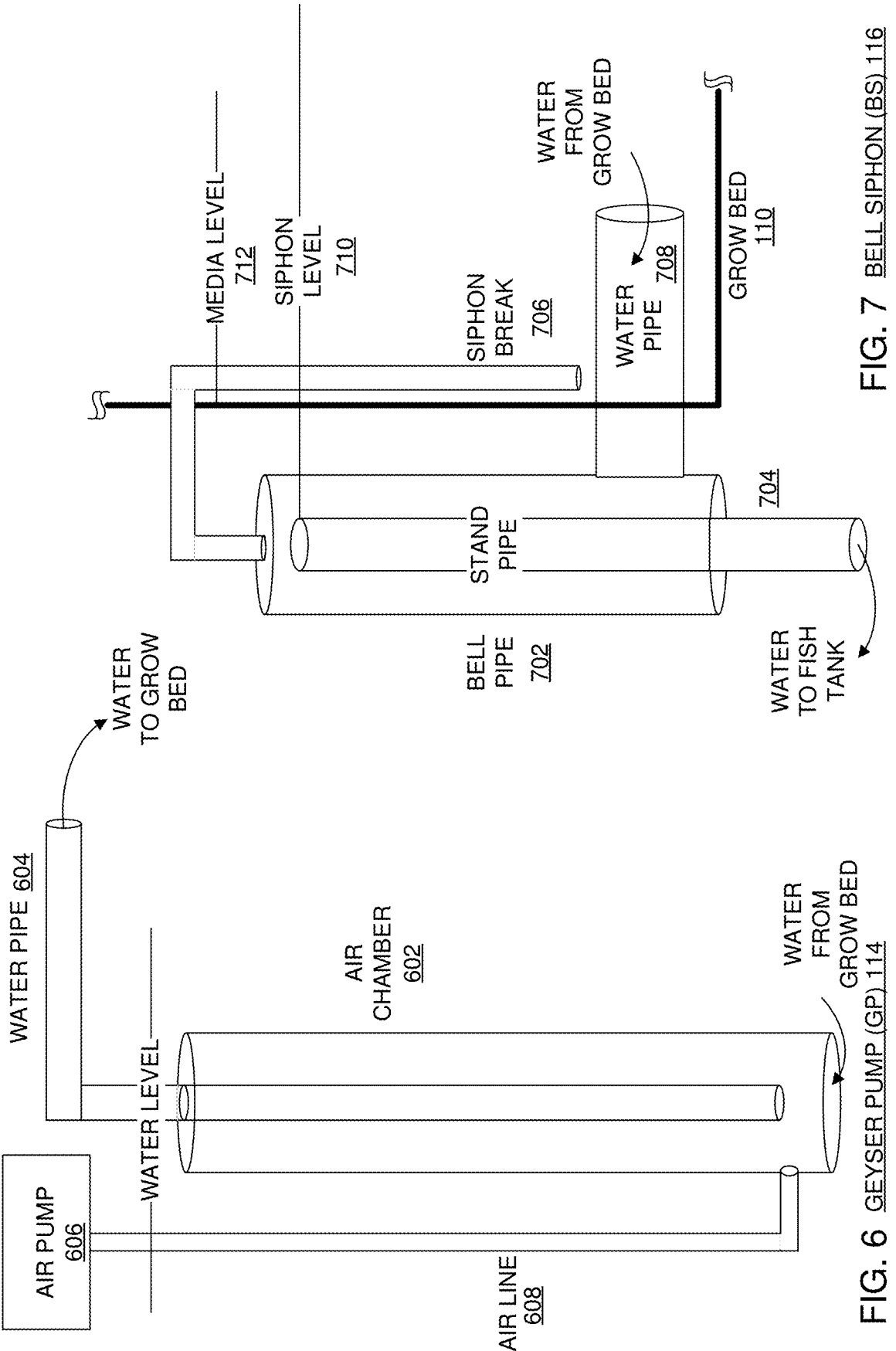
FIG. 7  BELL SIPHON (BS) 116
FIG. 6  GEYSER PUMP (GP) 114

FIG. 9B          AUTO VENT OPENER 900

FIG. 8          RAIN WATER COLLECTION (RWC) 106

WATER LOOP 1100

WATER WALL 1000

FIG. 14A      <u>HARD FILTER (HF) 112</u>

FIG. 15      <u>GEYSER PUMP (GP) 114</u>

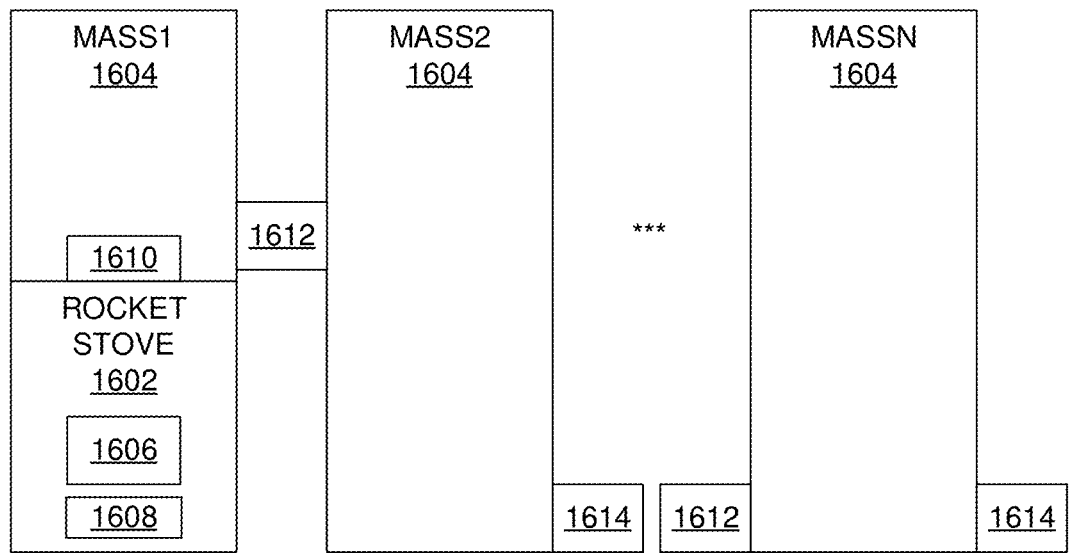
FIG. 16     ROCKET MASS HEATER (RMH) 104
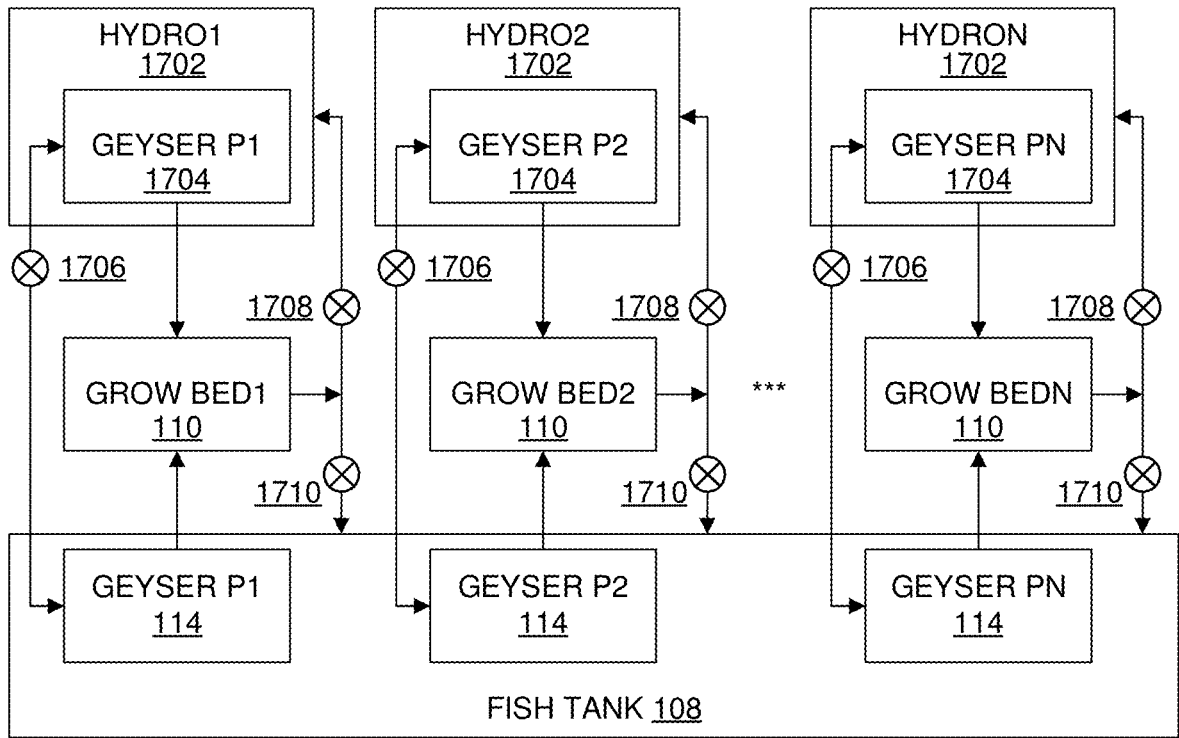
FIG. 17     AQUAPONICS/HYDRO ON DEMAND 1700

SPACER TUBES 1902

SUBSTRATE COVER 1904

GROW BED 110

MEDIA SEPARATOR 1306

FRUITING RINGS 1906

INTEGRATED AQUAPONIC MUSHROOM FILTER/WICKING BED 1800

MUSHROOM AND GREENS FRUITING CHAMBER 2000

NATURAL AIR VENTIALATION,
WATER HARVESTING CHINESE
SOLAR GREENHOUSE 2200

EVAPORATIVE PADS 2320

WATER TRAY 2310

WATER LINES 2322

AIR CHAMBER 2324

BLOWER 2318

SPORE FILTER 2304

EVAPORATIVE PADS 2320

PUMP 2308

SHELVING UNIT 2004

HOUSING 2002

FOGGER UNIT 2302

MUSHROOM LOGS/BAGS 2008

SPORE FILTER 2304

WATER TRAY 2310

OUTLET PUMP 2306    2308

GREENS RACK 2006

GREENS RACK 2006

PUMP 2312    WATER TRAY 2314

MUSHROOM AND GREENS FRUITING CHAMBER 2300

FIG. 26B

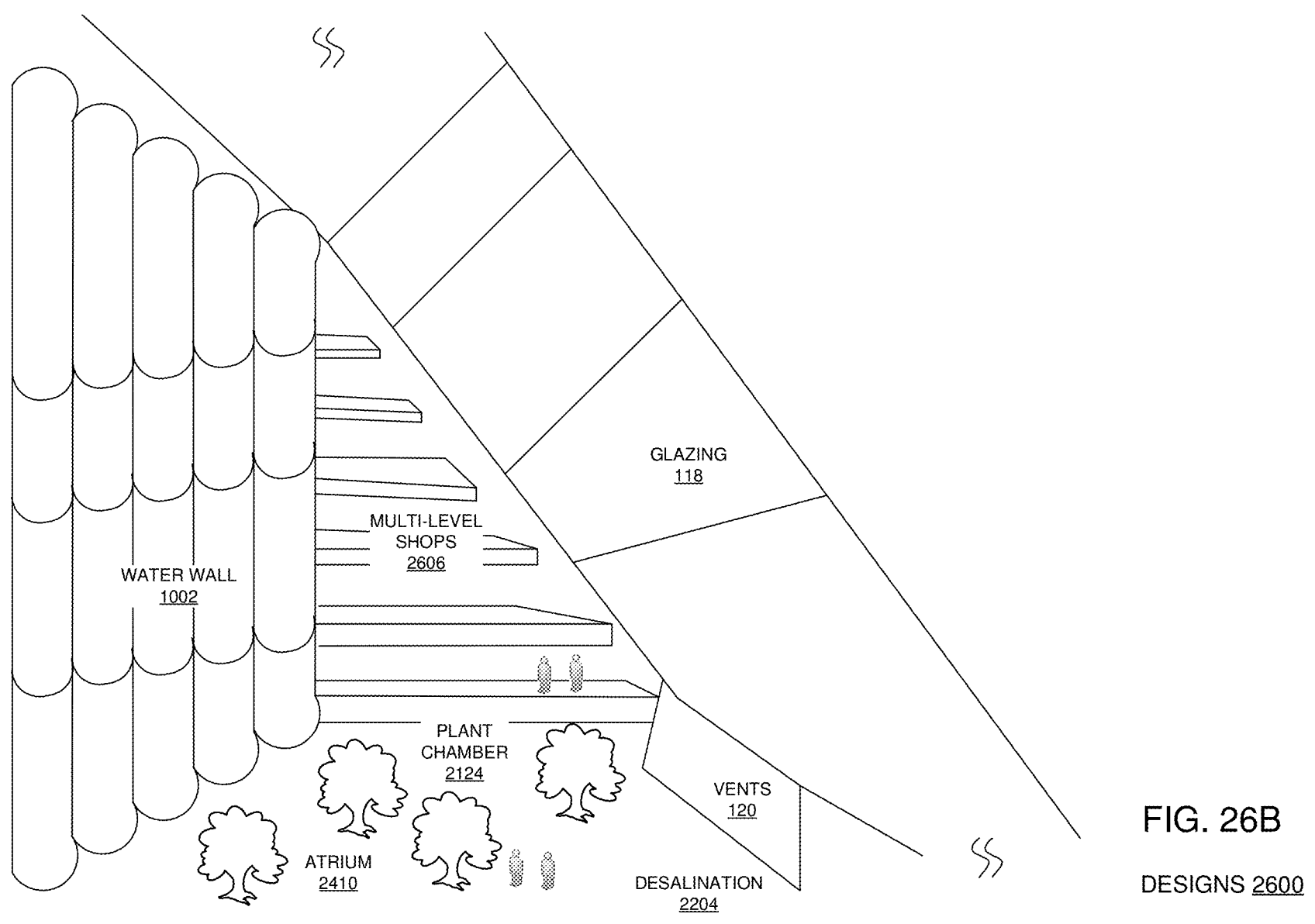

DESIGNS 2600

GLAZING 118

VENTS 120

DESALINATION 2204

MULTI-LEVEL SHOPS 2606

PLANT CHAMBER 2124

ATRIUM 2410

WATER WALL 1002

WIND
TURBINES
2414

SOLAR
PANELS
2204

SOLAR
PANELS
2204

DECK
2402

SIDE BUILDINGS
2604

NAV
2406

MULTI-LEVEL
2602

GLAZING
118

LARGE
GLAZING
2702

LOUVERS
2508

VENTS
120

SMALL
GLAZING
2704

APARTMENTS/
OFFICES/SHOPS
2512

GLAZING
118

PLANT
CHAMBER
2124

FISH
TANKS
108

ATRIUM
2410

DESALINATION
2204

WATER WALL
1002

ENTRANCE
2404

GLAZING
118

MUSHROOM
CHAMBER
2120

LAYOUT 2700

LAYOUT 2700

LAYOUT 2800

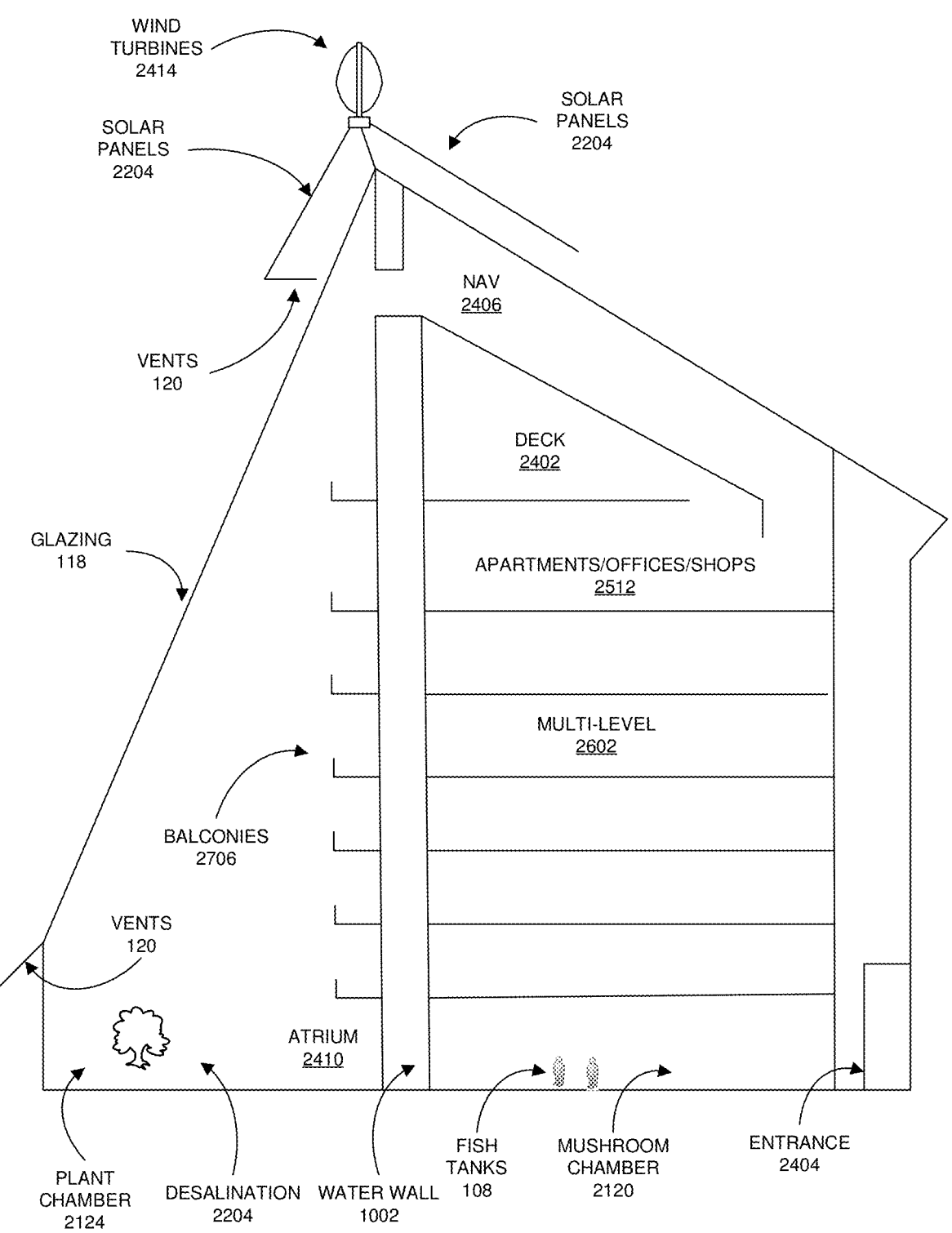
FIG. 29                                    INTERIOR LAYOUT 2900

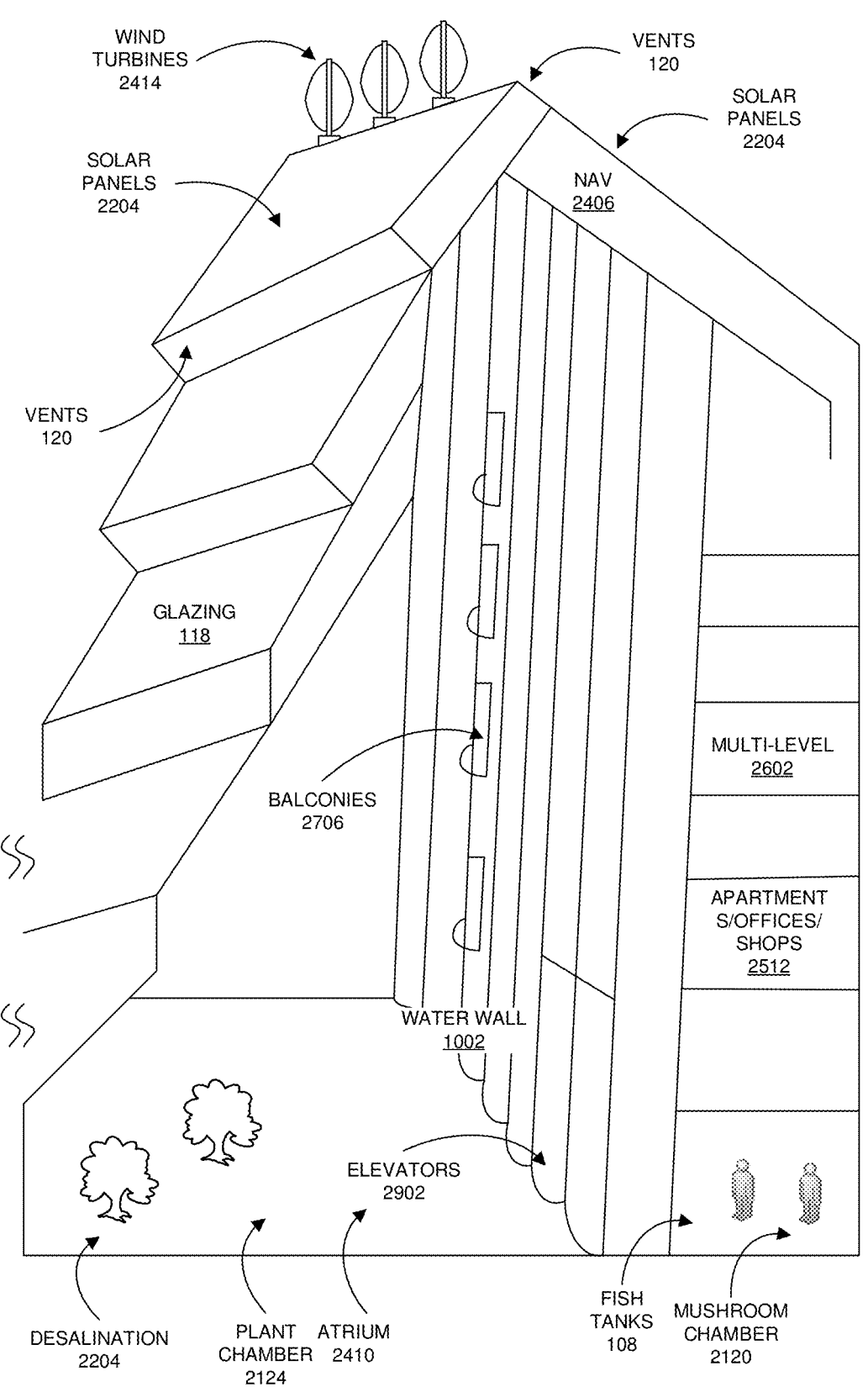
FIG. 30                                              INTERIOR LAYOUT 3000

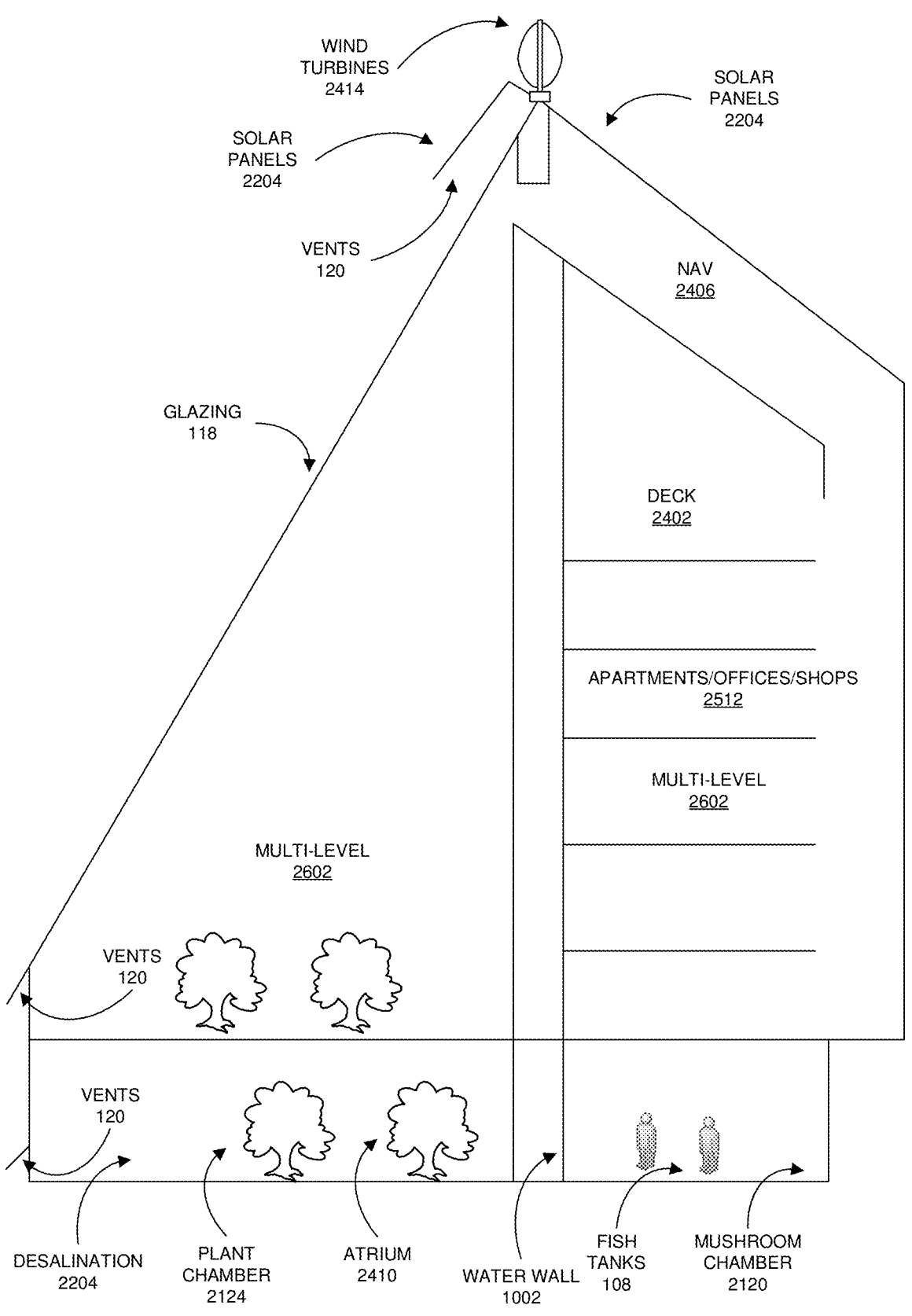
FIG. 31                                    DESIGN DETAILS 3100

BACK ROOF 3202
SCALING 3204
GLAZING 118
TECHNICAL DETAILS 3200

BACK ROOF 3202
SCALING 3204
GLAZING 118
TECHNICAL DETAILS 3200

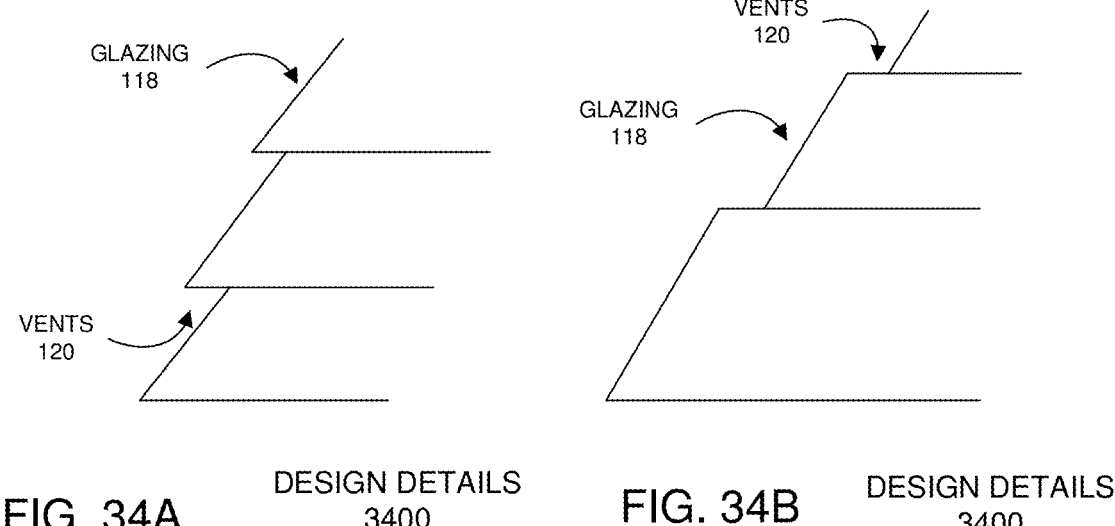
FIG. 34A          DESIGN DETAILS
                        3400
FIG. 34B          DESIGN DETAILS
                        3400
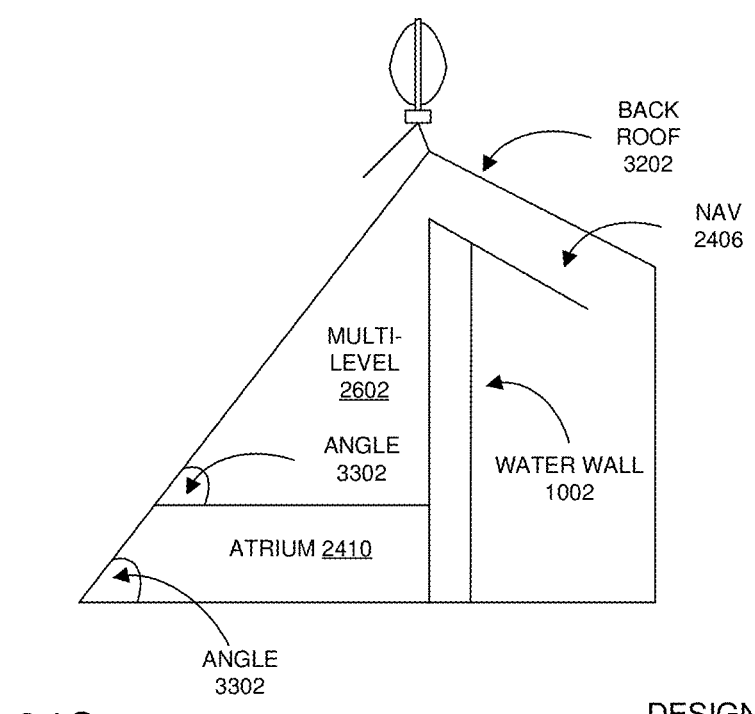
FIG. 34C          DESIGN DETAILS 3400

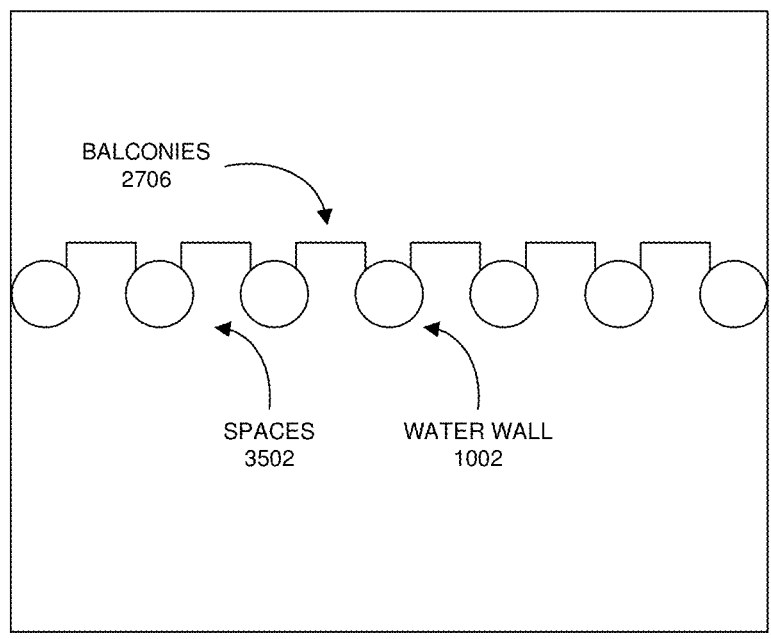
FIG. 35                                                                                    WATER WALL 3500
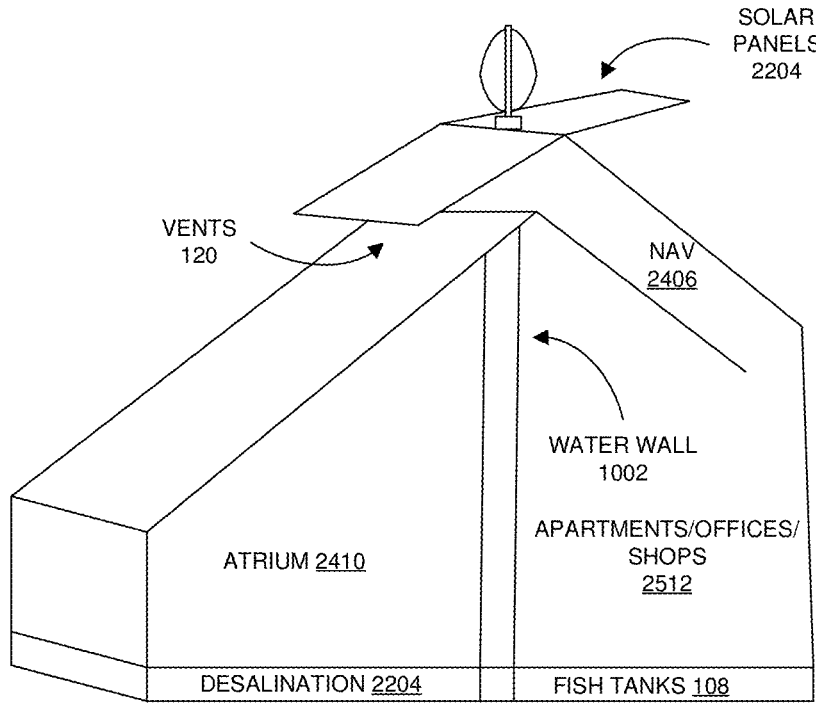
FIG. 36                                                                                    VENTS 3600

CHANNEL 3814

CIRCULAR PLENUM 3812

NAV 3816

ROTATION JOINT 3808

WATER TUBE 3802

FISH TANKS 108

DESALINATION 2204

OUTER SHELL 3804

PANELS 3806

GEODESIC DOME WITH NATURAL AIR VENTILATION 3800

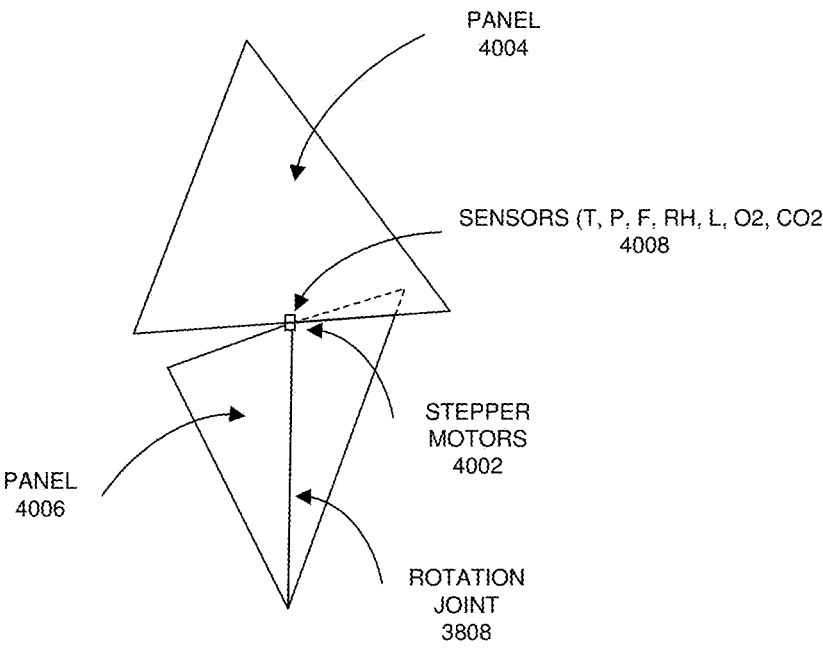
PANEL
4004
SENSORS (T, P, F, RH, L, O2, CO2)
4008
STEPPER
MOTORS
4002
PANEL
4006
ROTATION
JOINT
3808
FIG. 40                    PANELS 3806
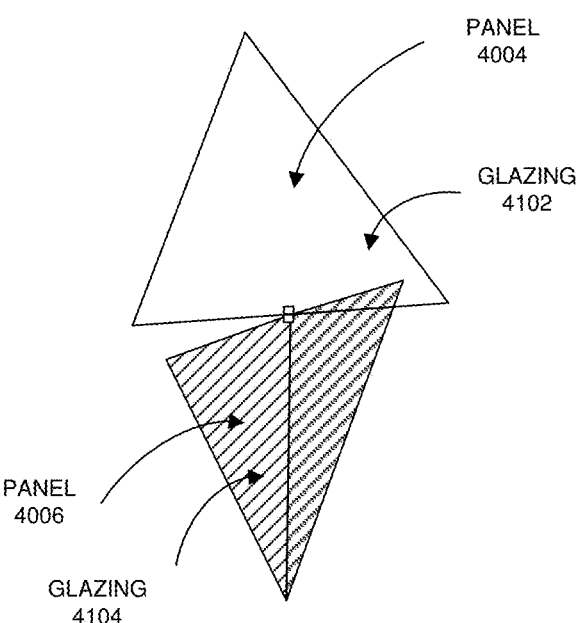
PANEL
4004
GLAZING
4102
PANEL
4006
GLAZING
4104
FIG. 41                    PANELS 3806

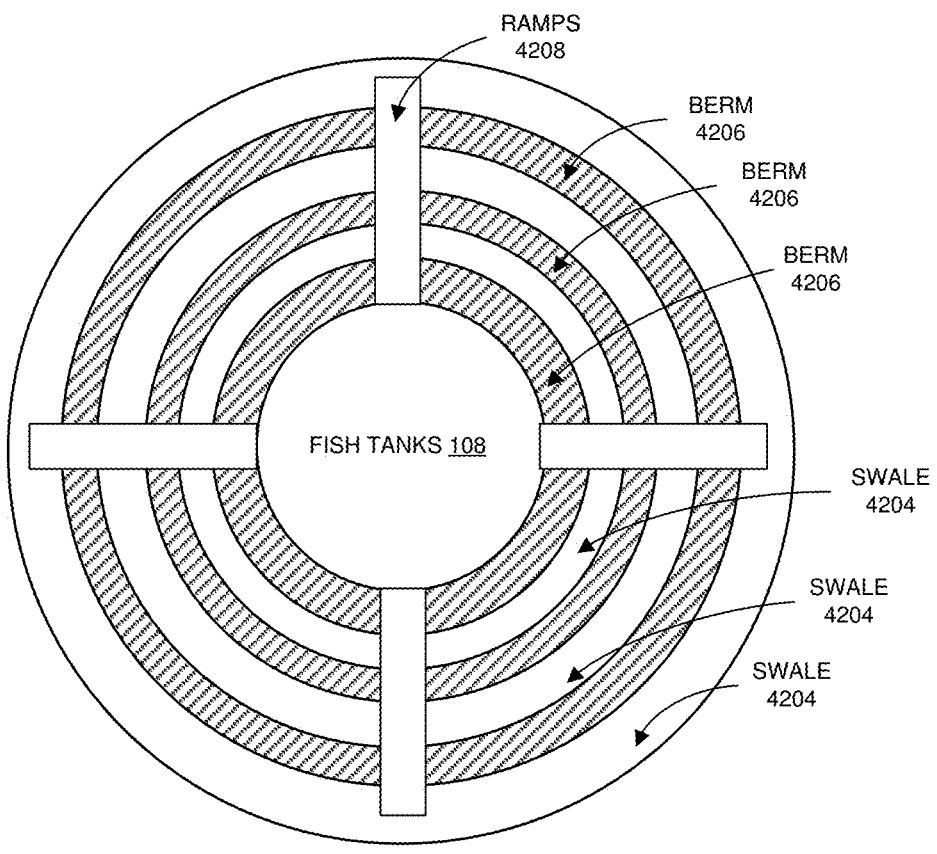
FIG. 42                                    CIRCULAR SWALE SYSTEM 4200
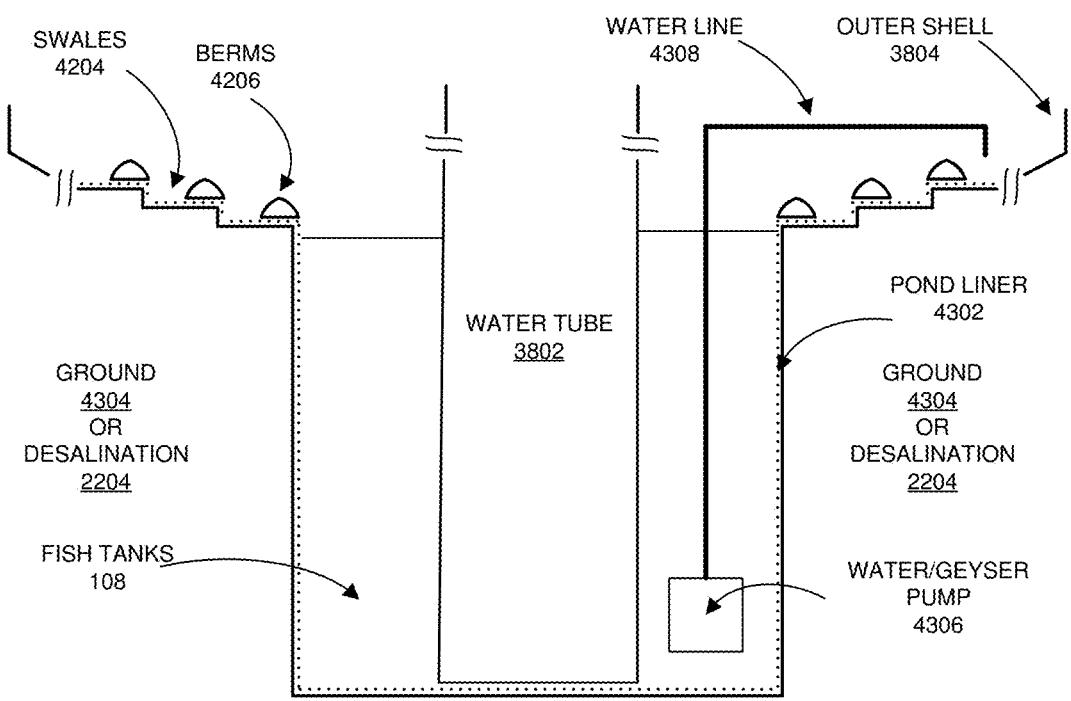
FIG. 43                                    CIRCULAR SWALE SYSTEM 4200

NATURAL AIR VENTIALATION, WATER HARVESTING SHIPPING CONTAINER SOLAR GREENHOUSE 2200

NATURAL AIR VENTIALATION, WATER HARVESTING SHIPPING CONTAINER SOLAR GREENHOUSE 2200

NATURAL AIR VENTIALATION, WATER HARVESTING SHIPPING CONTAINER SOLAR GREENHOUSE 2200

NATURAL AIR VENTIALATION, WATER HARVESTING SHIPPING CONTAINER SOLAR GREENHOUSE 2200

GEODESIC DOME SYSTEM FOR INTEGRATED AQUAPONICS AND MUSHROOM PRODUCTION

CROSS REFERENCE TO RELATED DOCUMENTS

The present application is a divisional of U.S. patent application Ser. No. 18/218,456 of VILLAMAR, entitled "N-WAY REDUNDANT AIR-POWERED AQUAPONICS SYSTEM," filed on 5 Jul. 2023, now allowed, which is a continuation-in-part of U.S. patent application Ser. No. 17/902,897 of VILLAMAR, entitled "SYSTEM AND METHOD FOR ARRAY OF PASSIVE SOLAR AQUA-PONICS STRUCTURES WITH MUSHROOM CULTIVA-TION," filed on 5 Sep. 2022, now U.S. Pat. No. 11,997,961, which is a continuation-in-part of U.S. patent application Ser. No. 17/157,747 of HAVERKAMP et al., entitled "SYS-TEM AND METHOD FOR PASSIVE SOLAR CONTAIN-ERS WITH INTEGRATED AQUAPONICS, GREEN-HOUSE AND MUSHROOM CULTIVATION," filed on 25 Jan. 2021, now U.S. Pat. No. 11,432,486, which is a con-tinuation-in-part of U.S. patent application Ser. No. 16/908,488 of PISARENKO et al., entitled "SYSTEM AND METHOD FOR PASSIVE SOLAR HOUSES, BUILDINGS AND SKYSCRAPERS WITH INTEGRATED AQUAPON-ICS, GREENHOUSE AND MUSHROOM CULTIVA-TION," filed on 22 Jun. 2020, now U.S. Pat. No. 10,897,861, which is a continuation-in-part of U.S. patent application Ser. No. 16/265,843 of VILLAMAR, entitled "SYSTEM AND METHOD FOR SOLAR GREENHOUSE AQUA-PONICS AND BLACK SOLDIER FLY COMPOSTER AND AUTO FISH FEEDER," filed on 1 Feb. 2019, now U.S. Pat. No. 10,687,485, which is a continuation-in-part of U.S. patent application Ser. No. 15/917,839 of VILLAMAR, entitled "SYSTEM AND METHOD FOR SOLAR GREEN-HOUSE AQUAPONICS AND BLACK SOLDIER FLY COMPOSTER AND AUTO FISH FEEDER," filed on 11 Mar. 2018, now U.S. patent Ser. No. 10/194,601, which is a continuation-in-part of U.S. patent application Ser. No. 15/783,684 of VILLAMAR, entitled "SYSTEM AND METHOD FOR SOLAR GREENHOUSE AQUAPONICS AND BLACK SOLDIER FLY COMPOSTER AND AUTO FISH FEEDER," filed on 13 Oct. 2017, now U.S. Pat. No. 10,015,940, which is a divisional of U.S. patent application Ser. No. 15/446,863 of VILLAMAR, entitled "SYSTEM AND METHOD FOR SOLAR GREENHOUSE AQUA-PONICS AND BLACK SOLDIER FLY COMPOSTER AND AUTO FISH FEEDER," filed on 1 Mar. 2017, now U.S. Pat. No. 9,788,496, which is a continuation-in-part of U.S. patent application Ser. No. 14/633,387 of VILLAMAR, entitled "SYSTEM AND METHOD FOR SOLAR GREEN-HOUSE AQUAPONICS AND BLACK SOLDIER FLY COMPOSTER AND AUTO FISH FEEDER," filed on 27 Feb. 2015, now U.S. Pat. No. 9,585,315, which claims priority to U.S. Provisional Patent Application Ser. No. 61/946,690 of VILLAMAR, entitled "SYSTEM AND METHOD FOR SOLAR GREENHOUSE AQUAPONICS AND BLACK SOLDIER FLY COMPOSTER AND AUTO FISH FEEDER," filed on 28 Feb. 2014, the entire disclo-sures of all of which are hereby incorporated by reference herein.

BACKGROUND OF THE INVENTION

Field of the Invention

The present invention generally relates to systems and methods for aquaponics and greenhouse technologies, and more particularly to systems and methods for solar green-house aquaponics and black soldier fly (BSF) composter and auto fish feeder, and the like.

Discussion of the Background

In recent years, aquaponics and greenhouse systems, and the like, have been developed. However, such systems typically are lacking in effective incorporation of passive solar greenhouse, fish feeding systems for the aquaponics, in an efficient and cost-effective manner.

SUMMARY OF THE INVENTION

Therefore, there is a need for a method and system that addresses the above and other problems. The above and other problems are addressed by the illustrative embodi-ments of the present invention, which provide systems and methods for solar greenhouse aquaponics and black soldier fly (BSF) composter and auto fish feeder, and the like.

Accordingly, in illustrative aspects of the present inven-tion there is provided a geodesic dome system for integrated aquaponics and mushroom production. The system includes a geodesic dome enclosing an interior volume, with a plurality of panels configured such that a first region receives direct sunlight and a second region remains shaded. A fish tank is centrally located within a central portion of the interior volume and is thermally coupled to a water tube that extends outward to regulate interior temperature. A plant growing area is disposed in the sunlit region, while a mushroom growing area is located in the shaded region. A natural air ventilation system includes a misting nozzle positioned at an upper portion of the dome, the nozzle being configured to introduce cooled misted air into the shaded region while drawing heated air upward from the sunlit region. The system creates a closed-loop, zoned environ-ment for fish, plant, and mushroom co-production using passive environmental control.

The system further includes a misting nozzle disposed atop a plenum structure positioned above the water tube, the misting nozzle configured to rotate 360 degrees to direct misted air toward the mushroom growing area.

The system further includes the plenum structure that comprises a mushroom-shaped profile and is thermally coupled to the water tube.

The system further includes the misting nozzle that is further configured to deliver evaporatively cooled air based on environmental conditions within the interior volume.

The system further includes at least one of the plurality of panels that is selectively transmissive, reflective, or photo-voltaic.

The system further includes at least one of the plurality of panels that is rotatably mounted and coupled to a stepper motor.

The system further includes the stepper motor that is configured to be controlled based on signals received from one or more environmental sensors.

The system further includes at least one of the plurality of panels that is dynamically adjusted to define the first region and the second region.

The system further includes a computer system config-ured to control at least one of the misting nozzle, panel orientation, or airflow based on input from one or more sensors.

The system further includes the input from one or more sensors that comprises measurements of temperature, humidity, light, oxygen, or carbon dioxide.

The system further includes the computer system that is configured to regulate environmental parameters using an adaptive control model.

The system further includes the water tube that is further configured to store thermal energy during daylight hours and to release the thermal energy during cooler periods.

The system further includes the water tube that is thermally coupled to the fish tank to maintain a stable water temperature within the fish tank.

The system further includes the plant growing area and the mushroom growing area that each comprise a plurality of grow beds arranged radially around the fish tank.

The system further includes a rainwater collection system integrated into the geodesic dome structure and configured to direct water into the fish tank.

The system further includes a circular swale and berm system within the interior volume that is configured to receive water from the fish tank or the plant growing area, the circular swale and berm system configured to direct the water through a sequence of alternating berms and swales and return the water to the fish tank after filtration.

The system further includes the berms that are planted with vegetation and are configured to support food production.

The system further includes a natural air ventilation system that further comprises a plurality of programmable vents distributed throughout the geodesic dome structure and configured to modulate airflow within the interior volume.

The system further includes the misting nozzle that is further configured to activate based on a humidity threshold detected within the mushroom growing area.

The system further includes the fish tank that is further configured to receive filtered water from the circular swale and berm system through a gravity-fed return channel.

Still other aspects, features, and advantages of the present invention are readily apparent from the following detailed description, by illustrating a number of illustrative embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings and in which like reference numerals refer to similar elements and in which:

FIG. 1 is a top view diagram for illustrative systems and methods for solar greenhouse aquaponics and black soldier fly (BSF) composter and auto fish feeder, and the like;

FIG. 2 is an east view diagram for the illustrative systems and methods for solar greenhouse aquaponics and black soldier fly (BSF) composter and auto fish feeder, and the like;

FIGS. 3A-3D are diagrams for venting and door layouts for the illustrative systems and methods for solar greenhouse aquaponics and black soldier fly (BSF) composter and auto fish feeder, and the like;

FIG. 4 is diagram for a black soldier fly (BSF) composter and auto fish feeder for the illustrative systems and methods for solar greenhouse aquaponics and black soldier fly (BSF) composter and auto fish feeder, and the like;

FIG. 5 is diagram for a rocket mass heater (RMH) for the illustrative systems and methods for solar greenhouse aquaponics and black soldier fly (BSF) composter and auto fish feeder, and the like;

FIG. 6 is diagram for a geyser pump (GP) for the illustrative systems and methods for solar greenhouse aquaponics and black soldier fly (BSF) composter and auto fish feeder, and the like;

FIG. 7 is diagram for a bell siphon (BS) for the illustrative systems and methods for solar greenhouse aquaponics and black soldier fly (BSF) composter and auto fish feeder, and the like;

FIG. 8 is diagram for a rain water collection system (RWC) for the illustrative systems and methods for solar greenhouse aquaponics and black soldier fly (BSF) composter and auto fish feeder, and the like;

FIGS. 9A-9B are diagrams for an auto vent opener system for the illustrative systems and methods for solar greenhouse aquaponics and black soldier fly (BSF) composter and auto fish feeder, and the like;

FIGS. 10-11 are diagrams for water collection and processing systems for the illustrative systems and methods for solar greenhouse aquaponics and black soldier fly (BSF) composter and auto fish feeder, and the like;

FIG. 12 is a diagram for a multi-level system version of the illustrative systems and methods for solar greenhouse aquaponics and black soldier fly (BSF) composter and auto fish feeder, and the like;

FIG. 13 is a diagram for additional features for the illustrative systems and methods for solar greenhouse aquaponics and black soldier fly (BSF) composter and auto fish feeder, and the like;

FIGS. 14A-14B is an illustrative hard filter employed in the systems and methods for solar greenhouse aquaponics and black soldier fly (BSF) composter and auto fish feeder;

FIG. 15 is an illustrative geyser pump air distribution configuration employed in the systems and methods for solar greenhouse aquaponics and black soldier fly (BSF) composter and auto fish feeder;

FIG. 16 is an illustrative rocket mass heater configuration employed in the systems and methods for solar greenhouse aquaponics and black soldier fly (BSF) composter and auto fish feeder;

FIG. 17 is an illustrative on-demand aquaponics or hydroponics configuration employed in the systems and methods for solar greenhouse aquaponics and black soldier fly (BSF) composter and auto fish feeder;

FIGS. 24-37 are used to illustrate passive solar houses, buildings, and skyscrapers systems employing aquaponics and greenhouse technologies with natural air ventilation suited for extreme desert, extreme cold, and space environments;

FIGS. 38-43 are used to illustrate geodesic, passive solar, aquaponics and greenhouse systems with natural air ventilation and circular swales suited for extreme desert, extreme cold and space environments;

DETAILED DESCRIPTION OF THE PREFERRED EMBODIMENTS

Figure 1:
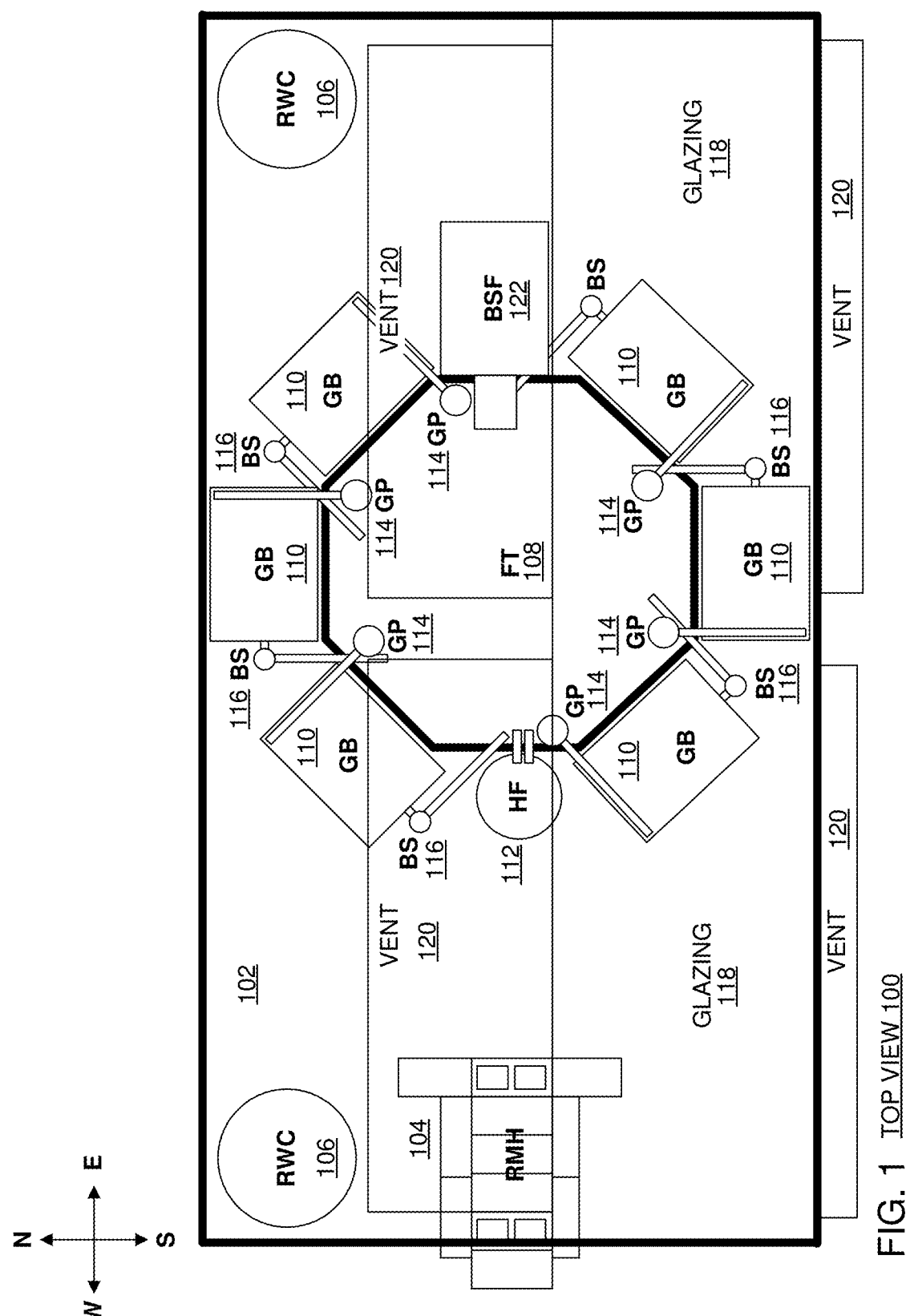

Referring now to the drawings, wherein like reference numerals designate identical or corresponding parts throughout the several views, and more particularly to FIG. 1 thereof, there shown a top view diagram 100 used for illustrative systems and methods for solar greenhouse aquaponics and black soldier fly (BSF) composter and auto fish feeder systems, and the like.

In FIG. 1, the system can include a solar greenhouse 102 (e.g., based on a Chinese solar greenhouse design, etc.) having a rocket mass heater 104 (RMH, e.g., made from fireplace bricks, metal vents, etc.) for additional heating the greenhouse and fish tank water, as needed, a rain water collection system 106 (RWC) for collecting rain water and heating the fish tank water, as needed, a fish tank 108 (FT, e.g., circular or octagonal shaped of 300-400 gallon capacity, cone bottom, etc.) for stocking fish (e.g., Tilapia, catfish, blue gills, perch, etc.), six or more grow beds 110 (GB, e.g., 27-30 gallon containers, media, deep water culture, wicking, etc.) arranged around the fish tank 108, and a hard filter 112 (HT, e.g., including mechanical, biological, chemical filtration, UV light sanitation, etc.) for additional filtering of the fish tank water, as needed. Each grow beds 110 is filled with media (e.g., expanded clay, pea gravel, soil, water, etc.) and can be fitted with respective air pump (not shown) connected to a geyser pump 114 (GP) for pumping and aerating the fish tank water from the fish tank 108 into the grow bed 110, and a bell siphon 116 for draining the water from the grow bed 110 to the fish tank 108. The greenhouse 100 can be dug into to the ground (not shown) with the east, west and north sides insulated by the earth and with the south side including a glazing 118 (e.g., 8'×4' triple wall polycarbonate panels, greenhouse plastic sheeting, glass, etc.) at an angle to maximize winter sunlight (e.g., as in an earth-sheltered design, etc.). Otherwise, the east, west and north sides can be insulated using insulation boards (not shown, e.g., 2 inch Rmax Thermashield 3 insulation, etc.), and the like. Vents 120 (e.g., including solar panels, wind turbines, etc., (not shown) to provide solar power, etc.) can be sized based on the greenhouse volume and provided on the lower east and south walls, on the upper north roof, and on the upper west side for ventilation, as needed, and based on wind direction, and the like. The greenhouse 100 can include a black soldier fly (BSF) composter and auto fish feeder 122, and a duckweed auto fish feeder (not shown, e.g., with duckweed growing on the hard filter 112 having output to fish tank 108, etc.).

Figure 2:
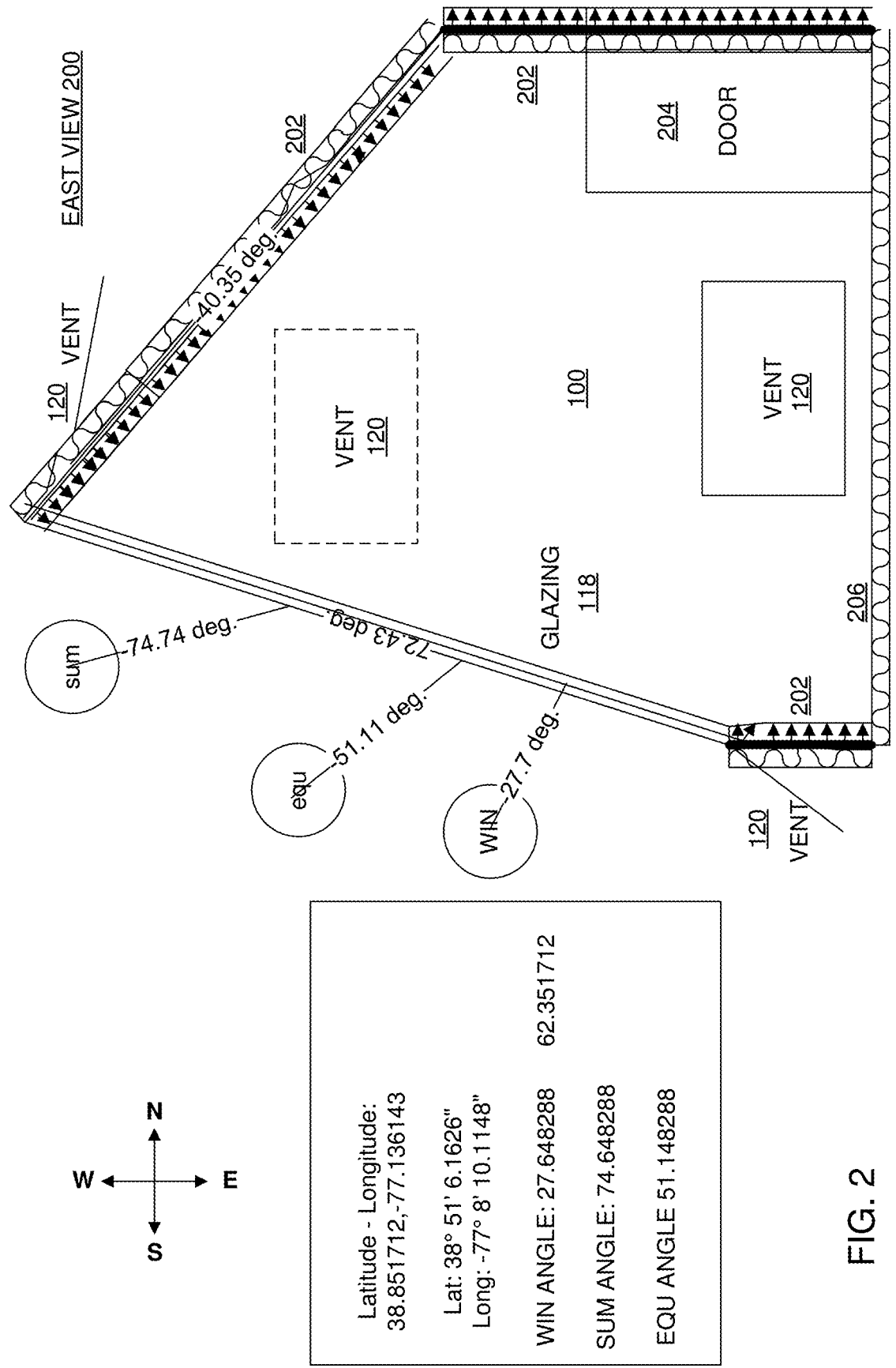
Figures 3A, 3B, 3C, 3D:
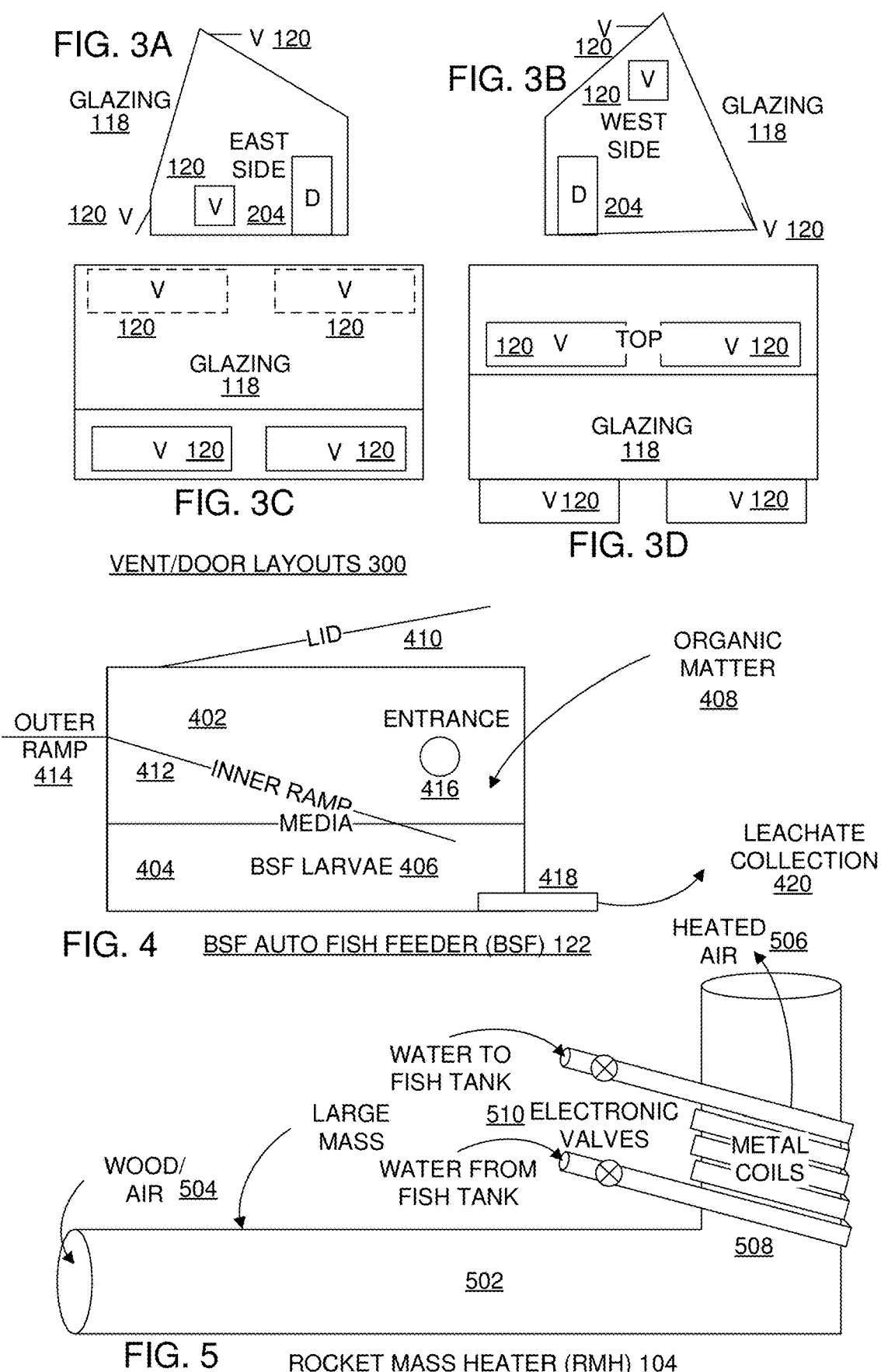

FIG. 2 is an east view diagram 200 for the illustrative systems and methods for solar greenhouse aquaponics and black soldier fly (BSF) composter and auto fish feeder, and the like. In FIG. 2, the glazing 118 (e.g., 8'×4' triple wall polycarbonate panels, greenhouse plastic sheeting, glass, etc.) is provided on the south facing wall at an angle to maximize winter (or e.g., summer, spring, fall, etc.) sunlight. The east, west and north sides can be insulated using insulation boards 202 (e.g., 2 inch Rmax Thermasheath 3 insulation, etc.), and the like. The insulation boards 202 can be reflective on the inside and/or outside, as needed, to reflect and/or trap heat within the greenhouse (e.g., based on the greenhouse effect, etc.). A solar blanket (not shown, e.g., automatically controlled, etc.) can be provide to insulate the glazing 118 at night or during dark periods, and the like, as needed. The vents 120 can be sized based on the greenhouse volume and provided on the lower east and south walls, on the upper north roof, and on the upper west side for ventilation, as needed, and based on wind direction, and the like. Doors 204 can be provided as needed, and the greenhouse 100 can be built on top of an insulated layer 206 (e.g., made from wood or plastic pallets, plastic shelves, concrete, etc.). The vents 120 can employ electronics motors and/or auto greenhouse solar window openers (e.g., wax filled cylinders/pistons that open upon heating, etc.) that are programmable to fully open within a suitable temperature range (e.g., a 40-80 degree Fahrenheit, etc.).

FIGS. 3A-3D are diagrams for venting and door layouts for the illustrative systems and methods for solar greenhouse aquaponics and black soldier fly (BSF) composter and auto fish feeder, and the like. In FIGS. 3A-3D, venting 120 and door layouts 204 are shown for (A) east side, (B) west side, (C) south side, and (D) top view. The vents 120 on the lower south side are programmable, as described above, and feed the vents 120 on the upper north side to create natural ventilation within the greenhouse.

FIG. 4 is diagram for a black soldier fly (BSF) composter and auto fish feeder 122 for the illustrative systems and methods for solar greenhouse aquaponics and black soldier fly (BSF) composter and auto fish feeder, and the like. In FIG. 4, the BSF composter and auto fish feeder 122 includes a housing 402 (e.g., made from a 30 gallon black plastic tote, etc.). The housing 402 is filled with media 404 (e.g., reptile bedding material, coco coir, etc.) that holds BSF larvae 406. Organic matter 408 is placed on top of the media through a lid 410 for the BSF larvae 406 to consume. When the larvae 406 are ready to become flies, they crawl up an inner ramp 412 (e.g., at 30-45 degrees, etc.) to an outer ramp 414 and drop into the fish tank 108 (not shown) to be consumed by the fish. Advantageously, the BSF system 122 acts as a highly efficient composter for most organic matter, and the larvae 406 provide for a high quality fish feed. An entrance hole 416 is provided for pregnant black soldier flies to enter and lay their eggs, thus generating more BSF larvae 406. An outlet 418 is provided to capture leachate juices 420 from the BSF composter and which can be diluted with water (e.g., at 20:1, etc.) and put back in the fish tank 108 (not shown) to be provided to the grow beds 110 (not shown) as fertilizer.

FIG. 5 is diagram for a rocket mass heater (RMH) 104 for the illustrative systems and methods for solar greenhouse aquaponics and black soldier fly (BSF) composter and auto fish feeder, and the like. In FIG. 5, the rocket mass heater 104 includes an L-shaped mass chamber 502 with burning wood and air 504 entering at one end, and with heated air 506 exiting at the other end to heat the greenhouse 100 (not shown). The RMH 104 can include a large mass (e.g., fire place bricks, etc.) that is heated and retains heat to be dissipated throughout the greenhouse 100 (not shown). Metal coils 508 can be wrapped around the RMH 104 to heat the fish tank water, as needed, with some electronically controlled valves 510, and the like (e.g., for computer, internet control, etc.). The RMH 104 can be buried within the floor of the greenhouse 100 (not shown) with a layer of gravel over the top to minimize the footprint.

FIG. 6 is diagram for a geyser pump (GP) 114 for the illustrative systems and methods for solar greenhouse aquaponics and black soldier fly (BSF) composter and auto fish feeder, and the like. In FIG. 6, the geyser pump 114 can include a large air chamber 602 (e.g., 4" white plastic PVC pipe, etc.) with a water stand pipe 604 (e.g., 1" white plastic PVC pipe, etc.) fitted in a center thereof. An air pump 606 (e.g., an 18-35 watt air pump running from electric, solar, wind power, etc.) is connected to an air line 608 (e.g., ¼" plastic line, etc.) that pumps air into the bottom of the air chamber 602. As the air chamber 602 fills with air, water from the bottom of the air chamber 602 is pumped to the grow bed 110 (not shown), while the fish tank 108 (not shown) water is aerated. Advantageously, each grow bed 110 (not shown) includes its own geyser pump 114 and air pump 606 providing for low energy requirements, water pumping, aeration, redundancy, and the like.

FIG. 7 is diagram for a bell siphon (BS) 116 for the illustrative systems and methods for solar greenhouse aquaponics and black soldier fly (BSF) composter and auto fish feeder, and the like. In FIG. 7, the bell siphon 116 can include a bell pipe 702 (e.g., 2"-4" white plastic PVC pipe, etc.), a stand pipe 704 (e.g., ½"-1" white plastic PVC pipe, etc.), and a siphon break line 706 (e.g., ¼"-½" clear or opaque plastic tubing, etc.). A water pipe 708 inside the grow bed 110 and connected to the bell pipe 702 takes in water from the grow bed 110. When the water reaches a siphon level 710 set by the stand pipe 704 lower than a media level 712 (e.g., approximately 2" above siphon level 710, etc.), the water starts a siphon effect and drains the water from the grow bed 110 into the fish tank 108 (not shown) faster than the water can be pumped in by the geyser pump 114 (not shown). When the water level goes down to the bottom of the siphon break 706, air is drawn in breaking the siphon, and starting a flooding cycle in the grow bed 110 from water pumped in by the geyser pump 114. Advantageously, the bell siphon 116 is located external to the grow bed 110 for ease of cleaning, maintenance, and the like.

FIG. 8 is diagram for a rain water collection system (RWC) 108 for the illustrative systems and methods for solar greenhouse aquaponics and black soldier fly (BSF) composter and auto fish feeder, and the like. In FIG. 8, the RWC system 108 can include the outside edges of the roof of the greenhouse 100 fitted with reflective gutters 802 for capturing rain. The captured rain flows through a rain water capture line 804 into one or more water collection tanks 806 (e.g., black 55 gallon, plastic drums, water wall, etc.) inside the greenhouse 100. The first water collection tank 806 can include lime stone 808, and the like, at a bottom thereof for adjusting the PH and can overflow via a connection line 810 into further water collection tanks 806. The last water collection tank 806 can include a water pump 812 (or e.g., can operate based on gravity, etc.) for pumping water into the fish tank 108 (not shown), as needed (e.g., based on a float arrangement, electronic sensor, etc.). Water from the fish tank 108 can be pumped or gravity fed to a fish tank heating line 814 for circulation in the reflective gutter 802 for solar heating of the fish tank water via electronically controlled valves 812, and the like (e.g., for computer, internet control, etc.). Advantageously, with the RWC system 106, rain water can be collected for use by the fish tank 108, fish tank water can be heated, additional water mass for solar heating by the greenhouse 100 can be provided, and the like.

Figure 9A:
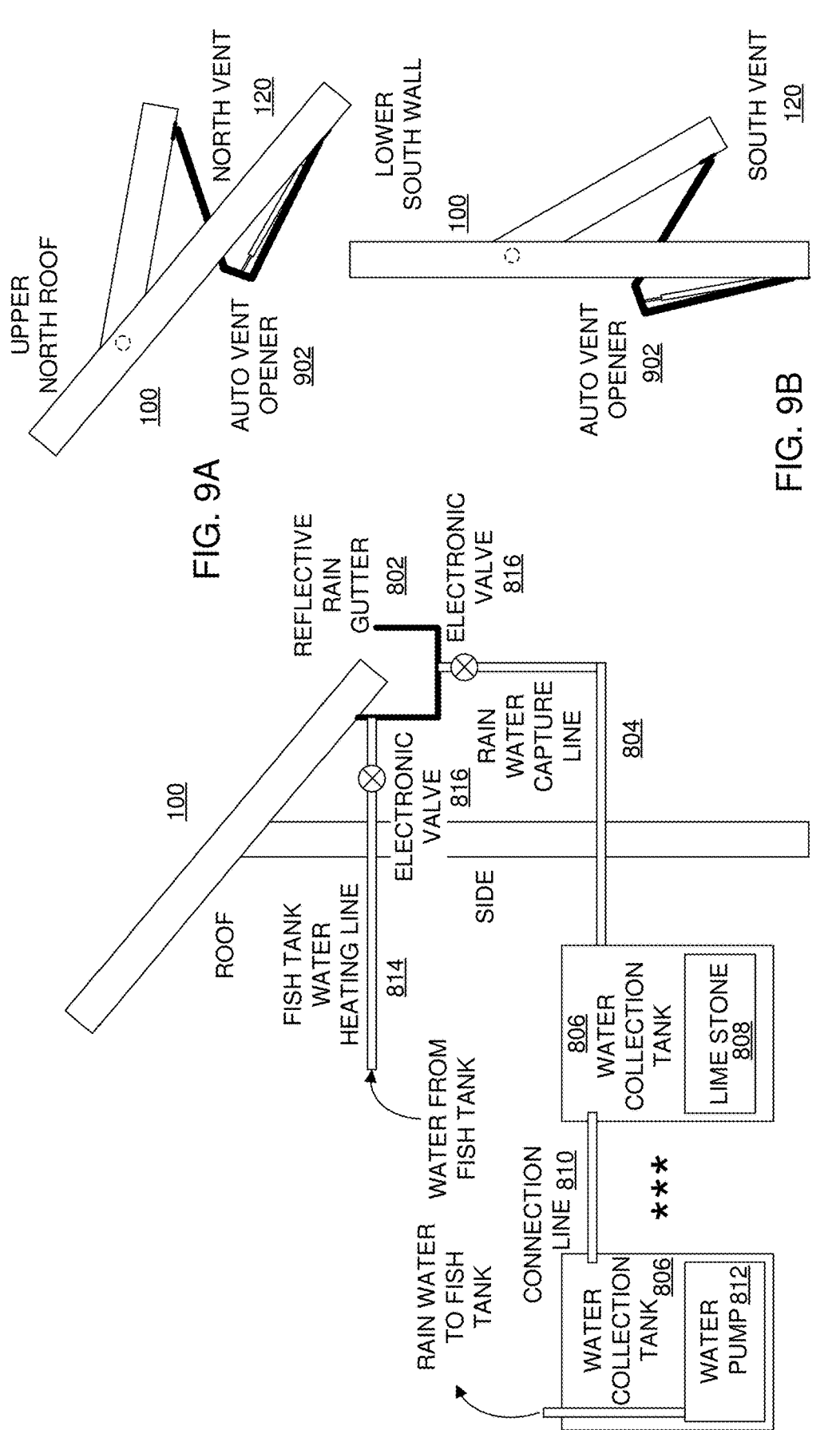

FIGS. 9A-9B are diagrams for auto vent opener system 900 for the illustrative systems and methods for solar greenhouse aquaponics and black soldier fly (BSF) composter and auto fish feeder, and the like. In FIG. 9, the auto vent opener system 900 can include vents (A) on the north roof, and (B) on the lower south wall of the greenhouse 100, employing electronics motors (not shown) and/or auto greenhouse solar window openers 902 (e.g., wax filled cylinders/pistons that open upon heating, etc.) that are programmable to fully open within a suitable temperature range (e.g., a 40-80 degree Fahrenheit, etc.).

The illustrative embodiments of FIGS. 1-9 can be fitted with additional computer controlled sensors (e.g., temperature, humidity, O2, CO2, H2O, dissolved oxygen, PH, nitrate, nitrite, ammonia, electrical conductivity (EC), etc.) for greenhouse and aquaponics automation over a LAN or the Internet, and the like, as further described.

Figures 10, 11:
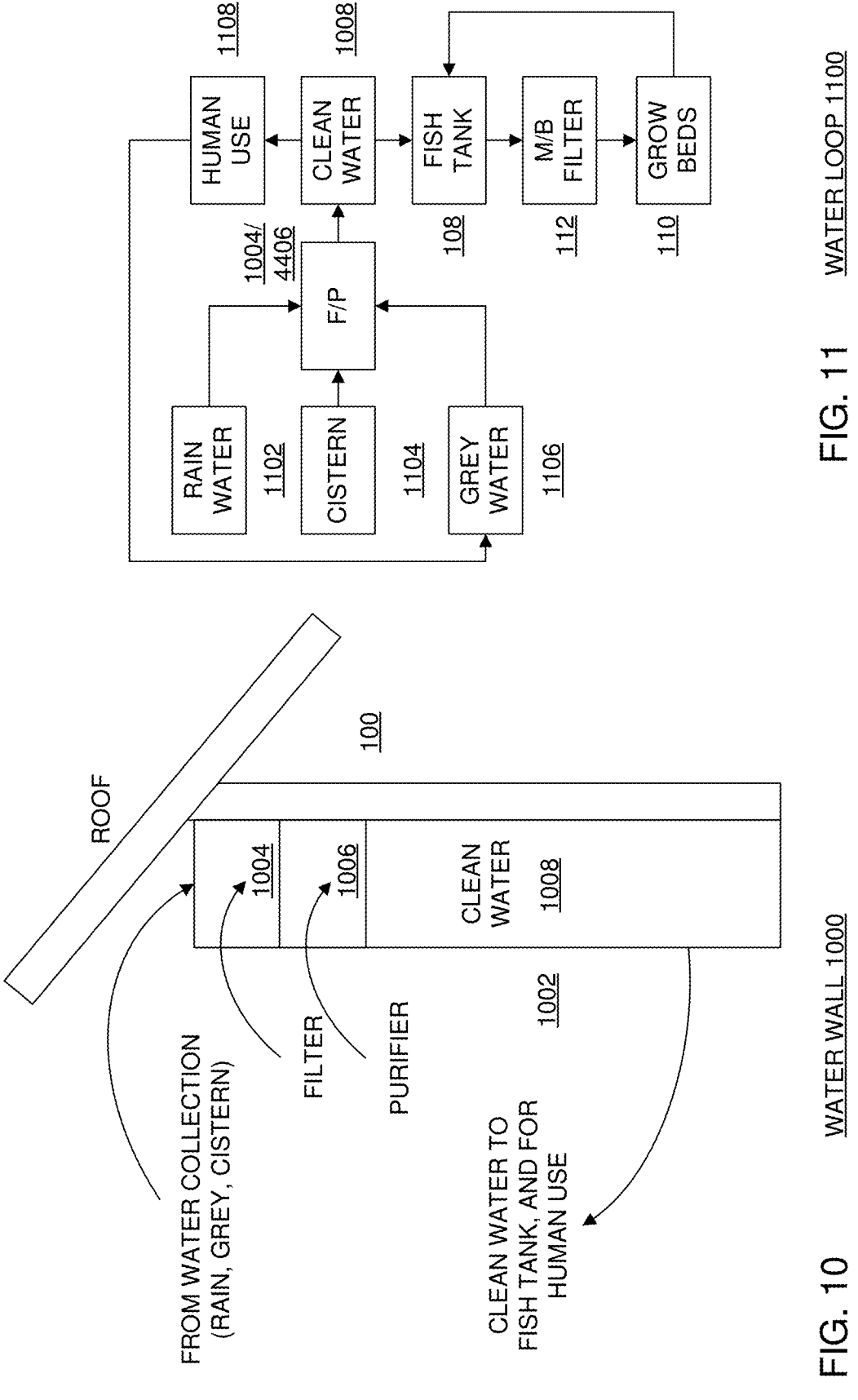

FIGS. 10-11 are diagrams for water collection and processing systems 1000-1100 for the illustrative systems and methods for solar greenhouse aquaponics and black soldier fly (BSF) composter and auto fish feeder, and the like. In FIG. 10, the water collection and processing systems 1000 can include a black colored water wall 1002 inside the greenhouse 100 for collecting rainwater and/or receiving rainwater from the RWC 106 and/or a cistern (not sown). A filter 1004 and purifier 1006 is included to provide clean water 1008 to the fish tank 108, the RWC 106, for human use, and the like. In FIG. 11, the water collection and processing systems 1000 can include collected rainwater 1102, cistern water 1104, and gray water 1106 fed to the filter 1004 and purifier 1006 to provide clean water 1008 for human use 1108 that feeds the gray water 1106. The clean water 1008 also feeds the fish tank 108 that then feeds the hard filter 112 that feeds the grow beds 110 that feeds water back to the fish tank 108 completing the loop. The fish tank 108 and the grow beds 110 can also be decoupled with respective hard filters, as needed, to optimize for fish and/or plant growth.

Figure 12:
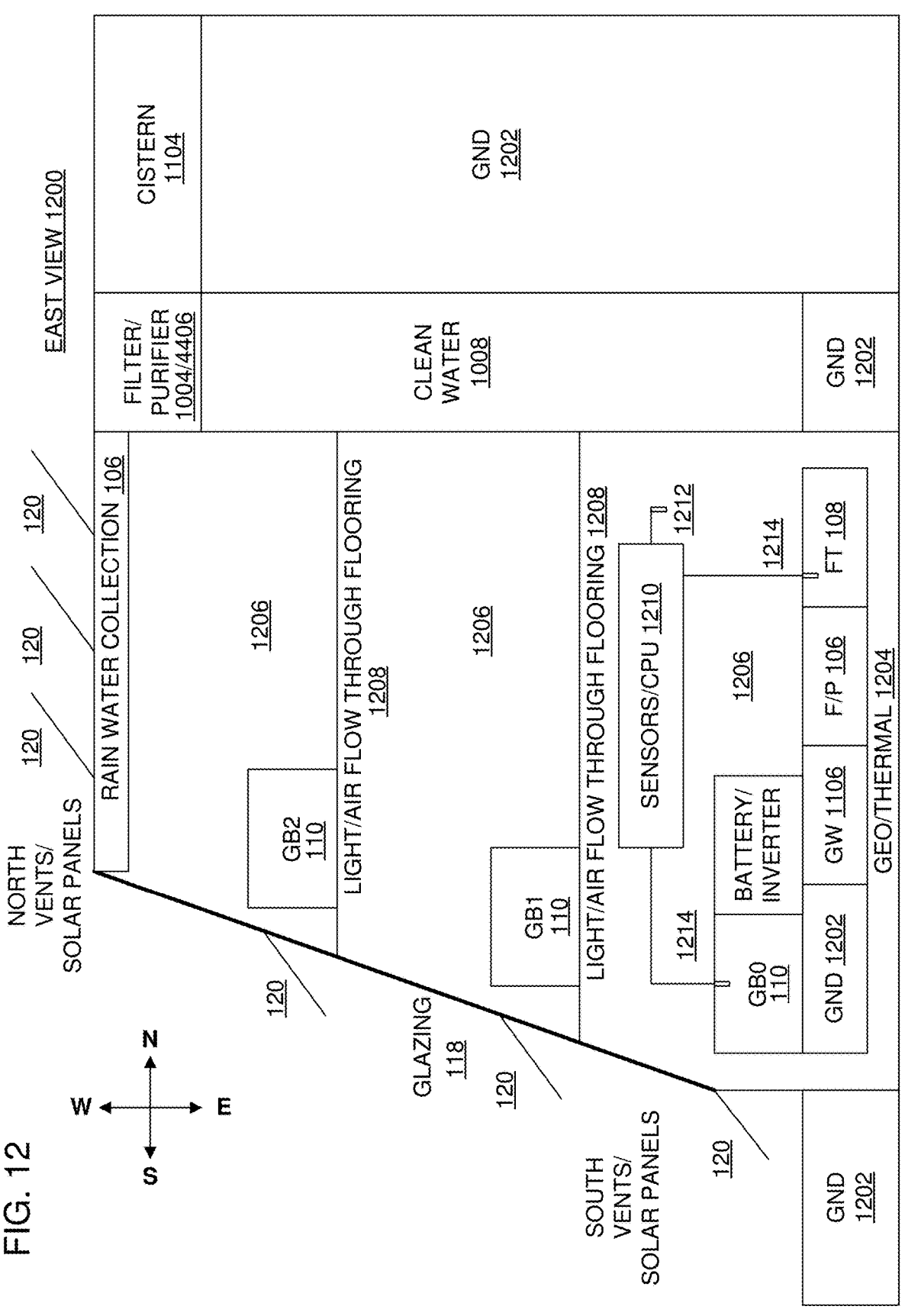

FIG. 12 is a diagram for a multi-level system version 1200 of the illustrative systems and methods for solar greenhouse aquaponics and black soldier fly (BSF) composter and auto fish feeder, and the like. In FIG. 12, the multi-level system version 1200 can be sheltered in the ground 1202 and/or insulated as previously described, and with geothermal heating and/or venting 1204. Each level 1206 separated by grated floors 1208 can include the grow beds 110 fed from the fish tank 108 via the hard filter 106 and with respective vents/solar panels 120 on the south side and north roof having RWC 106. A sensor/CPU system 1210 (e.g., spectral analyzer based, etc.) with gas 1212 and liquid 1214 probes can be used to measure and control all relevant air and water parameters (e.g., temperature, humidity, O2, CO2, H2O, dissolved oxygen, PH, nitrate, nitrite, ammonia, electrical conductivity (EC), etc.) of the fish tank 108 and grow beds 110 at every level 1206, as needed, including internet monitoring and control via suitable software applications, and the like. A battery and inverter system 1216 can be provided for on and/or off grid operation and switching from the solar panels 120 and/or wind turbine (not shown), including powering additional lighting (not shown), and the like.

Figure 13:
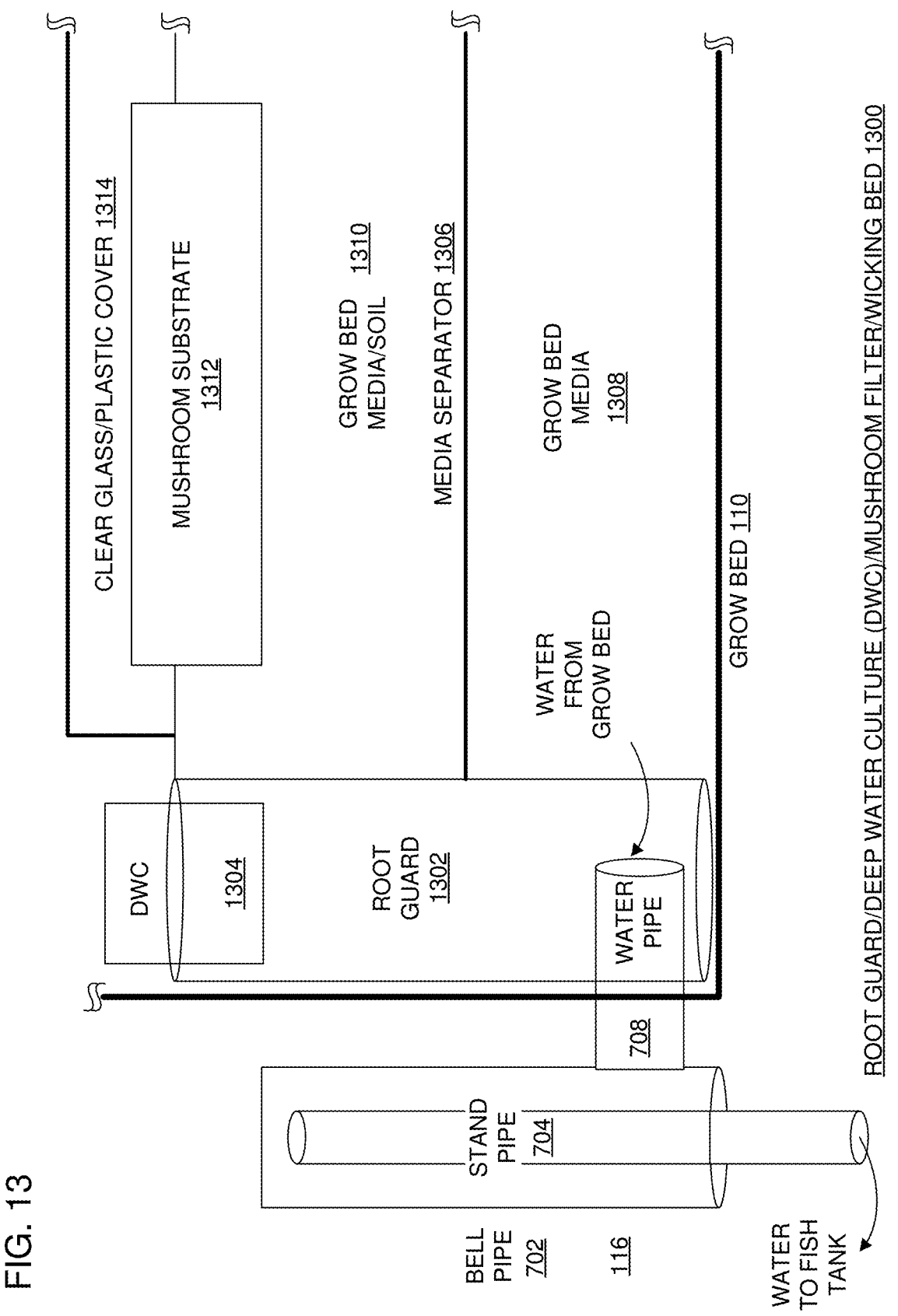

FIG. 13 is a diagram for additional features 1300 for the illustrative systems and methods for solar greenhouse aquaponics and black soldier fly (BSF) composter and auto fish feeder, and the like. In FIG. 13, the additional features 1300 can include a root guard 1302 for the bell siphon 116 for ease of cleaning and maintenance, and for providing deep water culture (DWC) functionality via a media filled net pot or a raft 1304 within the media bed grow bed 110. The grow bed 110 can also be configured a wicking bed by providing media separator 1306 (e.g., made of burlap or weed guard material, etc.) between hydroponic media 1308 and/or soil media 1310. A mushroom substrate 1312 with a clear glass or plastic cover 1314 can be placed in the media 1310 for growing edible mushrooms, advantageously, providing exchange of CO2 and O2, biological filtering of nitrates, an additional food source, and the like. The flood and drain action of the grow bed 110, advantageously, maintains humidity and provides air exchange, and the like, for mushroom cultivation, and the like.

Figure 14B:
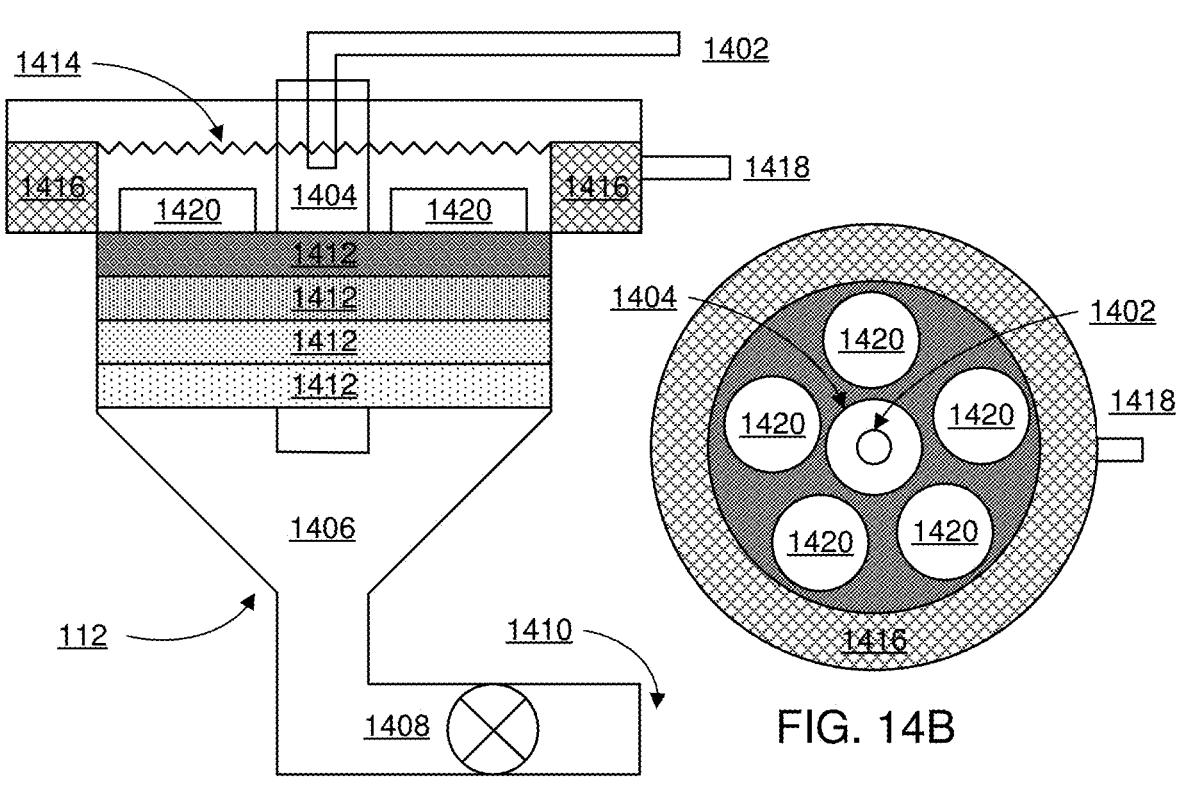

FIGS. 14A-14B is an illustrative hard filter employed in the systems and methods for solar greenhouse aquaponics and black soldier fly (BSF) composter and auto fish feeder of FIGS. 1-13. In FIGS. 14A-14B, the hard filter 112 can include a water inlet pipe 1402. The water inlet pipe 1402 can be fed with water from the fish tank 108 via a geyser pump or water pump (not shown) coupled to the fish tank 108. The input water from the water inlet pipe 1402 is fed to a stilling well 1404 that couples to a funnel-shaped settling chamber 1406. The funnel-shaped settling chamber 1406 is coupled to a valve 1408 coupled to an output drain pipe 1410 for purging fish waste that is settled in the settling chamber 1406. The water input from the water inlet pipe 1402 fills up in the settling chamber 1406 and then rises and passes through a series of one or more media filters 1412 (e.g., Matala® type advanced filter media) configured around the stilling well 1404, and starting from the bottom of the settling chamber 1406 with a coarse filter 1412 up to a fine filter 1412 near the top of the stilling well 1404. The water then rises and is filtered through the media filters 1412. The filtered water then enters a weir chamber 1414 having air stones 1420 resting on the top media filter 1412. The air stones 1420 provide for degassing of the filtered water in the weir chamber 1414. Around the weir chamber 1414 is provided a sponge type filter 1416 to further filter the water before the filtered water is output through an output pipe 1418 back to the fish tank 108 and/or grow beds 110. Water plants and algae (not shown), such as Duckweed, beneficial algae, and the like, can be grown in the filtered water in the weir chamber 1414 for further filtering of the water and for use as fish feed supplements. Advantageously, the algae grown in the weir chamber 1414 can include omega fatty acids typically missing from conventional farmed fish. Employing a geyser pump (not shown) to feed the water inlet pipe 1402, advantageously, allows for the system of FIGS. 1-14 to be run without employing any conventional water pumps, as with conventional aquaponics systems.

FIG. 15 is an illustrative geyser pump air distribution configuration employed in the systems and methods for solar greenhouse aquaponics and black soldier fly (BSF) composter and auto fish feeder of FIGS. 1-14 and 16-17. In FIG. 15, the geyser pump 114 air distribution configuration can include respective solar panels 1502 (and/or e.g., small wind turbines, not shown) and batteries 1504 coupled to the respective air pumps 606 for the respective grow beds 110 (not shown). The air pumps 106 are coupled to respective air tanks 1506 via one way valves 1508. The respective air tanks 1506 are coupled in series via respective pressure release valves 1510 configured for maintaining a suitable air pressure to power the respective geyser pumps 114. As the first air tank fills to pressure, the valves 1510 allow for filling of the subsequent air tanks 1506 until the last tank 1506 is full. When the air tanks 1506 are filled to capacity, the power to the air pumps 606 from the batteries 1504 can be turned off with a suitable air powered solenoid switch (not shown) and triggered by one or more of the respective pressure release valves 1510. Advantageously, such air distribution configuration allows for the system to be run solely from air and via solar power and/or wind power, and with N-way redundancy.

FIG. 16 is an illustrative rocket mass heater configuration employed in the systems and methods for solar greenhouse aquaponics and black soldier fly (BSF) composter and auto fish feeder of FIGS. 1-15 and 17. In FIG. 16, the rocket mass heater 104 configuration can include a rocket stove 1602 having an air feed 1608, fuel chamber 1606 and heated gas output 1610. The heated gas output 1610 is coupled to one or more suitable masses 1604 (e.g., cylindrical or square tube shaped clay flue pipes, etc.) coupled to each other via respective gas input and exhaust ports 1612 and 1614. The exhaust port of the final mass 1604 can be coupled to a gas exit pipe (not shown). Advantageously, the hot gasses from the gas output 1610 of the rocket stove 1602 enter the first mass 1604 and rise, and then exit when cooled down from a lower portion thereof via the first gas output 1612 coupled to the second mass 1604, and so on, to efficiently heat each of the masses 1604 with cooler and cooler gasses in series.

FIG. 17 is an illustrative on-demand aquaponics or hydroponics configuration employed in the systems and methods for solar greenhouse aquaponics and black soldier fly (BSF) composter and auto fish feeder of FIGS. 1-16. In FIG. 17, the on-demand aquaponics or hydroponics configuration 1700 can include respective hydroponics tanks 1702 having respective geyser pumps 1704 therein for pumping hydroponic water from the tanks 1702 to the respective grow beds 110 that can also be fed with water from the fish tank 108 via the respective geyser pumps 114. Respective air switches 1706 allow for selection of air to be delivered to the respective geyser pumps 1704 and/or 114. The respective output water from the grow beds 110 can be cycled back to the respective hydroponics tanks 1702 and/or the fish tank 108 via respective selector valves 1708 and 1710. Advantageously, each of the grow beds 110 can be configured to cycle water from the fish tank 108 and/or the respective hydroponics tanks 1702. Such a configuration, advantageously, allows for cycling of, for example, high nitrate fish tank 108 water to one or more of the grow beds 110 for vegetative growth by sending air to only one or more of the geyser pumps 114 via suitable configuration of the respective air switches 1706 and the respective selector valves 1708 and 1710. After a desired vegetative growth stage is complete in one or more of the grow beds 110, cycling of, for example, low nitrate, high phosphorous and potassium, and the like, hydroponics tanks 1702 water to one or more of the grow beds 110 for flower and fruiting growth can be accomplished by sending air to only one or more of the geyser pumps 1704 via suitable configuration of the respective air switches 1706 and the respective selector valves 1708 and 1710. Advantageously, plants that require high nitrates and/or plants that require low nitrates and high phosphorous and potassium, and the like, can be accommodated in one or more of the respective grow beds 110 with suitable configuration of the respective air switches 1706 and the respective selector valves 1708 and 1710.

Figure 18:
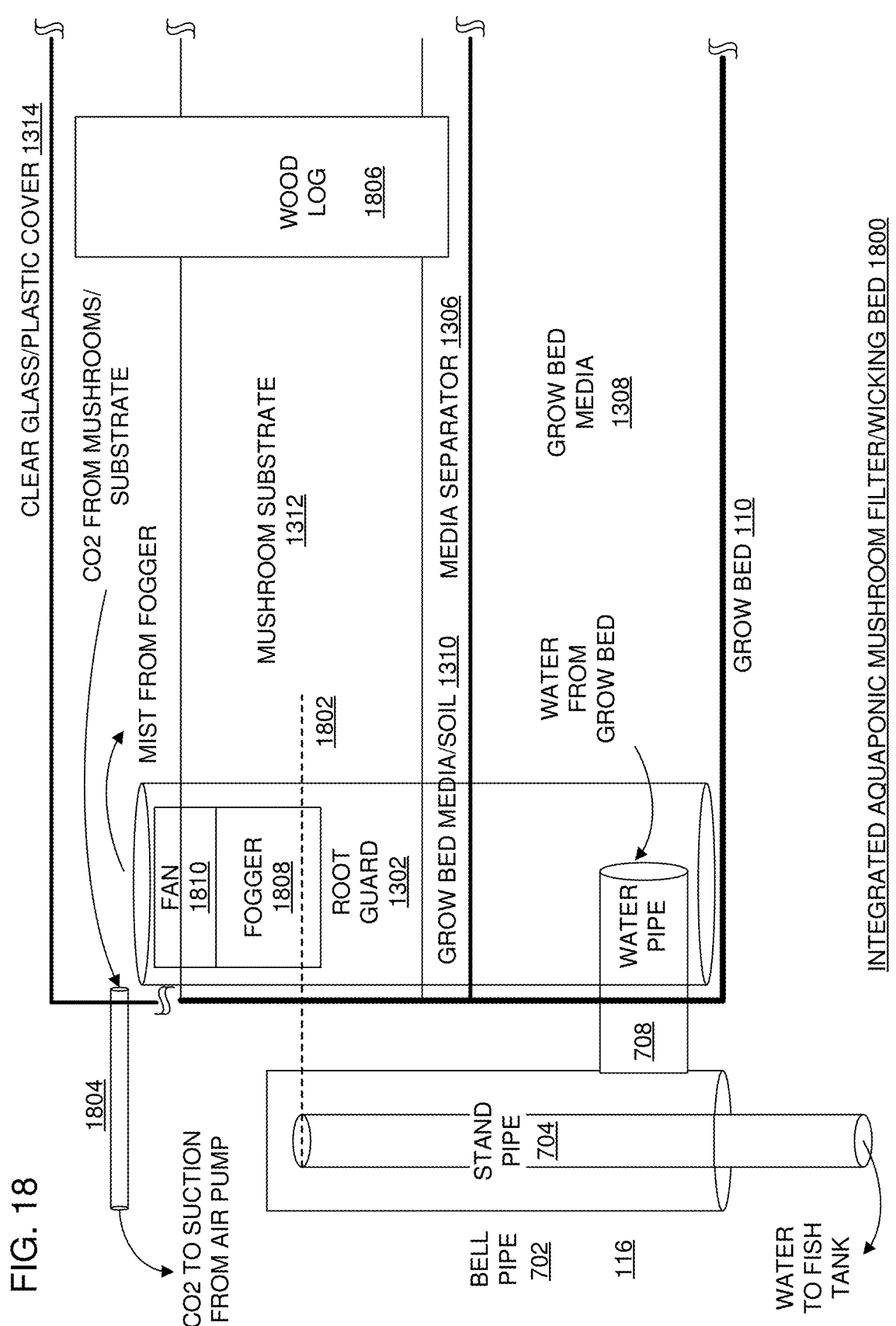
FIG. 18 is an illustrative aquaponic mushroom filter and wicking bed configuration employed in the systems and methods for solar greenhouse aquaponics and black soldier fly (BSF) composter and auto fish feeder.

FIG. 18 is an illustrative aquaponic mushroom filter and wicking bed configuration employed in the systems and methods for solar greenhouse aquaponics and black soldier fly (BSF) composter and auto fish feeder of FIGS. 1-17 and 19-21. In FIG. 18, the mushroom substrate 1312 is included over the media separator 1306, such that the bell siphon 116 floods and drains the mushroom substrate 1312 up to a water level 1802 determined by the standpipe 704. In this way, the mushroom substrate 1312 can be hydrated to increase fruiting, in addition to adding beneficial microbes, during flood and drain cycles, advantageously, increasing mushroom fruit production. Advantageously, the mushroom substrate 1312 can be inoculated and colonized directly in the flood and drain media grow bed 110. During the colonization stage, the flood and drain action is turned off, for example, by turning off the air supply to the geyser pump that feeds the grow bed 110, so that the mycelium can fully colonize the mushroom substrate 1312. After the mushroom substrate 1312 is fully colonized, the flood and drain mechanism can be turned back on, so is to hydrate the mushroom substrate 1312 for increased fruiting, as previously described. In addition, the water from the fish tank can include around 1-2 parts per thousand of salt for the fish health, and which also acts as an antibacterial agent to reduce contamination of the mushroom substrate 1312.

Advantageously, since the system can be fully air powered, the suction from the air pumps used to power the geyser pumps can be used to extract CO2 from the mushroom substrate 1312 and mushroom fruits, thereby increasing fresh air exchange, and producing mushroom fruits with desirable characteristics. In addition, the CO2 that is extracted from the mushroom substrate 1312 and mushroom fruits can be used by the algae and duckweed biofilter, previously described, for example, with respect to FIG. 14B, to create a closed loop system where the CO2 from the mushrooms is employed by the algae and duckweed biofilter of FIG. 14B.

In further embodiments, a wood log or block 1806 that is inoculated with dowels colonized with mushroom mycelium can be inserted inside of the media of the grow bed 110 to create a natural log type mushroom cultivation system. Advantageously, plants can also be grown within the grow bed 110 for providing oxygen and carbon dioxide exchange between the plants and the mushroom logs 1806 and/or mushroom substrate 1312, and the mushrooms growing thereon.

In further embodiments, a fogger 1808 (e.g., of the ultrasonic type, etc.) with a fan 1810 can be positioned within the root guard 1302, such that when the root guard 1302 fills with water during flood and drain cycles, fog is created that is then distributed via the fan 1810 to the mushroom substrate 1312 or the logs 1803 and the mushrooms growing thereon, advantageously, increasing fresh air exchange.

Figure 19:
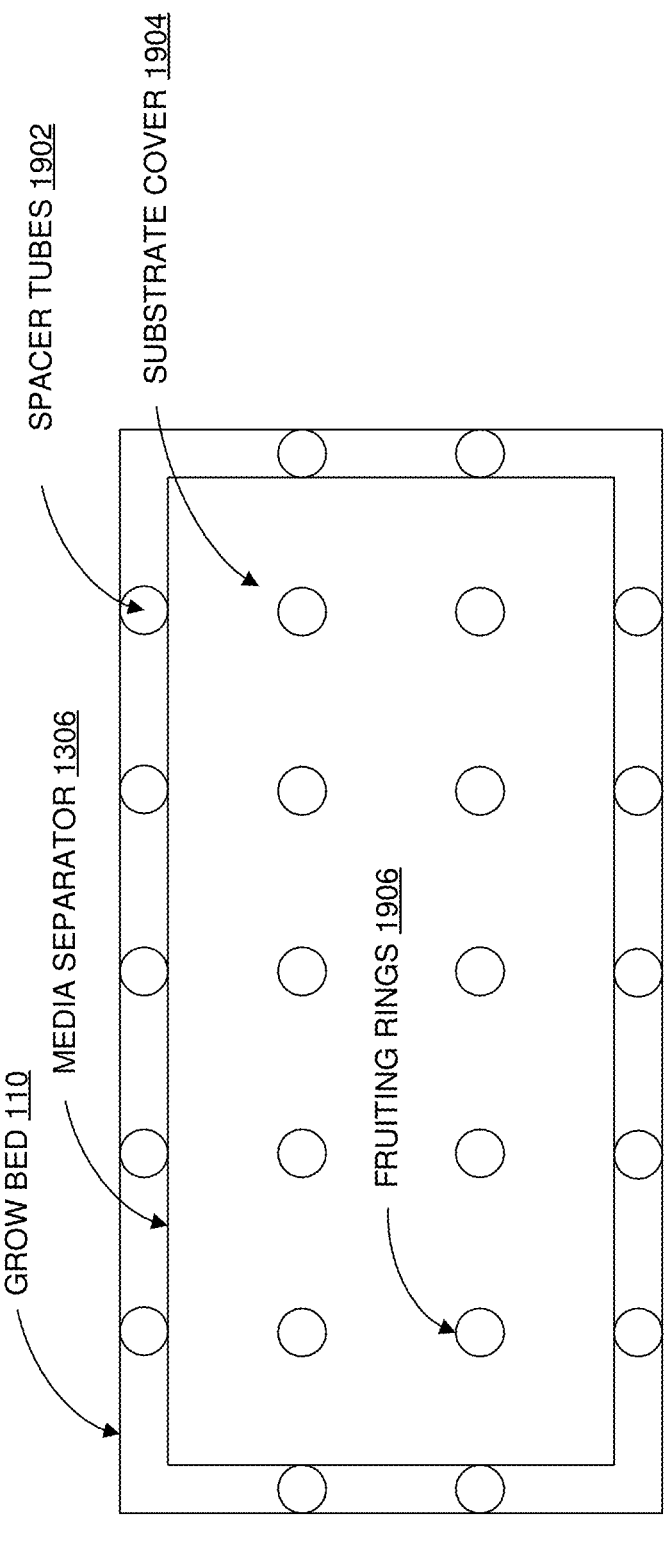
FIG. 19 is an illustrative aquaponic mushroom filter and wicking bed configuration employed in the systems and methods for solar greenhouse aquaponics and black soldier fly (BSF) composter and auto fish feeder.

FIG. 19 is an illustrative aquaponic mushroom filter and wicking bed configuration employed in the systems and methods for solar greenhouse aquaponics and black soldier fly (BSF) composter and auto fish feeder of FIGS. 1-18 and 20-21. In FIG. 19, spacer tubes 1902 are positioned between the media separator 1306 and the grow bed walls so is to create spaces around the mushroom substrate in the flood and drain media grow bed 110. Advantageously, this can increase the amount of air that is drawn around the mushroom substrate during the flood and drain action.

In addition, a substrate cover 1904, for example, made for a plastic material that does not transmit light can be sealed over top of the substrate, so as to maintain moisture in the substrate during the fruiting stages. Fruiting rings 1906 can be disposed within the substrate cover 1904 to provide points for mushroom fruiting dispersed along the entire substrate. Advantageously, the sizes of the mushroom flushes can be adjusted based on the number of fruiting rings 1906 employed within the substrate cover 1904. The fruiting rings 1906 can be positioned within the substrate cover 1904, and covered with a suitable filter material, for example, micropore type tape, polyfill, and the like, to reduce contamination, while allowing for fresh air exchange.

Figures 20A, 20B:
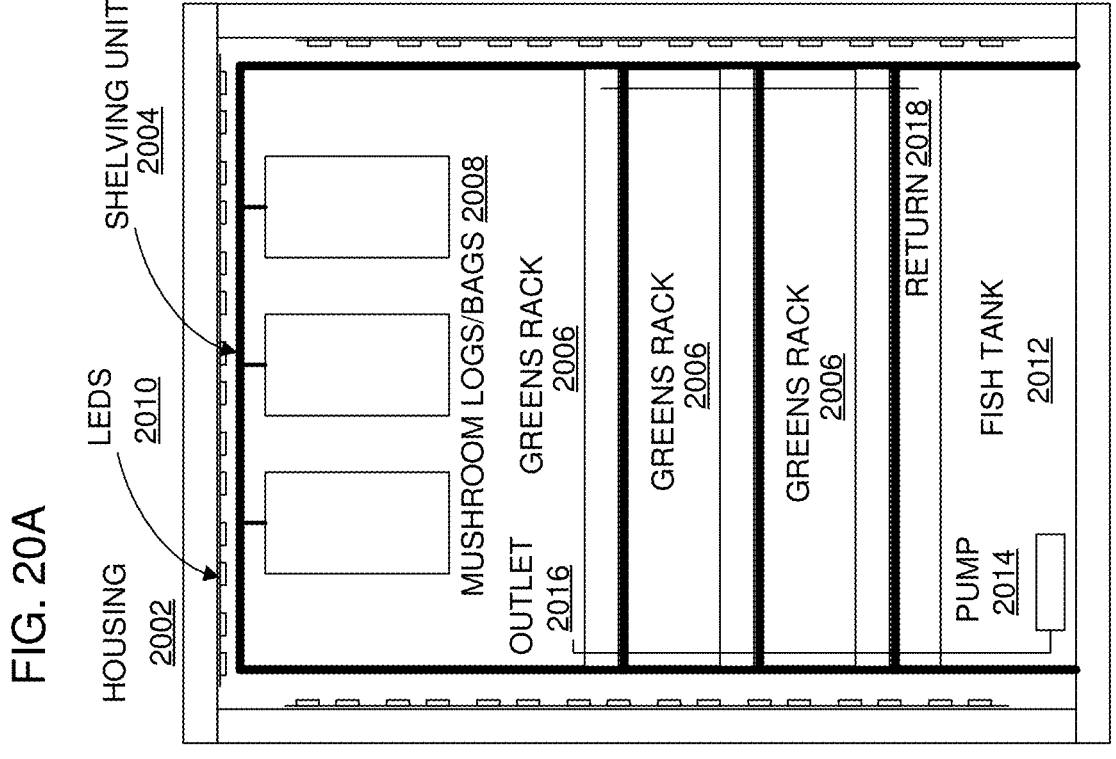
FIGS. 20A-20B are illustrative mushrooms and greens fruiting chamber configurations employed in the systems and methods for solar greenhouse aquaponics and black soldier fly (BSF) composter and auto fish feeder.

FIGS. 20A-20B are illustrative mushrooms and greens fruiting chamber configurations employed in the systems and methods for solar greenhouse aquaponics and black soldier fly (BSF) composter and auto fish feeder of FIGS. 1-19 and 21. In FIGS. 20A-20B, an insulated housing enclosure 2002 is provided with a shelving unit 2004, for example, of the type of shelving units used in restaurants, and the like. The shelving unit 2004 can include racks 2006 that can be configured for growing microgreens, edible plants, and the like.

The microgreens racks 2006 can be positioned in a lower portion of the shelving unit 2004, with mushroom logs or bags 2008 suspended in an upper portion of the shelving unit 2004. Advantageously, the CO2 produced by the mushroom logs and/or bags 2008 and/or mushrooms growing thereon, settles to the bottom of the shelving unit 2004 and is employed by the plants in the greens racks 2006. Similarly, the plant racks 2006 provide oxygen to the mushroom logs or bags 2008. Advantageously, air exchange and humidity can be maintained with such configuration so that humidifiers, fans, and the like, need not be employed.

Lights 2010 (e.g., LED type lights, grow lights, etc.) and the like, can be disposed within the housing 2002 and or the shelving unit 2004 to provide light for the plants in the greens rack 2006 and for the mushrooms growing on the logs or bags 2008. In further embodiments, and aquaponics type fish tank 2012 with a water or geyser type pump 2014 can be used to distribute nutrient rich water from the fish tank 2012 to the greens racks 2006 via the outlet 2018. A return line 2018 can return the filtered water from the greens racks 2006 back to the fish tank 2012. Advantageously, the humidity provided by the aquaponics component can be used to increase the humidity within the mushroom and greens fruiting chamber 2000, for improved plant and mushroom growth.

In FIG. 20B, the mushroom logs or bags 2008 can be placed on mushroom racks 2020, instead of or in addition to being hung from the shelving unit 2004, as shown in FIG. 20A. Advantageously, the racks 2006 and 2020, can be configured as conventional restaurant racks to allow for easy filling and removal of the mushrooms and plants, for example, in a restaurant type setting, and like. In further embodiments, fish tank 2012 need not be employed, wherein nutrient rich water from the fish tank 108 and/or one or more of the hydroponic tanks 1702 can be fed to the racks 2006 with the return 2018 coupled back to return the filtered water to the fish tank 108 and/or one or more of the hydroponic tanks 1702.

Figure 21:
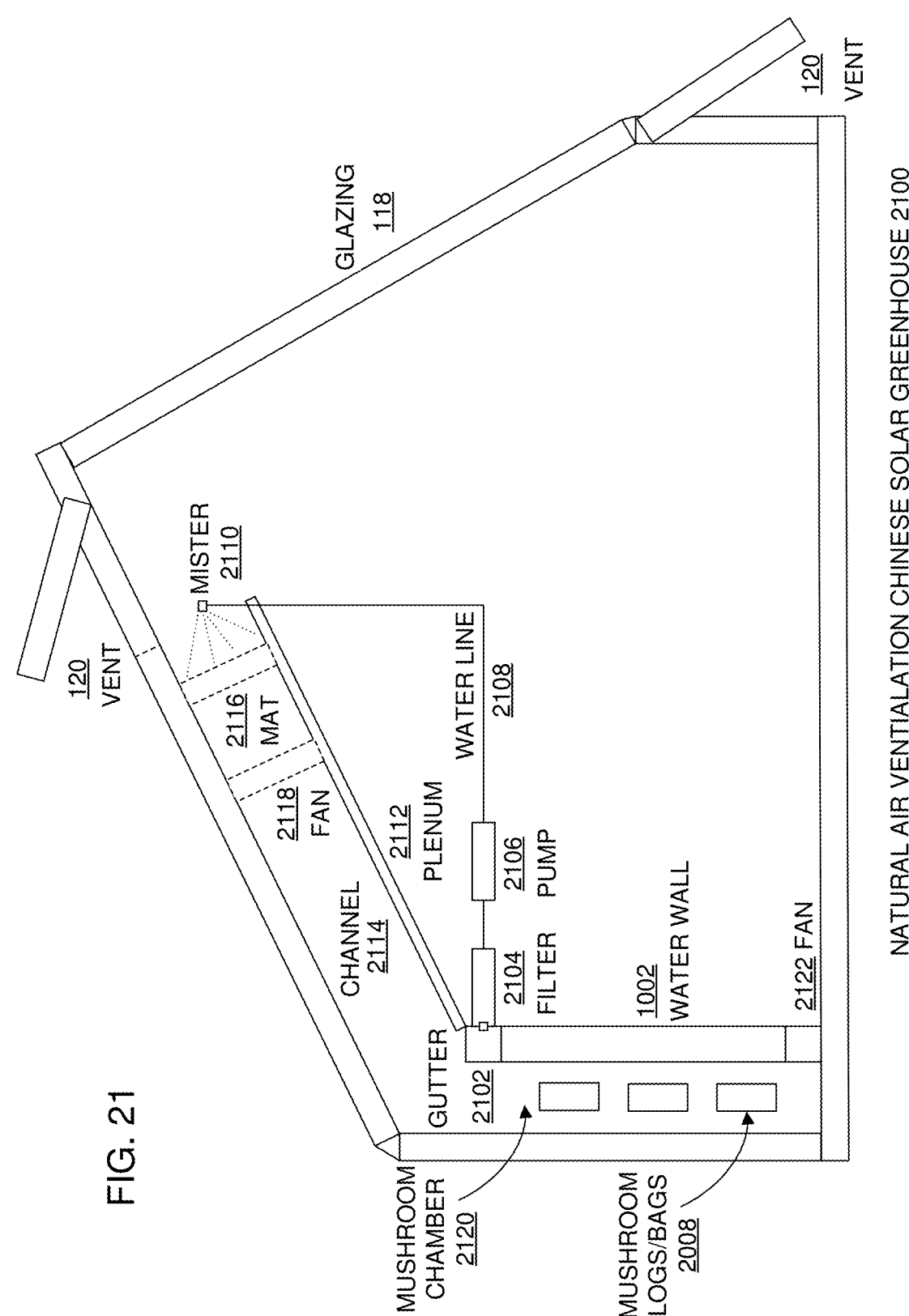
FIG. 21 is an illustrative solar greenhouse with a natural air ventilation configuration employed in the systems and methods for solar greenhouse aquaponics and black soldier fly (BSF) composter and auto fish feeder.

FIG. 21 is an illustrative solar greenhouse with a natural air ventilation configuration employed in the systems and methods for solar greenhouse aquaponics and black soldier fly (BSF) composter and auto fish feeder of FIGS. 1-20. In FIG. 21, a reservoir or gutter 2102 feeds water to a prefilter 2104 connected to a pump 2106 which supplies pressured water to a mister head 2110 via a water line 2108. The pressurized water from the pump 2106 provides a fine mist from the mister 2110 that is transmitted down to channel formed by a plenum or secondary roof 2112 that is underneath the north roof of the greenhouse. The channel 2114 that is formed, advantageously, produces a cold stream of air as the water that is misted condenses, thus, creating a natural air flow that flows down the channel to 2114 towards the bottom of the greenhouse.

Water that condenses from the mister 2110 is captured by the plenum 2112 and fed back to the gutter 2102 to be recycled and delivered back through the filter 2104 to the pump 2106 and the water line 2108 to the mister 2110. In further embodiments, a straw or similar material, and the like, type mat 2116 can be disposed in front of the mister 2110 with a fan 2118 drawing air through the mat 2116 to produce a swamp cooler, and the like, type effect within the channel 2114.

The cold air flowing through the channel 2114, can flow into a mushroom chamber 2120 with mushroom logs or bags 2008 disposed within the mushroom chamber 2120. Advantageously, the mushroom chamber 2120 can be located behind the water wall 1002 of the Chinese solar greenhouse. The cold air flowing down to channel 2114 into the mushroom chamber 2120, advantageously, can draw the carbon dioxide from the mushroom logs or bags 2008 towards the bottom of the greenhouse to be recycled by the plants on the other side of the water wall 1002 in a plant chamber 2124. A fan 2122 can be provided, if needed, to further enhance the $CO_2$ and $O_2$ exchange from the mushroom chamber 2120 into the plant section of the greenhouse.

Advantageously, the cold air flowing through the channel 2114 and the mushroom chamber 2120, creates a natural circular circulation pattern, as the air cools and then is heated and rises in the plant chamber 2124 and is expelled through the upper vent 120. The lower vent 120 also can introduce fresh cold air into the system and further helping the air circulate with the carbon dioxide in a circular pattern within the greenhouse. As with the previous embodiments, advantageously, $CO_2$ and $O_2$ gas exchange is provided to benefit both the plants and the mushrooms being cultivated. In further embodiments, one or more of the grow beds 110 configured for growing mushrooms, as previously described, can be located behind the water wall 1002 in the mushroom chamber 2120.

Figure 22:
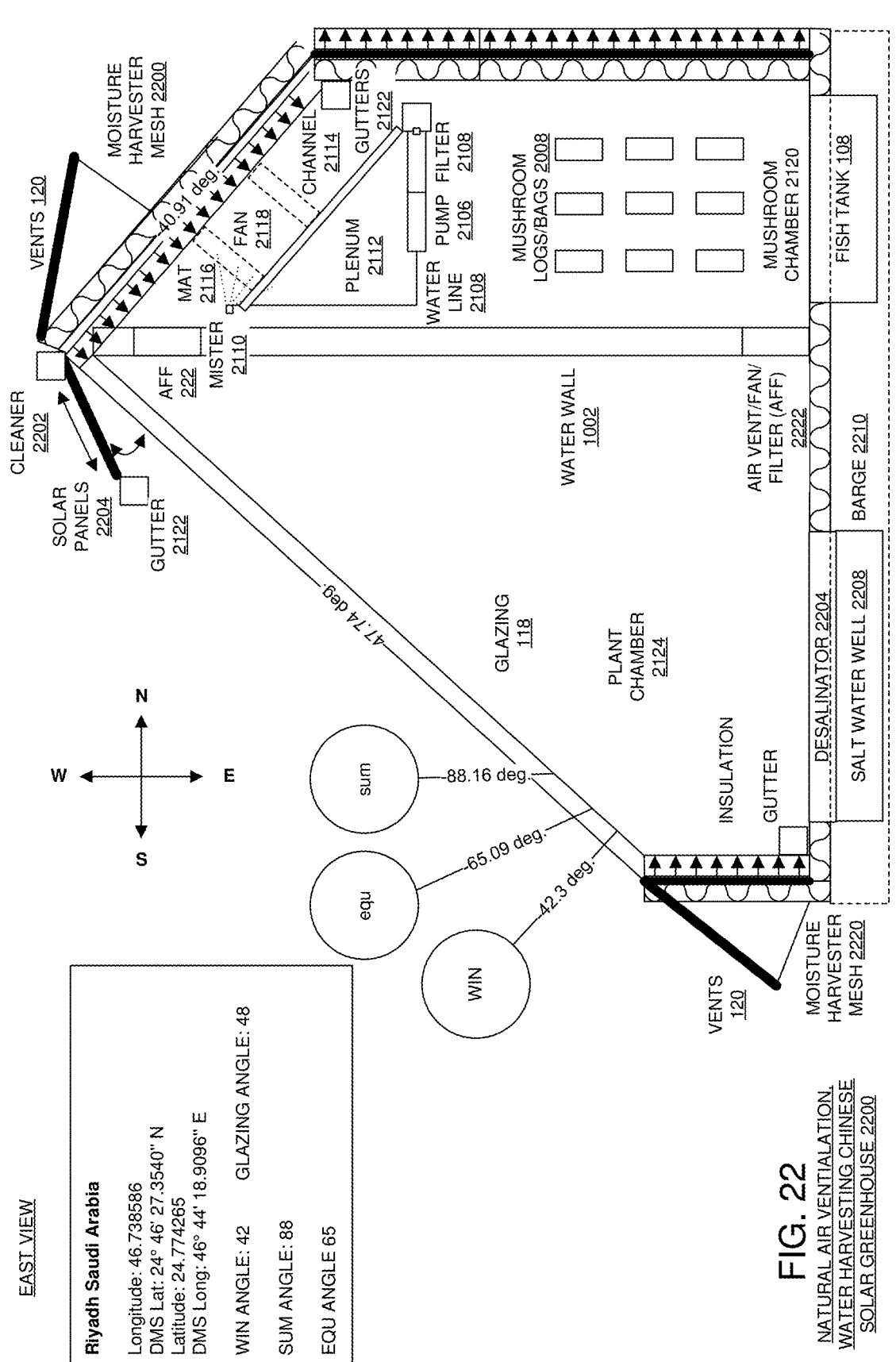
FIG. 22 is an illustrative solar greenhouse with natural air ventilation and water harvesting configurations suited for desert and seasteading applications employed in the systems and methods for solar greenhouse aquaponics and black soldier fly (BSF) composter and auto fish feeder.

FIG. 22 is an illustrative solar greenhouse with natural air ventilation and water harvesting configurations suited for desert and seasteading applications employed in the systems and methods for solar greenhouse aquaponics and black soldier fly (BSF) composter and auto fish feeder of FIGS. 1-21. In FIG. 22, moisture and/or fog harvesting meshes 2220, as are known in the relevant art(s), and the like, are disposed on openings of vents 120, and so as to capture internal moisture, external fog, and the like. The captured water is then fed to various gutters 2122, and can be filtered, as needed, for supplying fresh water to the fish tank 108, watering plants in the plant chamber 2124, providing water for the water wall 1002, providing drinking water, and the like. The gutters 2122 also can be used to harvest water used to clean solar panels 2202 disposed on the roof of the greenhouse, by a solar panel cleaning device 2202, as are known in the relevant art(s), and that, for example, moves across and sprays water over the solar panels 2204 to clean dust therefrom. Air vents, filters, and/or fans 2222, and the like, are used to filter and/or push $O_2$ from the plant chamber 2124 into the mushroom chamber 2120 from the top of the greenhouse, and for expelling $CO_2$ and filtering spores from the mushroom chamber 2120 into the plant chamber 2124 at the bottom of the greenhouse. Advantageously, the fish tank 108 can be located on the cooler side of the water wall 1002 under the mushroom chamber 2120.

The glazing 118, for example, is shown configured at an angle suitable for the latitude of Riyadh, Saudi Arabia. A saltwater well 2208 can be disposed underneath the greenhouse under the plant chamber 2124 for generating desalinated water via a disalinator device 2204 and/or any other suitable passive or active water desalination technologies, such as evaporation, solar still action, membranes, wicking methods, and the like. The greenhouse can be disposed over a barge 2210 for seasteading applications, and the like. Accordingly, the above configurations are advantageous for desert, high dust environments, seasteading applications, beach front applications, and the like.

Figures 23A, 23B:
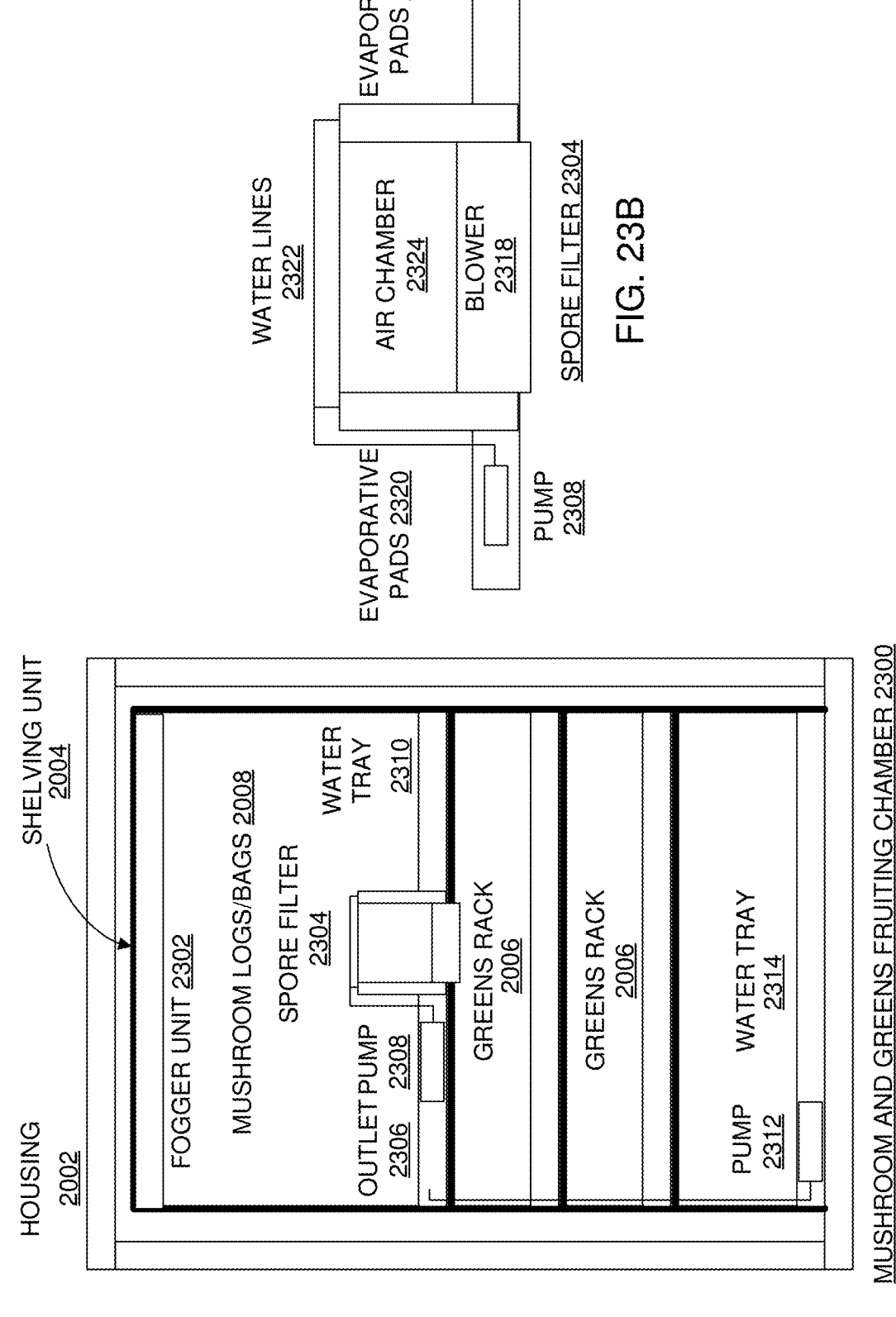
FIGS. 23A-23B are illustrative mushrooms and greens fruiting chamber with spore filtering configurations employed in the systems and methods for solar greenhouse aquaponics and black soldier fly (BSF) composter and auto fish feeder.

FIGS. 23A-23B are illustrative mushrooms and greens fruiting chamber with spore filtering configurations employed in the systems and methods for solar greenhouse aquaponics and black soldier fly (BSF) composter and auto fish feeder of FIGS. 1-22. In FIGS. 23A-23B, a fogger and fresh air input unit 2302 (e.g., ultrasonic-based, Natura Air Ventilation (NAV)-based, etc.) is disposed over the mushroom logs or bags 2008 to maintain suitable humidity levels. A spore filter 2304 is disposed below the mushroom logs or bags 2008 and above the greens racks 2006 for filtering spores from the mushroom logs or bags 2008, and pushing the filtered air and $CO_2$ into the greens racks 2006. A water tray 2314 captures moisture from the greens racks 2006 and from the moist air generated by the fogger 2302. A pump 2312 pumps the harvested water via outlet 2306 to the spore filter 2304, which includes a water tray 2310 for collecting spores, a pump 2308 for pumping water over evaporative pads 2320 via water lines 2322, a blower 2318 configured to draw air from the fogger and fresh air input unit 2302 and $CO_2$ generated by the mushroom logs or bags 2008 through evaporative pads 2320 into air chamber 2324, and then into the greens racks 2006. Advantageously, the $O_2$ and humidity generated by the greens racks 2006 also can be directed to the fogger and fresh air input unit 2302 to provide the $O_2$ and humidity to the mushroom logs or bags 2008.

FIGS. 24-37 are used to illustrate passive solar houses, buildings, and skyscrapers systems employing aquaponics and greenhouse technologies with natural air ventilation suited for extreme desert, extreme cold, and space environments, employed with the systems and methods for solar greenhouse aquaponics and black soldier fly (BSF) composter and auto fish feeder of FIGS. 1-23 and 38-43. The embodiments of FIGS. 24-37 can employ similar features that function in a similar manner as any of the features from the embodiments of FIGS. 1-23 and 38-43, and which will not be further described for the sake of brevity.

Figure 24:
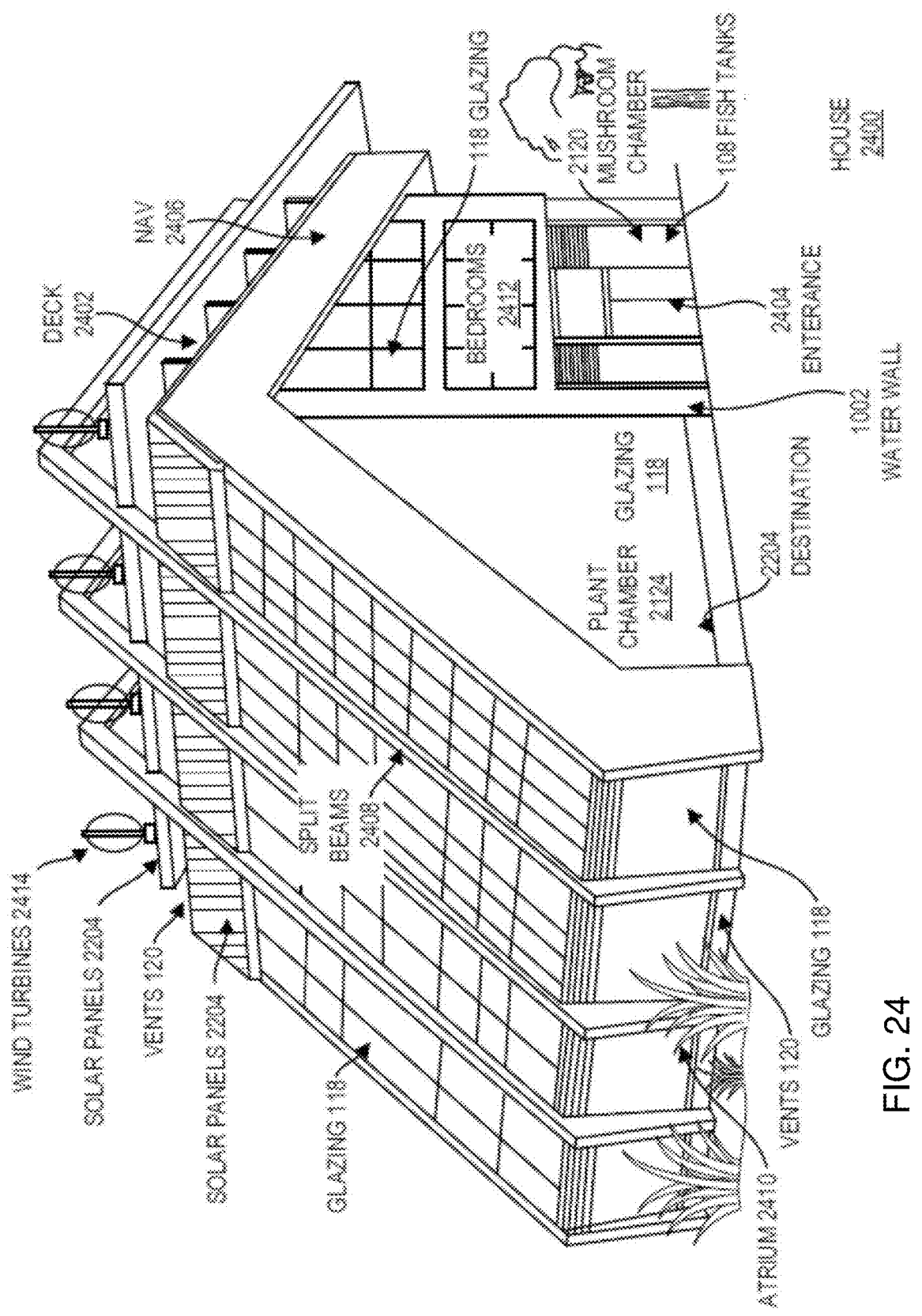

In FIG. 24, a passive solar house system 2400 can include the water wall the 1002, the vents 120, the solar panels 2204, the glazing 118, the plant chamber 2124, the fish tanks 108, the mushroom chamber 2120, and the desalination system 2204, the natural air ventilation system 2406, the water harvesting gutter system, as previously described, the aquaponics system, as previously described, and the like, and that function in a similar manner as the respective features from the embodiments of FIGS. 1-23. The passive solar house system 2400 further includes a deck 2402, one or more entrances 2404, split beams 2408, an atrium 2410 located on the sun facing side of the water wall the 1002, bedrooms 2412 located on shaded side of the water wall the 1002, and wind turbines 2414, and the like, on the roof of the house.

Advantageously, the natural air ventilation system 2406 allows for cycling of CO2 produced by fish, mushrooms, animals, humans, and the like, in the shaded side of water wall 1002, and the O2 produced by plants, trees, vegetation, and the like, in the sun facing side of water wall 1002. The solar panels 2204 on the upper deck 2402 can be configured to be adjustable to maximize sun exposure and shading of the deck 2402, as needed. The desalination system 2204 can be employed in order to fill the water wall 1002 and the fish tanks 108 and provide fresh water for inhabitants, for example, in desert, space, extreme cold, and the like, environments, where saltwater is available. The water harvesting gutter system, as previously described, the aquaponics system, as previously described, and the like, can be employed to maximize water reusage, and the like. The split beams 2408 can be employed as a design feature within the house and the deck 2402 and for hanging lighting fixtures, and the like, as needed.

Figure 25:
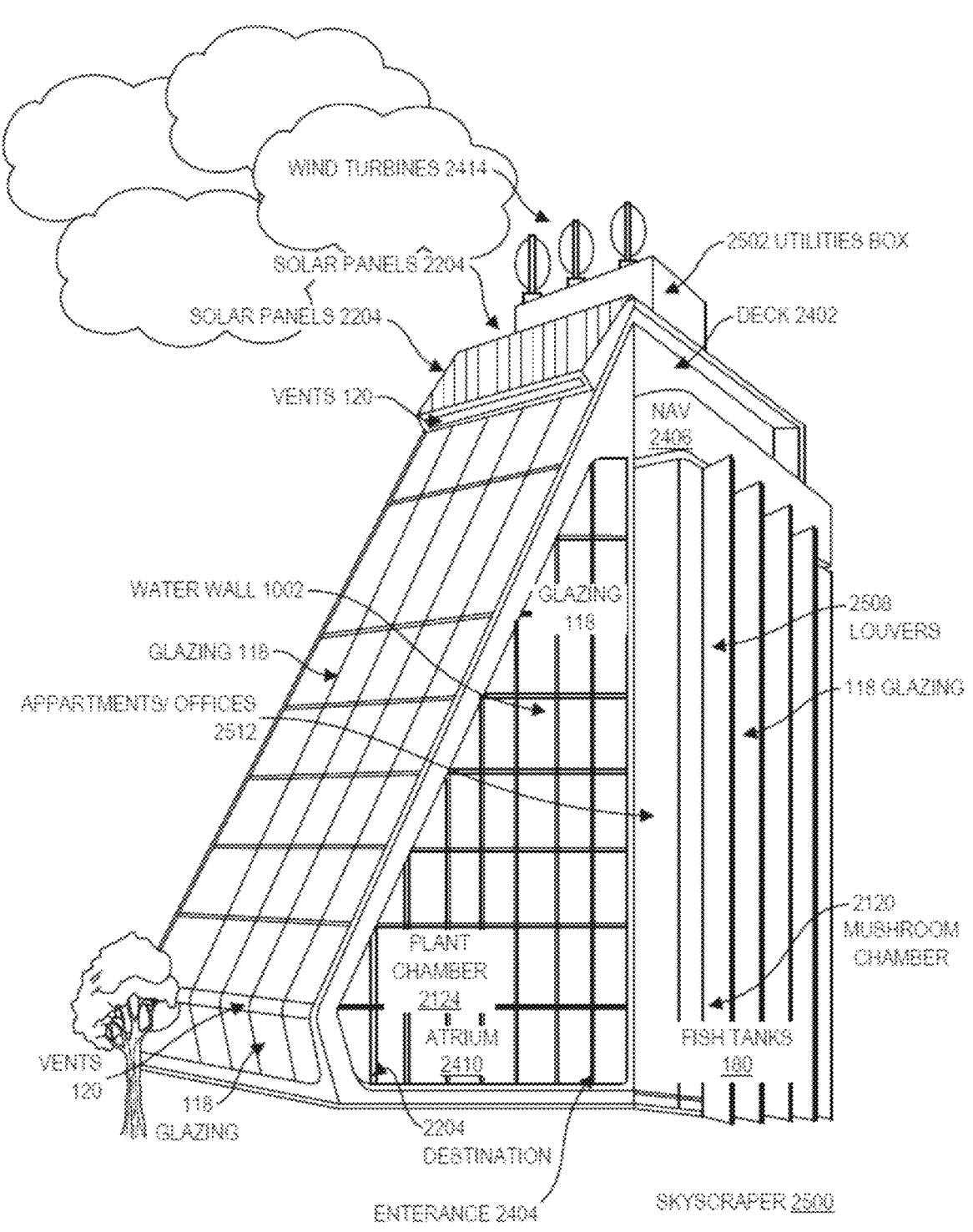

In FIG. 25, a passive solar building or skyscraper system 2500 can include the features previously described with respect to FIG. 24. Advantageously, the passive solar building or skyscraper system 2500 further includes louvers 2508 on the sides of the structure to provide adjustable shade and light to apartments, shops, offices, and the like, 2512 located on the shade side of the water wall 1002. A utilities box 2502, and the like, also is provided to house utility, wind, solar, and the like equipment.

Figure 26A:
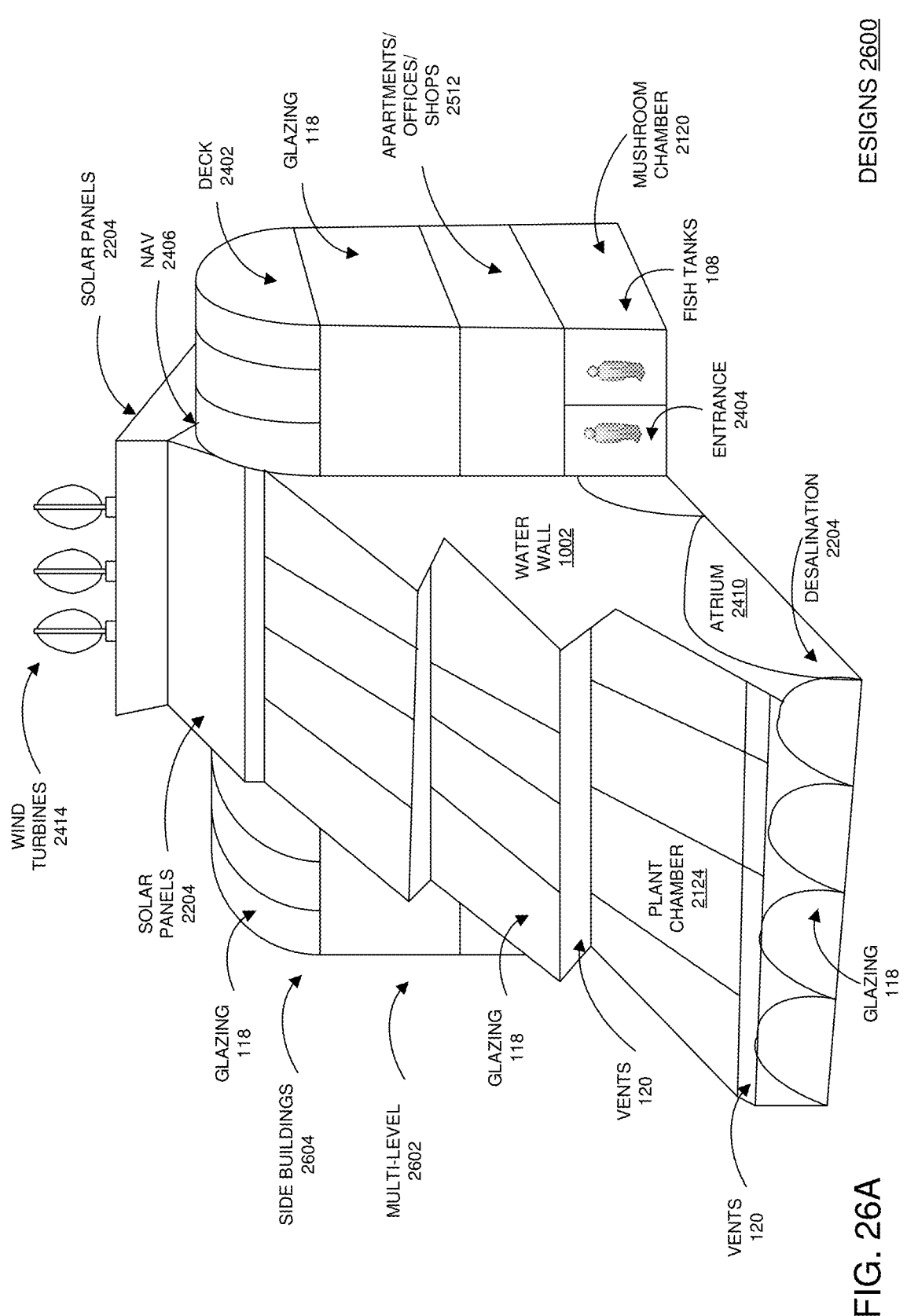

In FIGS. 26A-26B, a passive solar building or skyscraper system 2600 can include the features previously described with respect to FIGS. 24-25. In FIG. 26A, advantageously, the passive solar building or skyscraper system 2600 further includes a multi-level 2602 design with side buildings 2604, and the like. The multi-level 2602 design also can be used to maximize the space, and the like, of the atrium 2410. In FIG. 26B, advantageously, the passive solar building or skyscraper system 2600 further includes multi-level shops 2606 in an open atrium 2410 design, and the like, featuring the massive water wall 1002 as a design component.

Figure 27A:
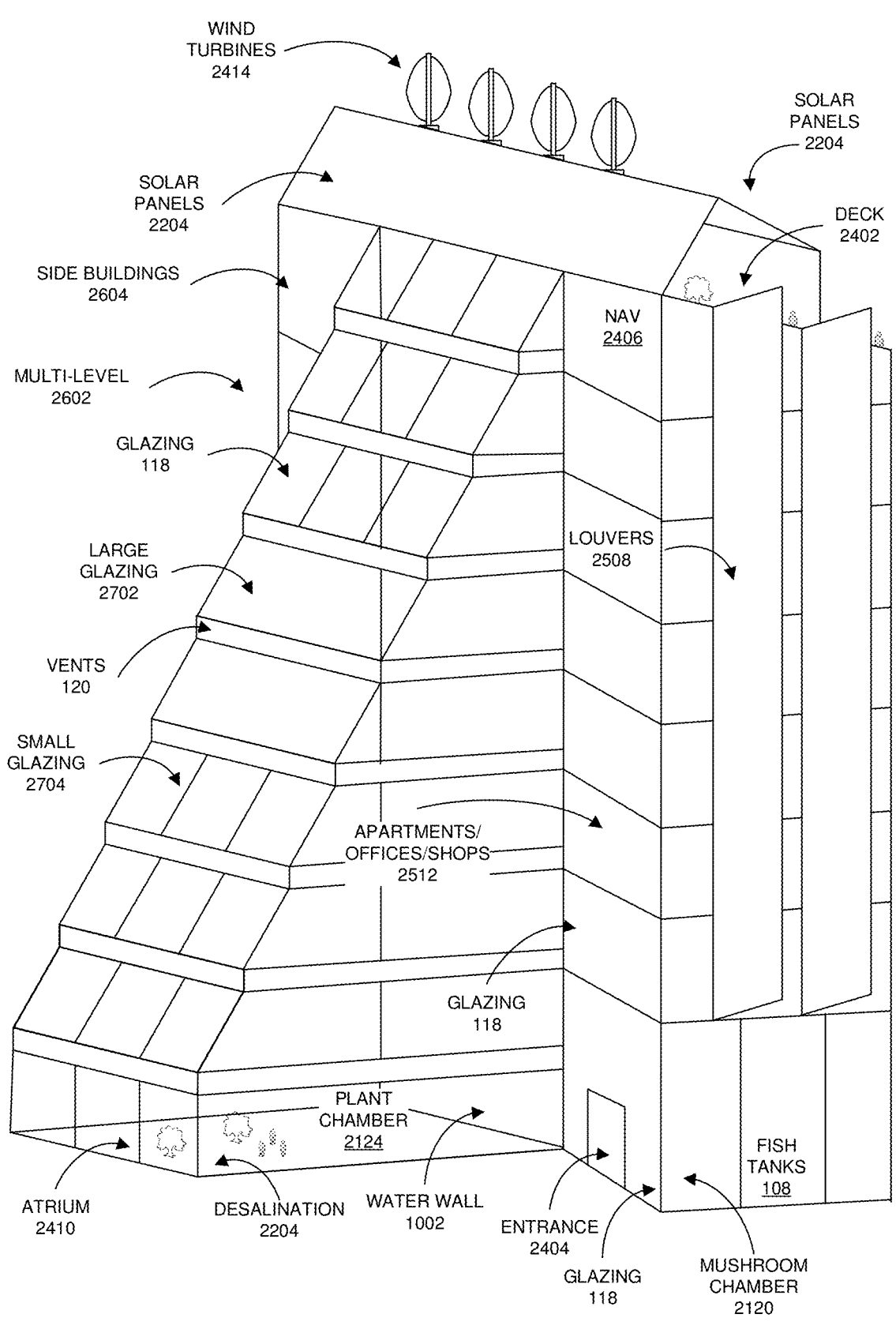
Figure 27B:
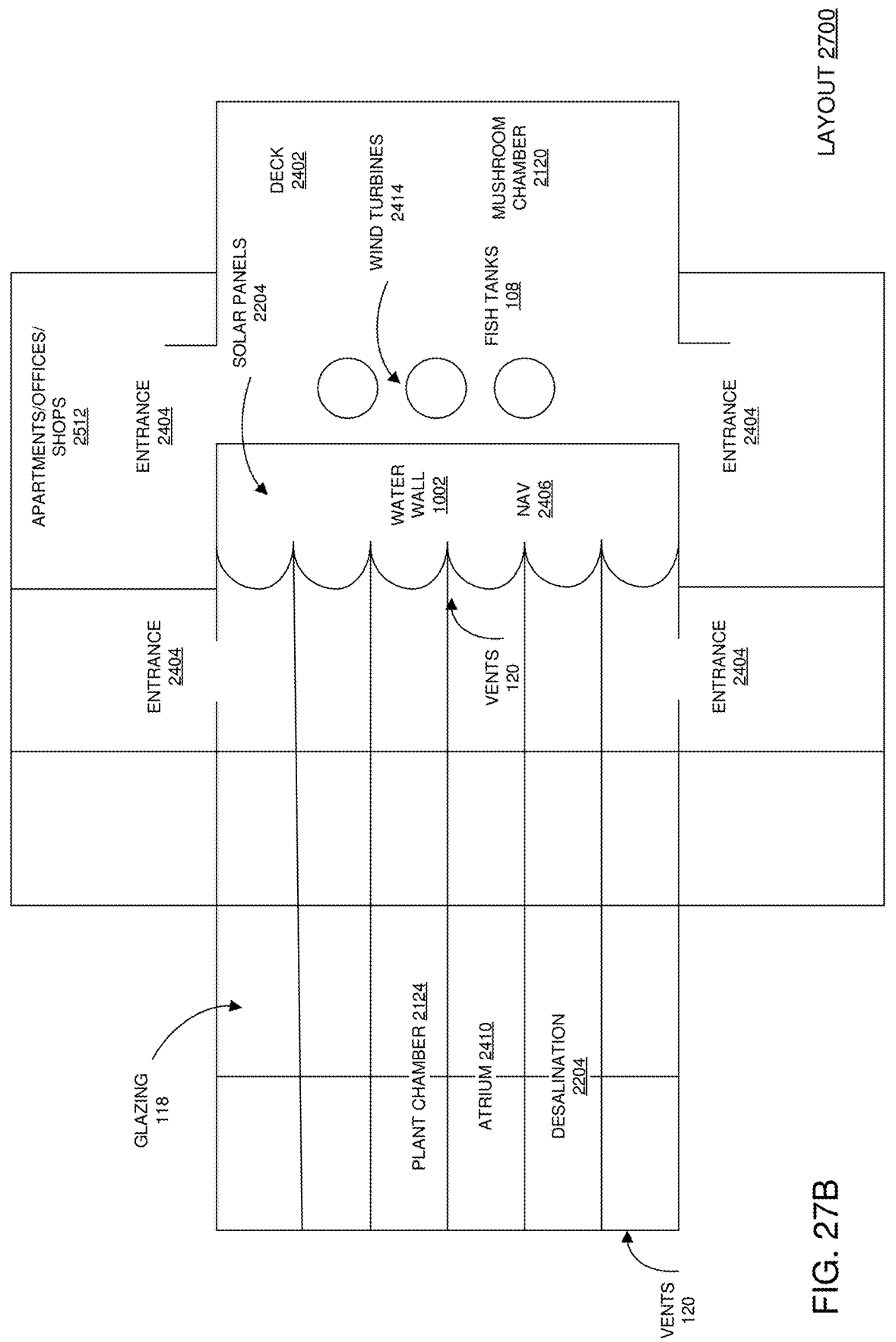
Figure 27C:
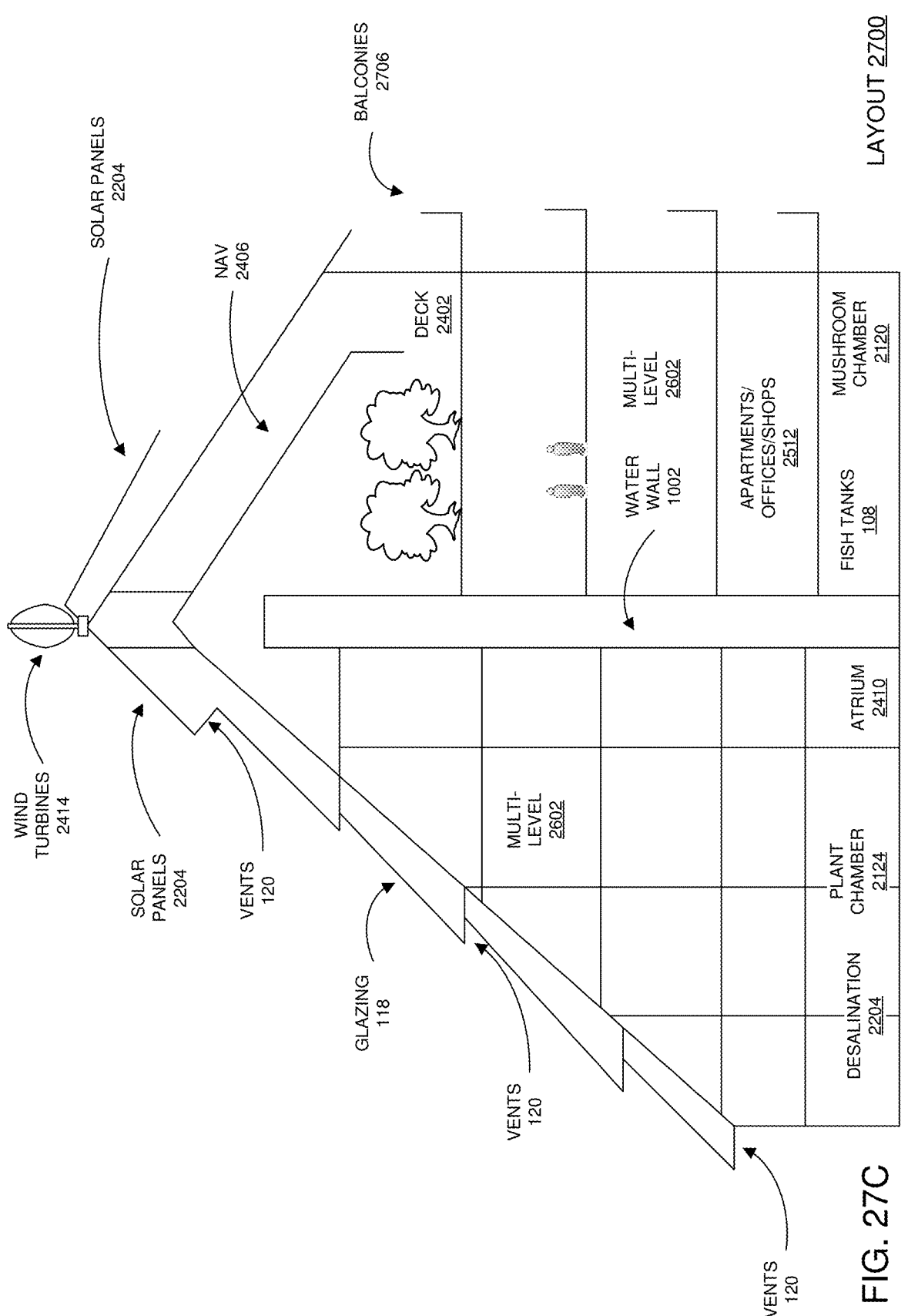

In FIGS. 27A-27C, a passive solar building or skyscraper system 2700 can include the features previously described with respect to FIGS. 24-26. In FIG. 27A, advantageously, the side buildings 2604 can further include the louvers 2508, and the like. In FIG. 27B, advantageously, the deck 2402 can include various entrances 2404, and the like, for providing access to the apartments, offices, shops, and the like, 2512. In FIG. 27C, advantageously, balconies 2706 can be provided in the rear of the structure for access by the apartments, offices, shops, and the like, 2512. The atrium and/or the apartments, offices, shops, and the like, 2512 can be of the multi-level design 2602, and the like.

Figure 28A:
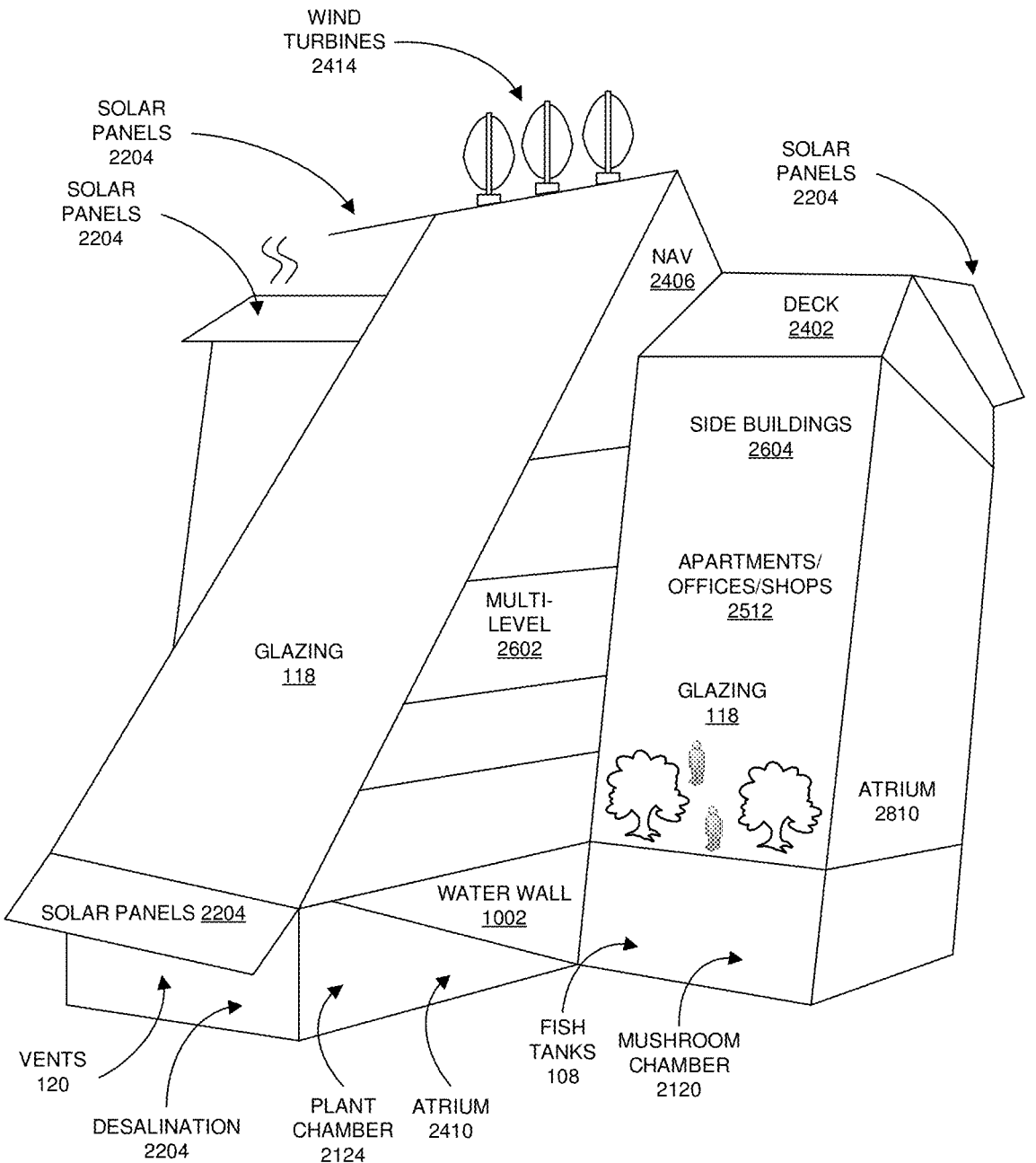
Figure 28B:
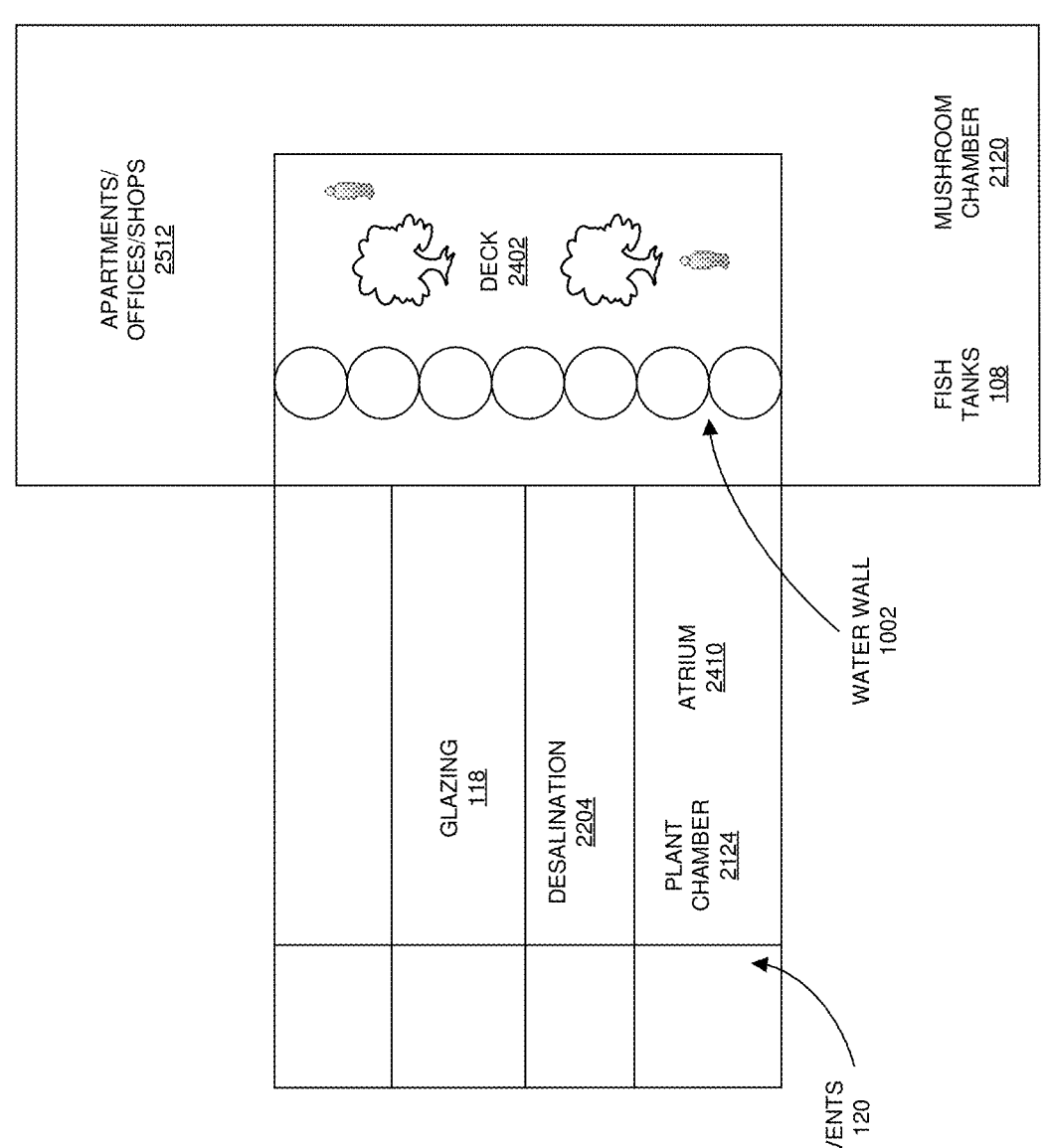

In FIGS. 28A-28B, a passive solar building or skyscraper system 2800 can include the features previously described with respect to FIGS. 24-27. In FIG. 28A, advantageously, the side buildings 2604 can include open atriums 2810, and the like. In FIG. 28B, advantageously, the deck 2402 can be provided so as the provide a view to the apartments, offices, shops, and the like, 2512 provided therearound, and the like.

In FIG. 29, a passive solar building or skyscraper system 2900 can include the features previously described with respect to FIGS. 24-28. Advantageously, the balconies 2706 are provided on the sun facing side of the water wall 1002, so as the provide a view of the open atrium 2410, and the like, from the apartments, offices, shops, and the like, 2512 of the multi-level designs 2602.

In FIG. 30, a passive solar building or skyscraper system 3000 can include the features previously described with respect to FIGS. 24-29. Advantageously, the balconies 2706 are provided within the water wall 1002 for a visual effect, and so as the provide a view of the open atrium 2410, and the like, from the apartments, offices, shops, and the like, 2512 of the multi-level designs 2602.

In FIG. 31, a passive solar building or skyscraper system 3100 can include the features previously described with respect to FIGS. 24-30. Advantageously, the apartments, offices, shops, and the like, 2512 and the atrium 2410 are of the multi-level designs 2602, and an illustrative configuration of the natural air ventilation system 2406 is shown.

Figures 32A, 32B:
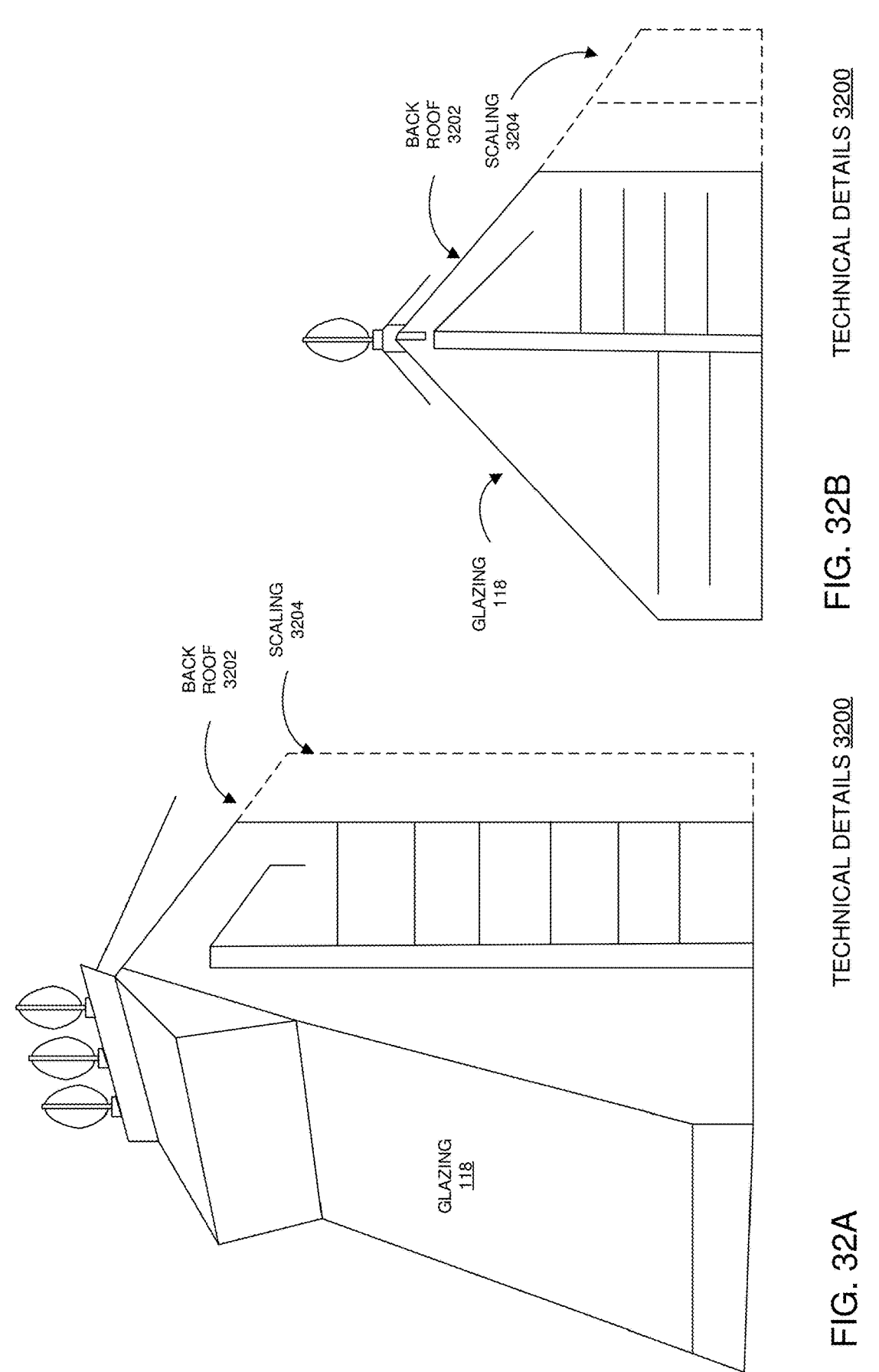

In FIGS. 32A-32B, a passive solar house or building or skyscraper system 3200 can include the features previously described with respect to FIGS. 24-31. Advantageously, the passive solar houses, building or skyscraper systems 3200 can be scaled at 3204 based on an angle of the glazing 118 and by extending the back roof 3202, and the like, as shown.

Figure 33:
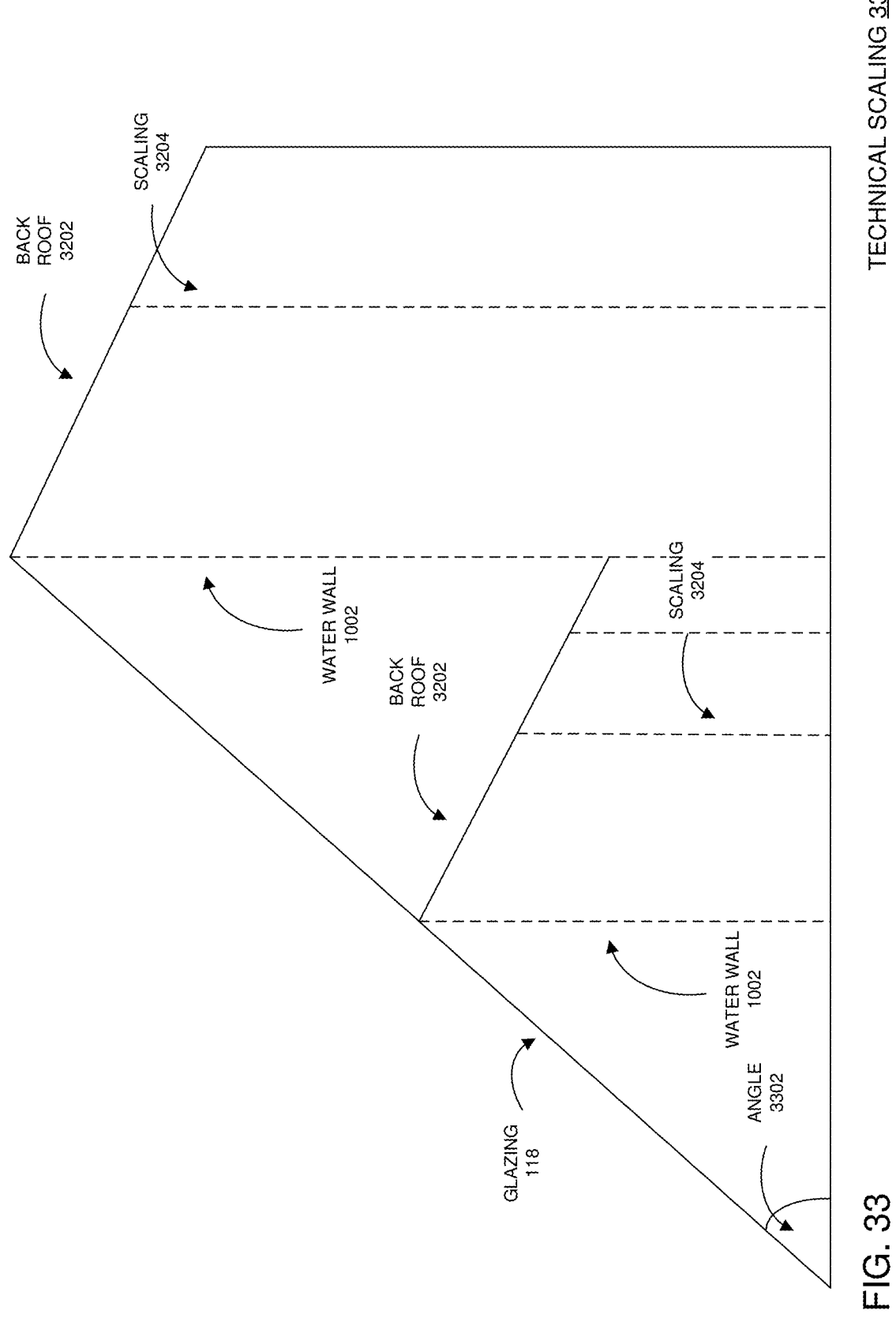

In FIG. 33, a passive solar house or building or skyscraper system 3300 can include the features previously described with respect to FIGS. 24-32. Advantageously, the passive solar houses, building or skyscraper systems 3300 can be scaled at 3204 based on an angle 3302 of the glazing 118 and by extending locating the water wall 1002 relative to the back roof 3202, and the like, as shown.

In FIGS. 34A-34C, a passive solar house or building or skyscraper system 3200 can include the features previously described with respect to FIGS. 24-33. In FIGS. 34A-34B, advantageously, the vents 120 can be configured with upward or downwards scallop designs, as shown. In FIG. 34C, advantageously, the angle 3302 can be used for the multi-level designs 2602 of the atrium 2410, and the like.

In FIG. 35, a passive solar house or building or skyscraper system 3500 can include the features previously described with respect to FIGS. 24-34. Advantageously, the balconies 2706 can be configured in spaces 3502 between the circular water wall columns 1002, and the like.

In FIG. 36, a passive solar house or building or skyscraper system 3600 can include the features previously described with respect to FIGS. 24-35. Advantageously, the desalination system 2204 can be located on the sun facing side of the water wall 1002 underneath the atrium 2410, and the like, and so as to act as a solar still, and the like. The fish tanks 108 can be located on the shade side of the water wall 1002 underneath apartments, offices, shops, and the like, 2512, and so as to keep the fish tanks 108 relatively cooler, as needed.

Figure 37:
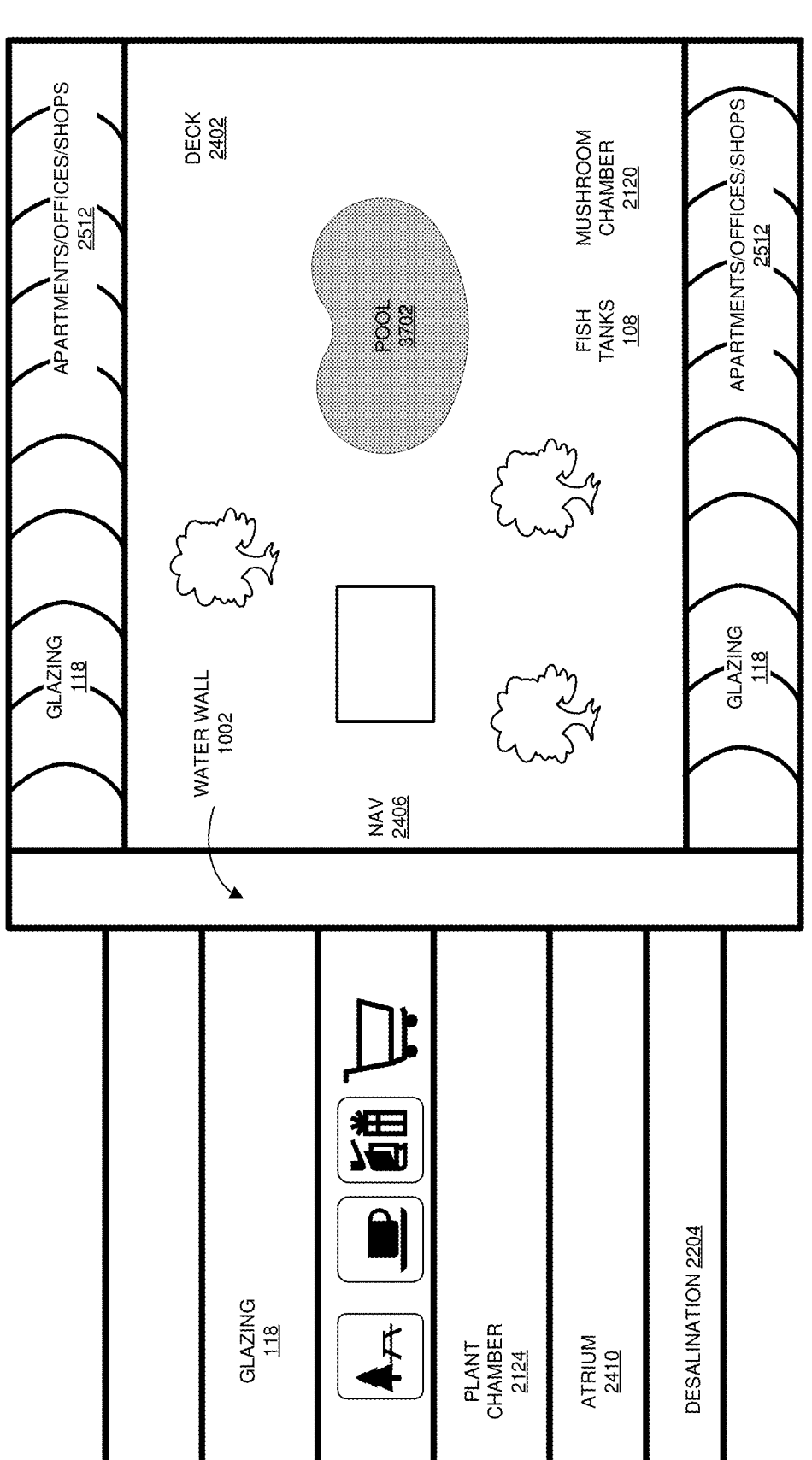

In FIG. 37, a passive solar house or building or skyscraper system 3700 can include the features previously described with respect to FIGS. 24-36. Advantageously, the deck 2402 can include a pool 3702, with the deck 2402 overlooking or looking into the apartments, offices, shops, and the like.

Figure 38:
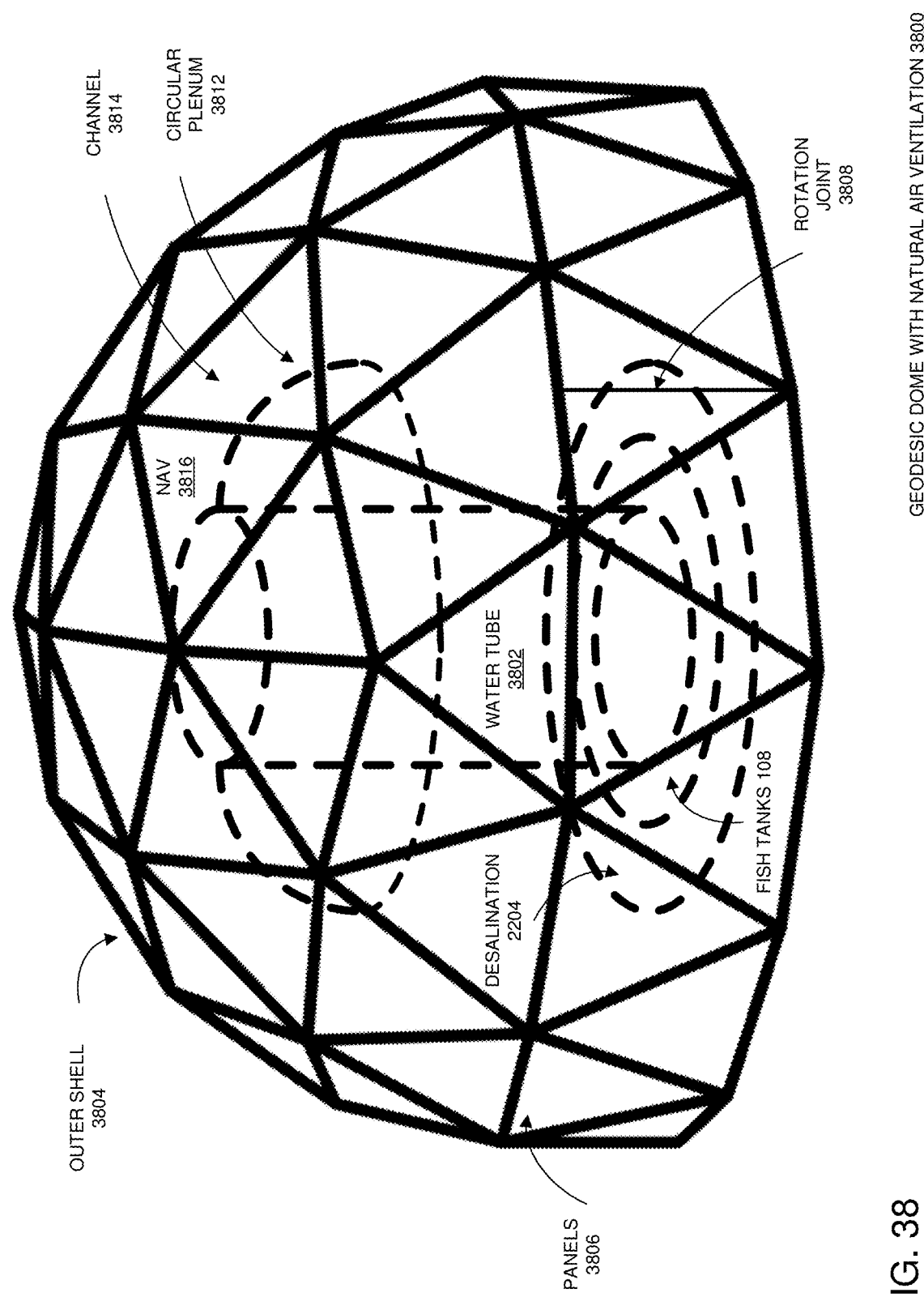

FIGS. 38-43 are used to illustrate a geodesic, passive solar, aquaponics and greenhouse system with natural air ventilation and circular swales suited for extreme desert, extreme cold, and space environments, employed with the systems and methods for solar greenhouse aquaponics and black soldier fly (BSF) composter and auto fish feeder of FIGS. 1-37. In FIG. 38, the geodesic, passive solar, aquaponics and greenhouse system 3800 with natural air ventilation includes the circular fish tanks 108, and the desalination system 2204, a water tube 3802, a circular Natural Air Ventilation (NAV) system 3816 having a circular channel 3814, and a circular plenum 3812, and the like, based on further and previously described teachings, and the like. A geodesic outer shell 3804 includes panels 3806 (e.g., light transmitting glazing, light programmable glass, etc.) on rotation joints 3808 to allow the panels 3806 to rotate to provide air flow, light, shade, and the like, as needed.

Figure 39:
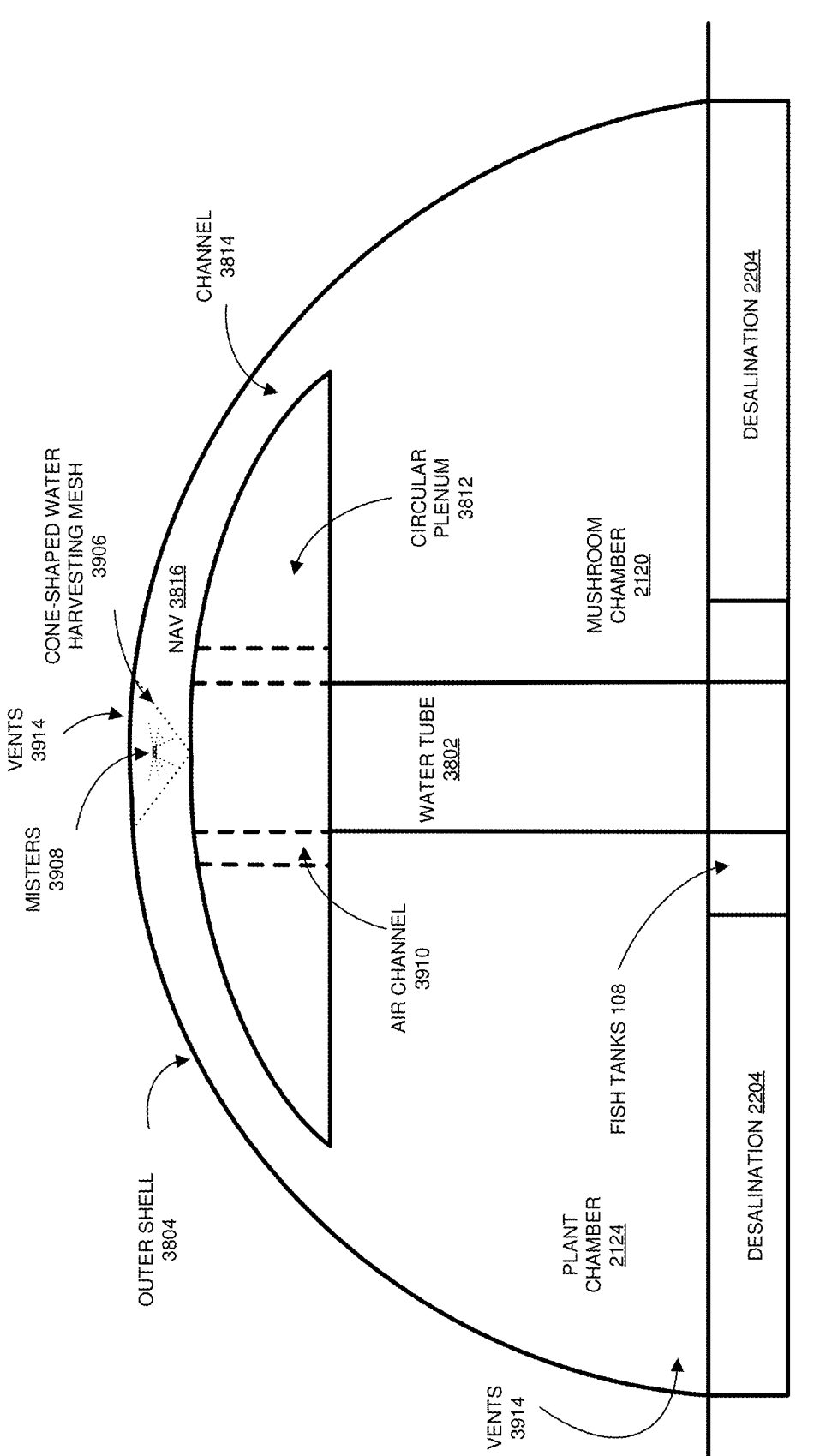

In FIG. 39, further details of the geodesic, passive solar, aquaponics and greenhouse system 3800 are shown, including the water tube 3802 acting as a thermal battery extending into the fish tanks 108, and the like. Advantageously, saltwater in the desalination system 2204 heated by solar energy transmitted through the outer shell 3804 acts like as a solar still, and the like, and can be employed to fill the water tube 3802 and the fish tanks 108, and to provide fresh water, as needed.

Advantageously, plants provided within a portion of the structure configured as the plant chamber 2124 can produce O2 that is heated by solar energy transmitted through the outer shell 3804 to rise through a circular air channel 3910 to be captured by the NAV system 3816. In addition, venting, as needed, can be provided by rotation of the panels 3806 acting as vents 3914. The NAV system 3816 cools the captured O2 via misters 3908, so that the cooled O2 travels down the circular channel 3814 formed by the circular plenum 3812 and the outer shell 3804 of the structure. The cooled O2 traveling down the circular channel 3814, advantageously, flushes CO2, for example, produced by fish in the fish tanks 108, mushrooms provided within a portion of the structure configured as the mushroom chamber 2120, animals, humans, and the like, into the plant chamber 2124 to be recycled by the plants and recirculated, as described. In addition, cone-shaped water harvesting mesh 3906 and a gutter system, as previously described, can provided to capture internal and/or external moisture, and the like.

In FIGS. 40-41, further details of the panels 3806, are shown. In FIG. 41, the panels 3806 include subpanels 4004 and 4006 disposed on the rotation joint 3808 and with stepper motors 4002 for providing programmable rotation of the panels 3806, and with programmable sensors 4008 (e.g., temperature (T), pressure (P), air flow (F), relative humidity (RH), light (L), O2, CO2, etc.). In FIG. 41, the panels 4004 and 4006 include respective glazing 4102 and 4104 (e.g., light transmitting glazing, light programmable glass, etc.), advantageously, providing programmable shading, light transmission, light refection, and the like, as needed.

FIGS. 42-43 are used to illustrate a circular swale system 4200 that can be employed with the systems and methods of FIGS. 1-41. In FIG. 42, the circular swale system 4200 includes the circular fish tank 108 surrounded by circular swales 4204, and the like, with circular berms 4206, and the like, interspersed therebetween. Ramps 4208 are provided to allow planting and harvesting of plants, trees, flowers, and the like, growing on the berms 4206, as well as culturing and harvesting of fish from the fish tank 108. In FIG. 43, the circular swale system 4200 further includes the water tube 3802 extending into the fish tank 108, advantageously, heating and/or cooling of the fish tank 108 water, as needed. The berms 4206 and swales 4204 are configured in a step like fashion, sloping downward from the outer shell 3804, so as to, advantageously, capture water, provided by a water pump or geyser pump 4306 and water line 4308, and the like, flowing from the upper swales 4204 through the berms 4206 into the fish tank 108. The planted berms 4206, advantageously, filter the wastewater from the fish tank 108, while the wastewater from the fish tank 108 provides nutrients for plants planted berms 4206. A pond liner 4302 can be provided underneath the berms 4206, advantageously, to maintain water within the swales 4204. The circular swale system 4200 can be provided in ground 4304 and/or within the desalination system 2204, as needed.

In the embodiments of FIGS. 1-43, the water wall 1002 or the water tube 3802 can be configured with light programmable glass, as previously described, and/or various liquids to allow the water wall 1002 or tube 3802 to act as thermal battery and transmit, store and/or reflect light energy (e.g., as described in "'Smart' windows (electrochromic glass)" available on the world wide web at explainthatstuff.com/ electrochromic-windows.html, and "Scientists Develop Liquid That Can Store Solar Energy For More Than a Decade" available on the world wide web at interestingengineering-.com/scientists-develop-liquid-that-can-store-solar-energy-for-more-than-a-decade, incorporated by reference herein), as needed, and with colored lighting provided therearound or therewithin as possible design features, and the like. For example, the water wall 1002 or tube 3802 can be programmed to be black during the day, and clear at night with lights shining therein or throughout, and the like, and the structures can employ natural and/or artificial lighting combination, and the like.

Figure 44:
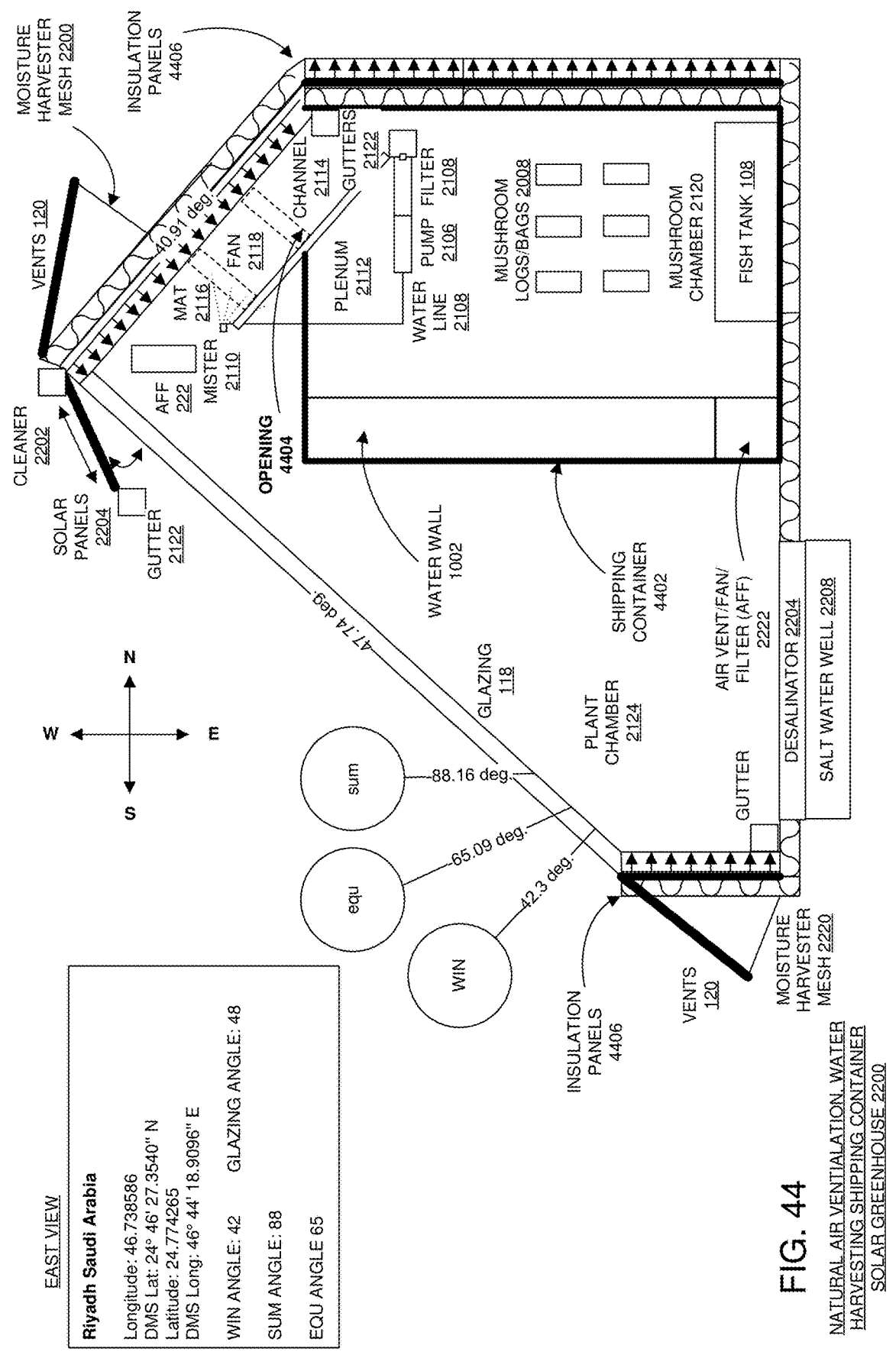
FIGS. 44 and 45A-45C are used to illustrate solar greenhouse shipping container systems with natural air ventilation and water harvesting configurations suited for desert, seasteading, and space applications.

FIGS. 44 and 45A-45C are used to illustrate solar greenhouse shipping container systems with natural air ventilation and water harvesting configurations suited for desert, seasteading, and space applications employed in the systems and methods of FIGS. 1-43. In FIG. 44, a shipping container 4402 (e.g., a standard 8'×8.5'×10', 20' or 40' shipping container, etc.) is configured to transform into a passive solar greenhouse, as previously decribed. The plenum 2112 is configured into an opening 4404 in the shipping container 4402 for the natural air ventilation system. The water wall 1002 and the air vents, filters, and/or fans 2222 can be integrated as part of the shipping container 4402. Insulation panels 4406 can be provided around the shipping container for additional insulation, as needed. Advantageously, the shipping container systems can be configured as foldable and deployable, sun-facing structures for use in remote locations, space applications, and the like.

Figure 45A:
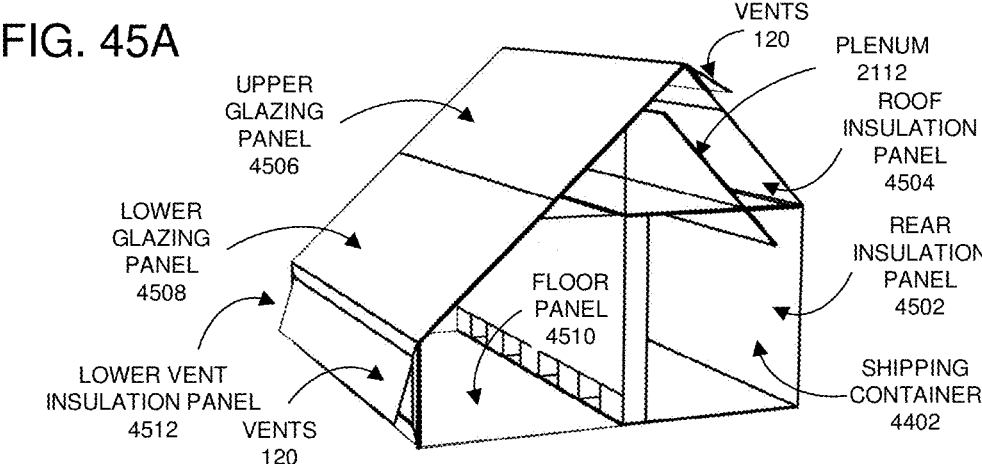

In FIG. 45A, the solar greenhouse shipping container system is shown after foldable and stackable rear insulation panel 4502, roof insulation panel 4504, upper glazing panel 4506, lower glazing panel 4508, floor panel 4510, and lower vent panel 4512, and the plenum 2112 are deployed. The lower vent panel 4512 and the roof insulation panel 4504 are configured with the respective vents 120.

Figure 45B:
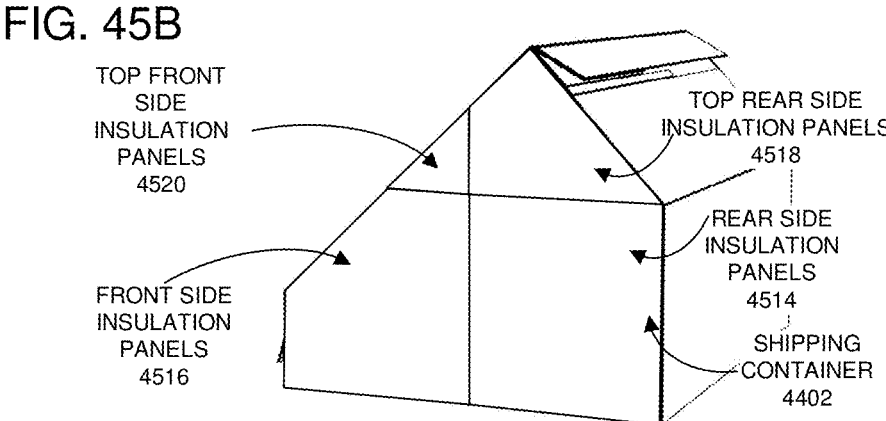

In FIG. 45B, the solar greenhouse shipping container system is shown after foldable and stackable rear side insulation panels 4514 (e.g., on East and West sides), front side insulation panels 4516 (e.g., on East and West sides), and top rear side insulation panels 4518 (e.g., on East and West sides), and top front side insulation panels 4520 (e.g., on East and West sides) are deployed completing the deployment sequence. Advantageously, the shipping container 4402 can be used to store the various equipment employed for aquaponics, mushroom, fish and plant cultivation, as previously described, and for use after deployment.

Figure 45C:
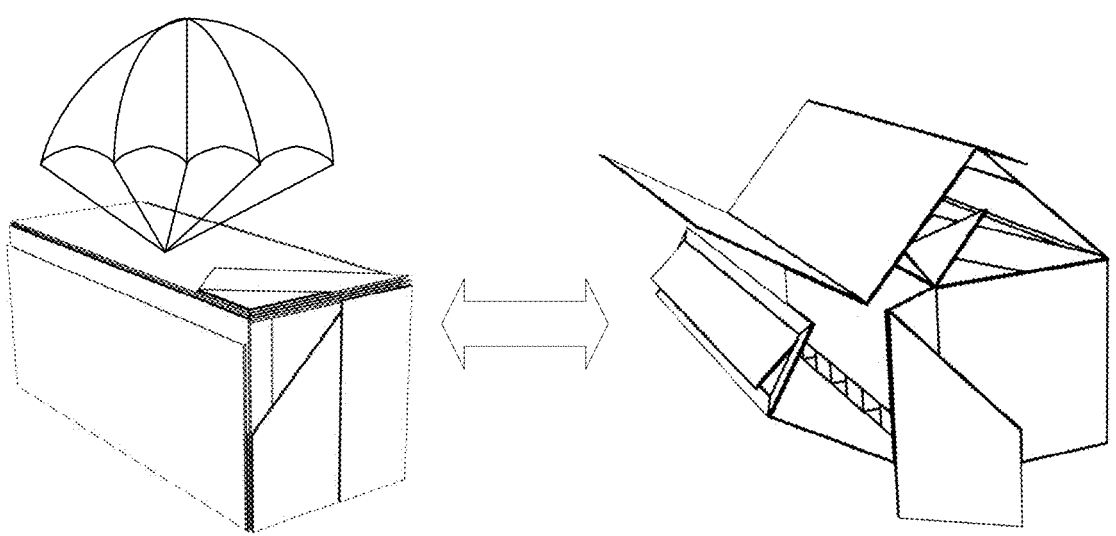

In FIG. 45C, the solar greenhouse shipping container system is shown before and after transition for deployment. Advantageously, solar greenhouse shipping container system can be delivered by parachute, balloon, rockets, and the like, to remote, space, seastead, and the like, locations for relief, military, space, and the like, applications.

Figure 46:
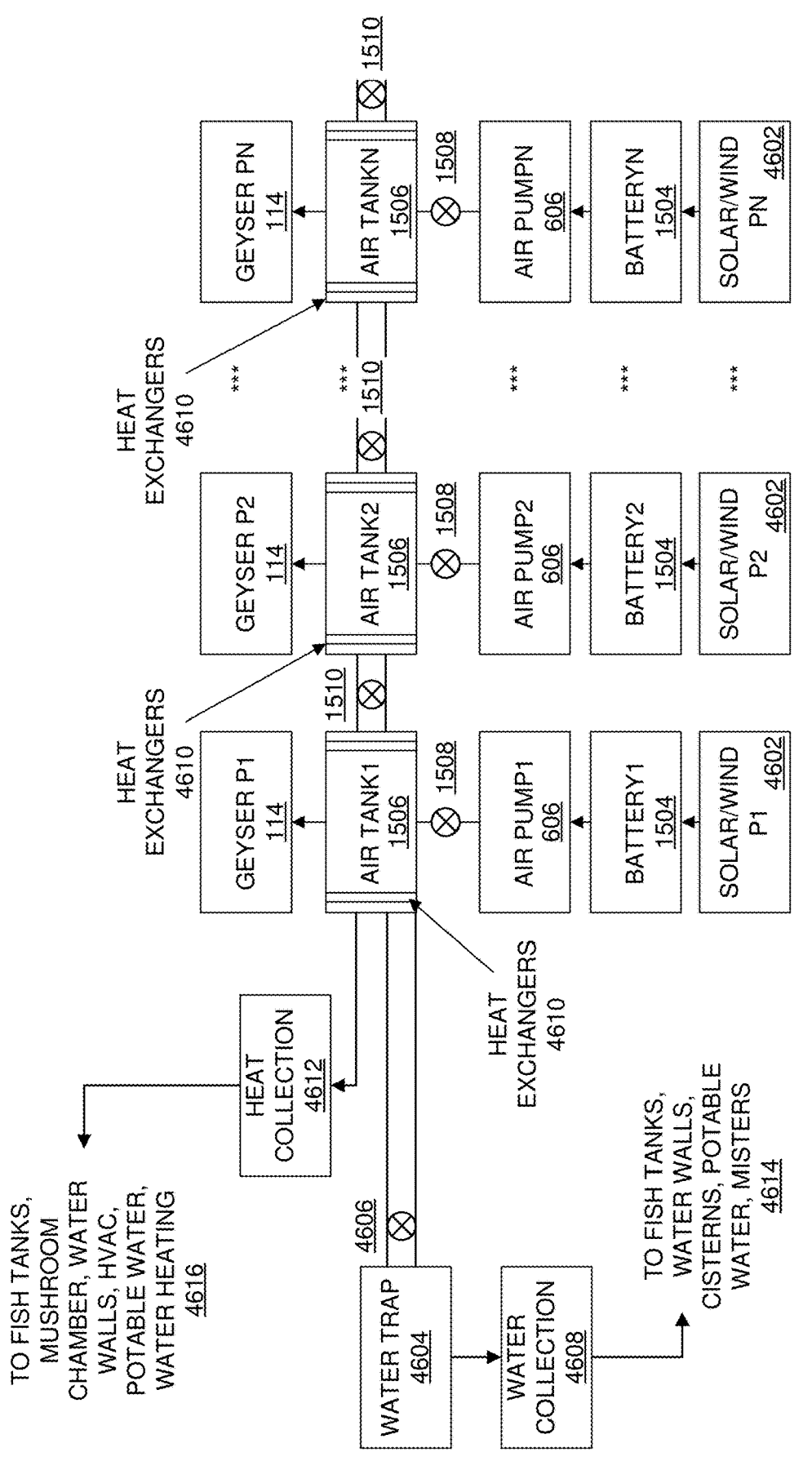
FIG. 46 is an illustrative geyser pump air distribution heat and water harvesting systems.

FIG. 46 is an illustrative geyser pump air distribution heat and water harvesting systems employed in the systems and methods of FIGS. 1-45. In FIG. 46, solar/wind power systems 4602 can be employed with the configuration of FIG. 15. Advantageously, wind turbines 4602 can be used to run the air pumps 606 directly and so as to bypass the batteries 1504. In other embodiments, both solar panels and wind turbines 4602 can be employed, advantageously, to provide redundancy, and the like. Water traps 4604 are employed to filter out contaminates from collected water that is generated during compression in the air tanks 1506. Water collection system 4608 acquires water from the water traps 4604 for storage until utilization by a water distribution stage at 4614, as needed potable or non-potable water for fish tanks, water walls, cisterns, misters, human consumption, and the like. Heat exchangers 4610 acquire excess heat generated during compression from the air tanks 1506, for example, via a system of coiled tubes, and the like, that can hold gas or liquid, and the like. Heat collection system 4612 stores the acquired heat in the form of hot gas or hot liquid, and the like, advantageously, to be delivered for utilization in other systems, such as the fish tanks, mushroom chambers, HVAC, potable or non-potable water heating, and the like, as needed.

Figure 47:
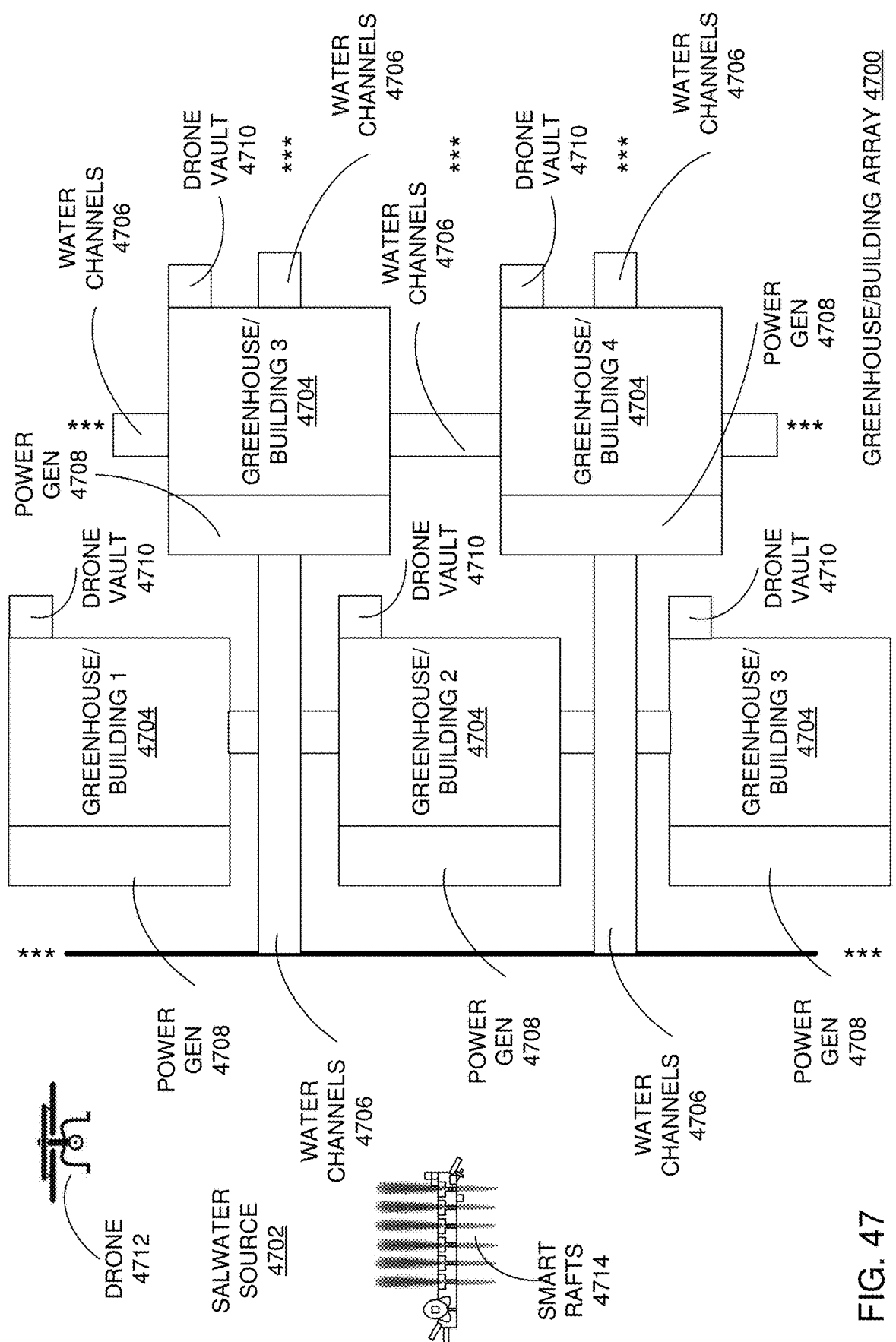
FIG. 47 is an illustrative system including an array of passive solar greenhouses, containers, houses, buildings, skyscrapers, and the like, systems employing aquaponics and greenhouse technologies with fish plant and mushroom production and with natural air ventilation, well suited for extreme desert, extreme cold, and space environments.

FIG. 47 is an illustrative system 4700 including an array of passive solar greenhouses, containers, houses, buildings, skyscrapers, and the like, systems employing aquaponics and greenhouse technologies with fish plant and mushroom production and with natural air ventilation, well suited for extreme desert, extreme cold, and space environments. In FIG. 47, the system 4700 can include a saltwater source 4702, such as a sea or ocean or other saltwater source, and the like, which can be located near an array of passive solar greenhouses, houses, containers, buildings, skyscrapers 4704, and the like, such as those previously described herein. Such structures can employ aquaponic and greenhouse technologies with natural air ventilation for integrated production of fish, plant and mushroom production, as previously described herein, as well as being well suited for extreme desert and extreme cold and space environments, and the like.

A series of saltwater channels 4706 coupled to the saltwater source 4702 can be suitably constructed and connected to the structures 4704 to deliver saltwater for desalinization, and freshwater generation, as previously described, by the structures 4704. The structures 4704 can be equipped with power generation technologies 4708, such as solar panels, wind turbines, and the like, as previously described, advantageously, providing off-grid operation energy generation, and the like. As the structures 4704 are advantageously based on passive solar designs, the structures 4704 employ relatively small amounts of energy and can thus produce excess energy that can be exported or sold, and the like, as needed. Advantageously, the system 4700 can be employed to design smart cities, eco villages, and the like.

The greenhouses or buildings 4704 can further include drone vaults 4710 located therewith. The drone vaults 4710 can configured as surface or subsurface secure containers, and the like, that can be used as landing spots for one or more drones 4712. The drones 4712 employed for delivery of supplies, and the like, and for transporting harvested outputs from the greenhouses or buildings 4704 to remote or nearby locations, and the like. For example, such outputs can include biologically rich soil, compost, drinking water, fish, plants, mushrooms, salt from the desalinization processes, and the like. The drones 4712 can also to deliver inputs, such as seeds, fertilizer, equipment, supplies, and the like, as needed, by the greenhouses or buildings 4704.

In addition, the saltwater source 4702 can be a contaminated water source 4702, for example, such as the Gulf of Mexico, USA, and the like, where the greenhouses and buildings 4704 can be used to desalinate water, purify, and/or generate fresh water, and the like, from the contaminated water source 4702, including generating drinking water, water to produce fish, plants and mushrooms, based on the desalinated or purified water, and the like. The drones 4712 can be used along with smart rafts 4714 systems and methods, for example, as further described in U.S. patent application Ser. No. 17/108,522 of Lewis et al., entitled "SMART RAFT SYSTEM AND METHOD FOR MONITORING AND IMPROVING WATER QUALITY TO MITIGATE ALGAL BLOOMS," filed Dec. 12, 2020, incorporated by reference herein. Such smart rafts 4714 can be employed for monitoring and improving water quality of the contaminated water source 4702, for example, to mitigate harmful algal blooms, and the like. The rafts 4714 can be made from a mycomaterials, and the like, and include tube-shaped pods formed in the raft 4714 and configured to hold seed or media and configured with a root channel at the bottom of the pods extending through a bottom of the raft 4714. A sensor holder formed in the raft 4714 can hold a water quality sensor, and the like, accessing a water channel extending through a bottom of the raft 4714. Remedial plants can be grown in the tube-shaped pods with roots of the remedial plants passing through the water channel into the contaminated water source 4702 underneath the raft 4714 The rafts can be controlled by the drones 4712 in order to locate areas where the rafts 4714 are most needed, and the rafts 4714 can have solar power, and the like, and propulsion and geo location systems, and the like, to navigate the rafts 4714 to the places where they can be employed. The water quality parameters measured by the rafts 4714 can be communicated to the drones 4712 for advantageous navigation and placement of the rafts 4714 in the contaminated water source 4702.

Figure 48:
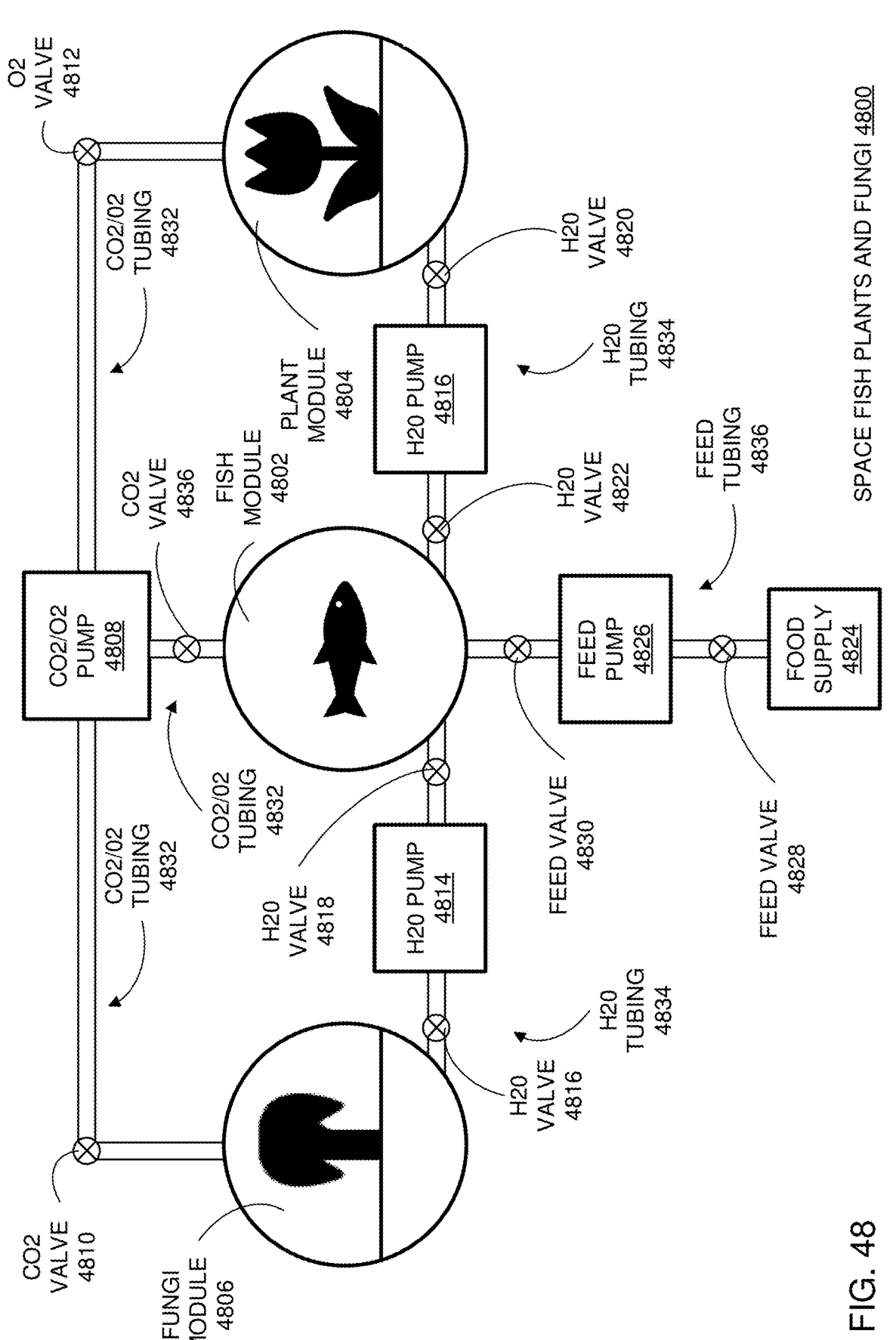
FIG. 48 is an illustrative system employing fish, plants and mushrooms for space environments.

FIG. 48 is an illustrative system 4800 employing fish, plants and mushrooms for space environments, and the like. In the system 4800, a fish module 4802, a plant module 4804, and a fungi module 4806 are provided in suitable environmentally sealed containers that are applicable for operation in space, underwater, and the like. A suitable controllable, bidirectional $CO_2/O_2$ pump 4808 is coupled to the fish module 4802, the plant module 4804, and the fungi module 4806 via $CO_2/O_2$ coupling tubes 4832. Suitable programmable $CO_2$ valves 4810 and 4836 and $O_2$ valve 4812 are employed on the $CO_2/O_2$ coupling tubes 4832 in order to provide programmable $CO_2$ and $O_2$ gas exchange between the modules 4802, 4804 and 4806.

Similarly, a suitable controllable, bidirectional $H_2O$ pump 4814 is coupled to the fish module 4802 and the fungi module 4806 via $H_2O$ coupling tubes 4834. Suitable, programmable $H_2O$ valves 4816 and 4818 are employed on the $H_2O$ coupling tubes 4834 in order to provide programmable $H_2O$ exchange between the modules 4802 and 4806. A suitable controllable, respective bidirectional $H_2O$ pump 4816 is coupled to the fish module 4802 and the plant module 4804 via receptive $H_2O$ coupling tubes 4834. Suitable programmable $H_2O$ valves 4820 and 4822 are employed on the respective $H_2O$ coupling tubes 4834 in order to provide programmable $H_2O$ exchange between the modules 4802 and 4804.

A suitable refillable fish food supply 4824 is coupled to a suitable fish feed pump 4216 that is coupled to the to the fish module 4802 via fish feed tubes 4836 and respective programmable feed control valves 4828 and 4830 in order to provide programmable feeding to the fish module 4802. Advantageously, CO2/O2/H2O exchange and fish feeding can be controlled to allow plants, fish and mushrooms to propagate in space, underwater, and the like.

In further embodiments, a fully air-powered, n-way redundant aquaponic system for integrated cultivation of various fish, plant, and mushroom species, off-grid is provided. Each grow bed includes a respective DC air pump, solar panel, and battery to ensure self-sufficiency, redundancy, and enhanced resilience. Each mushroom grow bed also includes an evaporative cooling system for year-round mushroom production.

The fully air-powered, n-way redundant system incorporates redundant DC air pumps, solar panels, and batteries to ensure self-sufficiency, redundancy, and enhanced resilience. Black soldier fly (BSF) and red wrigglers composting systems, provide efficient organic waste management and nutrient cycling, promoting sustainability while minimizing environmental impact. The system's self-sustainability and reduced reliance on external power is advantageous for remote and/or resource-limited applications (e.g., space applications). Such an integrated approach distinguishes from conventional solutions. The inclusion of air-powered aquaponics, mushroom cultivation, BSF and red wrigglers composting, a water wall thermal battery, and an evaporative cooling system sets the system apart from its competition, providing a holistic solution for sustainable food production, effectively addressing resource utilization, waste management, and controlled environmental conditions.

The proposed solution is a fully air-powered, n-way redundant, integrated, aquaponics and mushroom production system. This innovative system integrates aquaponics, which involves the cultivation of plants and fish in a mutually beneficial environment, with aquaponic mushroom cultivation. Its primary objective is to establish a sustainable and efficient approach to food production that addresses water usage, nutrient recycling, and waste management challenges.

Figure 49:
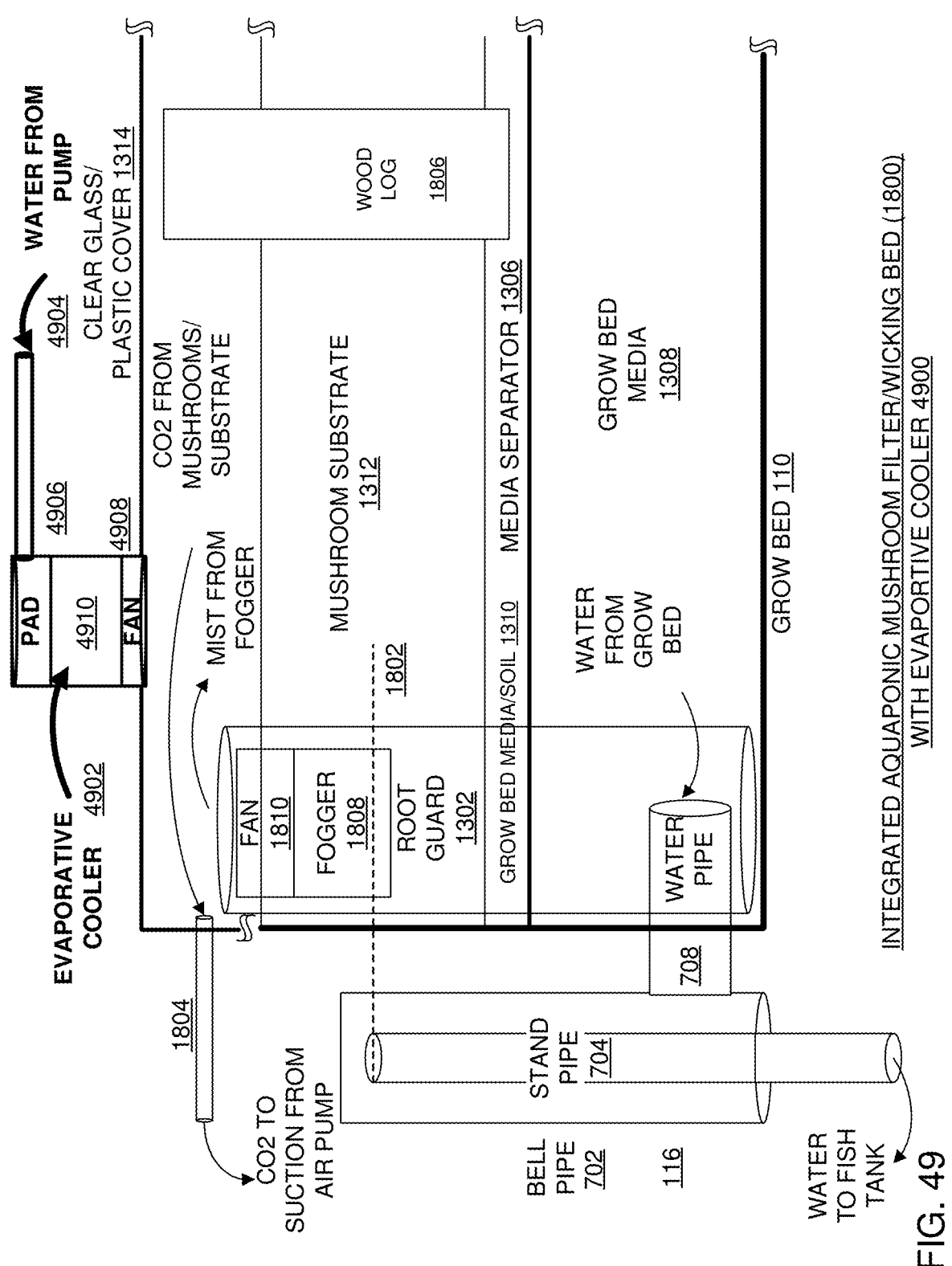
FIGS. 49-50 are used to illustrate a fully air-powered, n-way redundant aquaponic system with mushroom grow beds having an evaporative cooling system for year-round mushroom production.
Figure 50:
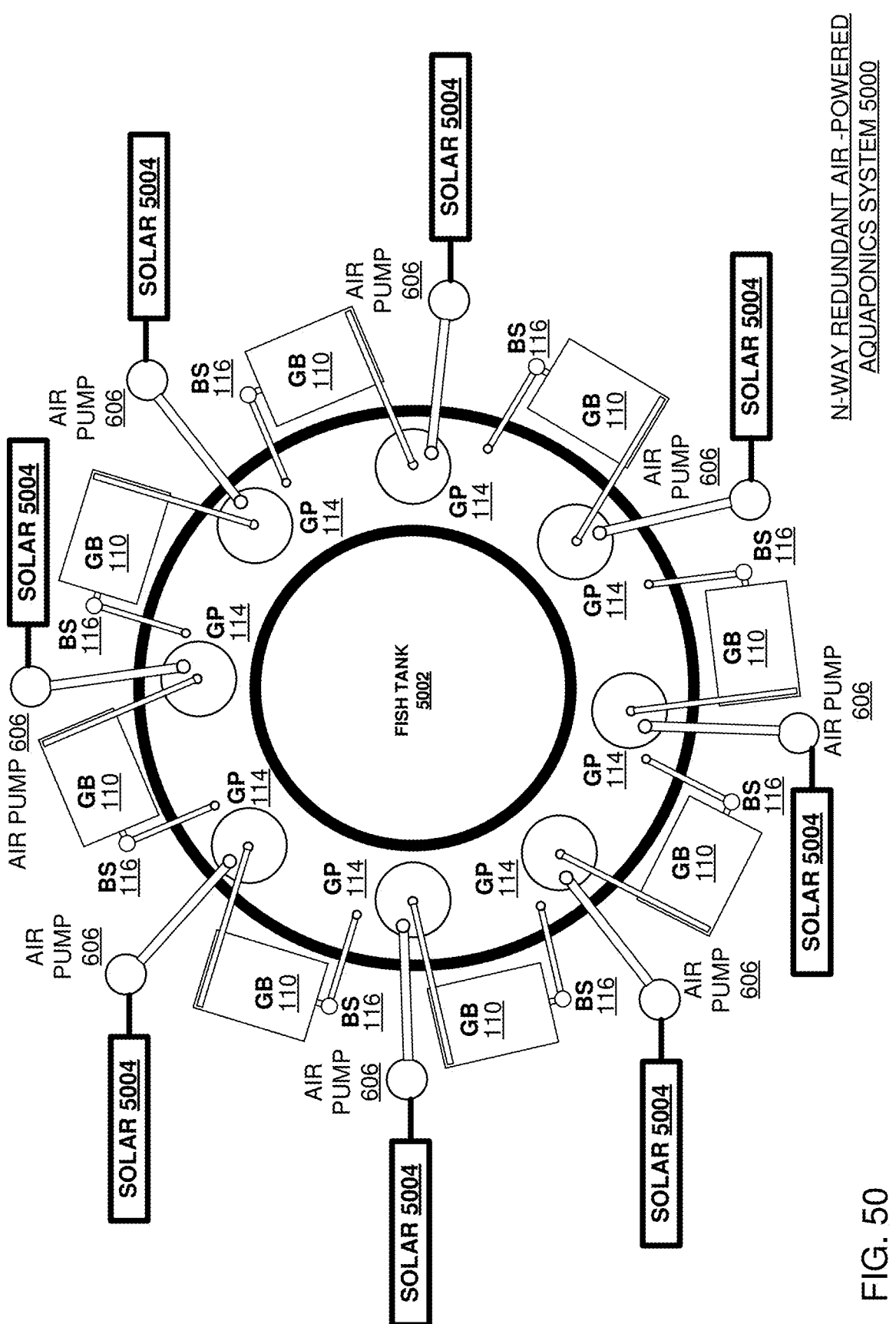

FIGS. 49-50 are used to illustrate a fully air-powered, n-way redundant aquaponic system with mushroom grow beds having an evaporative cooling system for year-round mushroom production. In FIG. 49, each grow bed 110 further includes an evaporative cooling system 4902 having a water pump input 4904, and with an evaporative cooling pad 4906, and air intake fan 4908 connected to a cooling tube 4910 for delivering evaporatively cooled and moistened air through the cover 1314 of the mushroom grow bed 1308. The evaporative cooling pad 4906 receives water from water pump 4904, which is evaporatively cooled by the intake fan 4908 and delivered to the mushroom substrate 1312.

FIG. 50 shows n-way redundant aquaponic system with grow beds that each can includes a respective DC air pump, solar system having a solar panel, and battery to ensure self-sufficiency, redundancy, and enhanced resilience. The system 5000 can include one or more of the grow beds 110 configured as aquaponic mushroom, flood and drain grow beds configured with an evaporative cooling system, as described in FIG. 49. In addition, the fish tank 5002 is configured with the geyser pumps 114 integrated within the fish tank 5002. Each of the air pumps 606 can be powered by respective solar power systems 5004 have a solar panel, battery, charge controller (not shown). Advantageously, each grow bed 110 can include a respective air pump 606 and be configured as a module that can be taken in and put back into the system, simply by connecting to the integrated geyser pump 114 of the fish tank 5002 to the grow bed 110, connecting the output of the bell syphon 116 to the fish tank 5002, and then connecting the solar system 5004 to the air pump 606 to sustainably, and off-grid power the air pump 606. The system 5000 can be employed to grow suitable varieties of fish, plant and mushroom species, depending on the plant and mushroom grow bed 116 configurations, with the evaporative cooling system of FIG. 49 connected to the mushroom grow beds 116, as previously described.

Advantageously, the illustrative systems and methods are well suited for extreme desert, extreme cold, and space environments, safe isolation spaces during pandemics, by allowing for efficient and cost-effective greenhouse, mushroom, and fish feeding systems for aquaponics, mushroom, and microgreens cultivation, food security applications, and the like.

Although the illustrative systems and methods are described in terms of aquaponics, the illustrative systems and methods can be applied to any other suitable types of aquaculture, greenhouse house, building and skyscraper, space, and the like, technologies, as will be appreciated by those of ordinary skill in the relevant arts.

All the features of the illustrative systems and methods of FIGS. 1-48, as described herein, can be employed alone or in any suitable combination, as will be appreciated by those of ordinary skill in the relevant arts.

The above-described devices and subsystems of the illustrative embodiments can include, for example, any suitable servers, workstations, PCs, laptop computers, PDAs, Internet appliances, handheld devices, cellular telephones, wireless devices, other devices, and the like, capable of performing the processes of the illustrative embodiments. The devices and subsystems of the illustrative embodiments can communicate with each other using any suitable protocol and can be implemented using one or more programmed computer systems or devices.

One or more interface mechanisms can be used with the illustrative embodiments, including, for example, Internet access, telecommunications in any suitable form (e.g., voice, modem, and the like), wireless communications media, and the like. For example, employed communications networks or links can include one or more wireless communications networks, cellular communications networks, G3 communications networks, Public Switched Telephone Network (PSTNs), Packet Data Networks (PDNs), the Internet, intranets, a combination thereof, and the like.

It is to be understood that the devices and subsystems of the illustrative embodiments are for illustrative purposes, as many variations of the specific hardware used to implement the illustrative embodiments are possible, as will be appreciated by those skilled in the relevant art(s). For example, the functionality of one or more of the devices and subsystems of the illustrative embodiments can be implemented via one or more programmed computer systems or devices.

To implement such variations as well as other variations, a single computer system can be programmed to perform the special purpose functions of one or more of the devices and subsystems of the illustrative embodiments. On the other hand, two or more programmed computer systems or devices can be substituted for any one of the devices and subsystems of the illustrative embodiments. Accordingly, principles and advantages of distributed processing, such as redundancy, replication, and the like, also can be implemented, as desired, to increase the robustness and performance of the devices and subsystems of the illustrative embodiments.

The devices and subsystems of the illustrative embodiments can store information relating to various processes described herein. This information can be stored in one or more memories, such as a hard disk, optical disk, magneto-optical disk, RAM, and the like, of the devices and subsystems of the illustrative embodiments. One or more databases of the devices and subsystems of the illustrative embodiments can store the information used to implement the illustrative embodiments of the present inventions. The databases can be organized using data structures (e.g., records, tables, arrays, fields, graphs, trees, lists, and the like) included in one or more memories or storage devices listed herein. The processes described with respect to the illustrative embodiments can include appropriate data structures for storing data collected and/or generated by the processes of the devices and subsystems of the illustrative embodiments in one or more databases thereof.

All or a portion of the devices and subsystems of the illustrative embodiments can be conveniently implemented using one or more general purpose computer systems, microprocessors, digital signal processors, micro-controllers, and the like, programmed according to the teachings of the illustrative embodiments of the present inventions, as will be appreciated by those skilled in the computer and software arts. Appropriate software can be readily prepared by programmers of ordinary skill based on the teachings of the illustrative embodiments, as will be appreciated by those skilled in the software art. Further, the devices and subsystems of the illustrative embodiments can be implemented on the World Wide Web. In addition, the devices and subsystems of the illustrative embodiments can be implemented by the preparation of application-specific integrated circuits or by interconnecting an appropriate network of conventional component circuits, as will be appreciated by those skilled in the electrical art(s). Thus, the illustrative embodiments are not limited to any specific combination of hardware circuitry and/or software.

Stored on any one or on a combination of computer readable media, the illustrative embodiments of the present inventions can include software for controlling the devices and subsystems of the illustrative embodiments, for driving the devices and subsystems of the illustrative embodiments, for enabling the devices and subsystems of the illustrative embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the illustrative embodiments of the present inventions can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the illustrative embodiments of the present inventions can be distributed for better performance, reliability, cost, and the like.

As stated above, the devices and subsystems of the illustrative embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present inventions have been described in connection with a number of illustrative embodiments, and implementations, the present inventions are not so limited, but rather cover various modifications, and equivalent arrangements, which fall within the purview of the appended claims.

What is claimed is:

1. A geodesic dome system for integrated aquaponics and mushroom production, comprising:
   a geodesic dome structure enclosing an interior volume and comprising a plurality of panels, the dome configured such that a first region of the interior volume receives direct sunlight and a second region of the interior volume remains substantially shaded;
   a fish tank disposed within a central portion of the interior volume and configured to contain fish;
   a water tube thermally coupled to the fish tank and extending outward therefrom, the water tube configured to regulate thermal energy within the dome;
   a plant growing area disposed within the first region of the interior volume;
   a mushroom growing area disposed within the second region of the interior volume; and
   a natural air ventilation system comprising a misting nozzle disposed at an upper portion of the dome and configured to introduce cooled misted air into the second region of the interior volume and to draw heated air from the first region of the interior volume upward toward the misting nozzle.

2. The system of claim 1, wherein the misting nozzle comprises a misting nozzle disposed atop a plenum structure positioned above the water tube, the misting nozzle configured to rotate 360 degrees to direct misted air toward the mushroom growing area.

3. The system of claim 2, wherein the plenum structure comprises a mushroom-shaped profile and is thermally coupled to the water tube.

4. The system of claim 1, wherein the misting nozzle is further configured to deliver evaporatively cooled air based on environmental conditions within the interior volume.

5. The system of claim 1, wherein at least one of the plurality of panels is selectively transmissive, reflective, or photovoltaic.

6. The system of claim 5, wherein the at least one of the plurality of panels is rotatably mounted and coupled to a stepper motor.

7. The system of claim 6, wherein the stepper motor is configured to be controlled based on signals received from one or more environmental sensors.

8. The system of claim 5, wherein the at least one of the plurality of panels is dynamically adjusted to define the first region and the second region.

9. The system of claim 1, further comprising a computer system configured to control at least one of the misting nozzle, panel orientation, or airflow based on input from one or more sensors.

10. The system of claim 9, wherein the input from one or more sensors comprises measurements of temperature, humidity, light, oxygen, or carbon dioxide.

11. The system of claim 9, wherein the computer system is configured to regulate environmental parameters using an adaptive control model.

12. The system of claim 1, wherein the water tube is further configured to store thermal energy during daylight hours and to release the thermal energy during cooler periods.

13. The system of claim 12, wherein the water tube is thermally coupled to the fish tank to maintain a stable water temperature within the fish tank.

14. The system of claim 1, wherein the plant growing area and the mushroom growing area each comprise a plurality of grow beds arranged radially around the fish tank.

15. The system of claim 1, further comprising a rainwater collection system integrated into the geodesic dome structure and configured to direct water into the fish tank.

16. The system of claim 1, wherein the interior volume comprises a circular swale and berm system configured to receive water from the fish tank or the plant growing area, the circular swale and berm system configured to direct the water through a sequence of alternating berms and swales and return the water to the fish tank after filtration.

17. The system of claim 16, wherein the berms are planted with vegetation and are configured to support food production.

18. The system of claim 16, wherein the fish tank is further configured to receive filtered water from the circular swale and berm system through a gravity-fed return channel.

19. The system of claim 1, wherein the natural air ventilation system further comprises a plurality of programmable vents distributed throughout the geodesic dome structure and configured to modulate airflow within the interior volume.

20. The system of claim 1, wherein the misting nozzle is further configured to activate based on a humidity threshold detected within the mushroom growing area.

* * * * *